(12) United States Patent
Smith et al.

(10) Patent No.: US 10,550,193 B2
(45) Date of Patent: Feb. 4, 2020

(54) METHODS AND ANTIBODY COMPOSITIONS FOR TUMOR TREATMENT

(71) Applicant: Regeneron Pharmaceuticals, Inc., Tarrytown, NY (US)

(72) Inventors: Eric Smith, New York, NY (US); Samuel Davis, New York, NY (US); Bindu Varghese, Hopewell Junction, NY (US); Jessica R. Kirshner, New York, NY (US); Gavin Thurston, Briarcliff Manor, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 955 days.

(21) Appl. No.: 14/661,334

(22) Filed: Mar. 18, 2015

(65) Prior Publication Data

US 2015/0266966 A1    Sep. 24, 2015

Related U.S. Application Data

(60) Provisional application No. 61/955,663, filed on Mar. 19, 2014, provisional application No. 61/981,641, filed on Apr. 18, 2014, provisional application No. 62/007,385, filed on Jun. 3, 2014, provisional application No. 62/033,460, filed on Aug. 5, 2014.

(51) Int. Cl.
| C07K 16/20 | (2006.01) |
| C07K 16/28 | (2006.01) |
| A61K 39/00 | (2006.01) |

(52) U.S. Cl.
CPC ...... *C07K 16/2887* (2013.01); *C07K 16/2803* (2013.01); *A61K 2039/505* (2013.01); *C07K 2317/31* (2013.01); *C07K 2317/33* (2013.01); *C07K 2317/51* (2013.01); *C07K 2317/52* (2013.01); *C07K 2317/522* (2013.01); *C07K 2317/524* (2013.01); *C07K 2317/526* (2013.01); *C07K 2317/53* (2013.01); *C07K 2317/56* (2013.01); *C07K 2317/565* (2013.01); *C07K 2317/73* (2013.01); *C07K 2317/92* (2013.01)

(58) Field of Classification Search
None
See application file for complete search history.

(56) References Cited

U.S. PATENT DOCUMENTS

| 5,500,362 A | 3/1996 | Robinson et al. |
| 5,624,821 A | 4/1997 | Winter et al. |
| 5,648,260 A | 7/1997 | Winter et al. |
| 5,658,570 A | 8/1997 | Newman et al. |
| 5,677,180 A | 10/1997 | Robinson et al. |
| 5,721,108 A | 2/1998 | Robinson et al. |
| 5,736,137 A | 4/1998 | Anderson et al. |
| 5,776,456 A | 7/1998 | Anderson et al. |
| 5,843,439 A | 12/1998 | Anderson et al. |
| 6,120,767 A | 9/2000 | Robinson et al. |
| 6,180,377 B1 | 1/2001 | Morgan et al. |
| 6,224,866 B1 | 5/2001 | Barbera-Guillem |
| 6,399,061 B1 | 6/2002 | Anderson et al. |
| 6,455,043 B1 | 9/2002 | Grillo-Lopez |
| 6,528,624 B1 | 3/2003 | Idusogie et al. |
| 6,551,592 B2 | 4/2003 | Lindhofer et al. |
| 6,652,852 B1 | 11/2003 | Robinson et al. |
| 6,682,734 B1 | 1/2004 | Anderson et al. |
| 6,893,625 B1 | 5/2005 | Robinson et al. |
| 7,151,164 B2 | 12/2006 | Hansen et al. |
| 7,214,775 B2 | 5/2007 | Hanai et al. |
| 7,396,917 B2 | 7/2008 | Bowdish et al. |
| 7,563,441 B2 | 7/2009 | Graus et al. |
| 7,597,889 B1 | 10/2009 | Armour et al. |
| 7,608,260 B2 | 10/2009 | Schenerman et al. |

(Continued)

FOREIGN PATENT DOCUMENTS

| EP | 0327378 B1 | 12/1996 |
| EP | 1400534 A1 | 3/2004 |

(Continued)

OTHER PUBLICATIONS

Tsai et al. (Clin Cancer Res; 18(4); 1039-50. (2012)) (Year: 2012).*
Stubenrauch et al. (Drug Metab Dispos. Jan. 2010;38(1):84-91) (Year: 2010).*
Damschroder et al. (Mol Immunol. Aug. 2004;41(10):985-1000) (Year: 2004).*
Harlow et al. (Antibodies, A Laboratory Manual, Cold Spring Harbor laboratory, 1988, pp. 37-47) (Year: 1988).*
Ruf et al. (Blood. 2001; 98:2526-2534) (Year: 2001).*
Bargou et al. (Science, 2008, vol. 321, pp. 974-977) (Year: 2008).*
Buhmann et al. (Bone Marrow Transplantation (2009) 43, 383-397) (Year: 2009).*

(Continued)

*Primary Examiner* — Zachary S Skelding
(74) *Attorney, Agent, or Firm* — Schwabe, Williamson & Wyatt PC; Aparna G. Patankar

(57) ABSTRACT

The present invention provides bispecific antibodies that bind to CD3 and tumor antigens and methods of using the same. According to certain embodiments, the bispecific antibodies of the invention exhibit reduced effector functions and have a unique binding profile with regard to Fcγ receptors. The bispecific antibodies are engineered to efficiently induce T cell-mediated killing of tumor cells. According to certain embodiments, the present invention provides bispecific antigen-binding molecules comprising a first antigen-binding domain that specifically binds human CD3, a second antigen-binding molecule that specifically binds human CD20, and an Fc domain that binds Fcγ receptors with a specific binding pattern. In certain embodiments, the bispecific antigen-binding molecules of the present invention are capable of inhibiting the growth of B-cell or melanoma tumors expressing CD20. The bispecific antibodies of the invention are useful for the treatment of various cancers as well as other CD20-related diseases and disorders.

32 Claims, 26 Drawing Sheets

Specification includes a Sequence Listing.

(56) References Cited

U.S. PATENT DOCUMENTS

| | | | |
|---|---|---|---|
| 7,700,097 B2 | 4/2010 | Braslawsky et al. | |
| 7,700,099 B2 | 4/2010 | Strohl | |
| 7,728,114 B2* | 6/2010 | Mach | C07K 16/2809 530/388.15 |
| 7,824,684 B2 | 11/2010 | Graus et al. | |
| 7,867,491 B2 | 1/2011 | Yang et al. | |
| 7,879,984 B2 | 2/2011 | Martin et al. | |
| 7,960,512 B2 | 6/2011 | Stavenhagen et al. | |
| 8,075,884 B2 | 12/2011 | Bowdish et al. | |
| 8,076,459 B2 | 12/2011 | Hofmeister et al. | |
| 8,084,026 B2 | 12/2011 | Glaser et al. | |
| 8,097,713 B2 | 1/2012 | Martin et al. | |
| 8,153,583 B2 | 4/2012 | Carton et al. | |
| 8,236,314 B2 | 8/2012 | Kai et al. | |
| 8,268,972 B2 | 9/2012 | Whitfeld et al. | |
| 8,329,181 B2 | 12/2012 | Martin et al. | |
| 8,383,109 B2 | 2/2013 | Lazar et al. | |
| 8,409,568 B2 | 4/2013 | Gao et al. | |
| 8,961,967 B2 | 2/2015 | Strohl et al. | |
| 2003/0026804 A1 | 2/2003 | Grillo-Lopez | |
| 2004/0093621 A1 | 5/2004 | Shitara et al. | |
| 2004/0167319 A1 | 8/2004 | Teeling et al. | |
| 2005/0025764 A1 | 2/2005 | Watkins et al. | |
| 2005/0037000 A1 | 2/2005 | Stavenhagen et al. | |
| 2005/0053602 A1 | 3/2005 | Brunetta | |
| 2005/0191297 A1 | 9/2005 | Brunetta | |
| 2005/0226876 A1 | 10/2005 | Graus et al. | |
| 2005/0244403 A1 | 11/2005 | Lazar et al. | |
| 2005/0271658 A1 | 12/2005 | Brunetta et al. | |
| 2006/0024295 A1 | 2/2006 | Brunetta | |
| 2006/0110387 A1 | 6/2006 | Dahiyat et al. | |
| 2006/0121032 A1 | 6/2006 | Dahiyat et al. | |
| 2006/0193852 A1 | 8/2006 | Dorken et al. | |
| 2006/0233797 A1 | 10/2006 | Gujrathi | |
| 2006/0240007 A1 | 10/2006 | Sanders | |
| 2006/0263355 A1 | 11/2006 | Quan et al. | |
| 2007/0009523 A1 | 1/2007 | Presta | |
| 2007/0014720 A1 | 1/2007 | Gazit-Bornstein et al. | |
| 2007/0020259 A1 | 1/2007 | Hansen et al. | |
| 2007/0041972 A1 | 2/2007 | Rother et al. | |
| 2007/0081993 A1 | 4/2007 | Kufer et al. | |
| 2009/0022738 A1 | 1/2009 | Hofmeister et al. | |
| 2009/0035322 A1 | 2/2009 | Martin et al. | |
| 2009/0117133 A1 | 5/2009 | Arnason et al. | |
| 2009/0162901 A1 | 6/2009 | Chen et al. | |
| 2009/0252729 A1 | 10/2009 | Farrington et al. | |
| 2010/0105874 A1 | 4/2010 | Schuurman et al. | |
| 2010/0166749 A1 | 7/2010 | Presta | |
| 2010/0178298 A1 | 7/2010 | Lindhofer | |
| 2010/0183554 A1 | 7/2010 | Mach et al. | |
| 2010/0183615 A1 | 7/2010 | Kufer et al. | |
| 2010/0267934 A1 | 10/2010 | Winkel et al. | |
| 2010/0298542 A1 | 11/2010 | Igawa et al. | |
| 2010/0325744 A1 | 12/2010 | Schuurman et al. | |
| 2010/0331527 A1* | 12/2010 | Davis | C07K 16/2809 530/387.3 |
| 2011/0077383 A1 | 3/2011 | Dall'Acqua et al. | |
| 2011/0212087 A1 | 9/2011 | Strohl et al. | |
| 2011/0245473 A1 | 10/2011 | Igawa et al. | |
| 2011/0263830 A1 | 10/2011 | Goetsch et al. | |
| 2011/0293607 A1 | 12/2011 | Labrijn et al. | |
| 2012/0065379 A1 | 3/2012 | Igawa et al. | |
| 2012/0071634 A1 | 3/2012 | Igawa et al. | |
| 2012/0100140 A1 | 4/2012 | Reyes et al. | |
| 2012/0189643 A1 | 7/2012 | Carton et al. | |
| 2012/0225058 A1 | 9/2012 | Lazar et al. | |
| 2012/0237515 A1 | 9/2012 | Bell et al. | |
| 2012/0238729 A1 | 9/2012 | Kuramochi et al. | |
| 2012/0251531 A1 | 10/2012 | Baehner et al. | |
| 2012/0276096 A1 | 11/2012 | Yang et al. | |
| 2012/0276097 A1 | 11/2012 | Yang et al. | |
| 2013/0011386 A1 | 1/2013 | Brerski et al. | |
| 2013/0101581 A1 | 4/2013 | Kuramochi et al. | |
| 2013/0108623 A1 | 5/2013 | D'Angelo et al. | |
| 2013/0129723 A1 | 5/2013 | Blankenship et al. | |
| 2013/0251707 A1 | 9/2013 | Kontermann et al. | |
| 2014/0088295 A1* | 3/2014 | Smith | C07K 16/2809 530/387.3 |
| 2014/0112914 A1* | 4/2014 | Nezu | C07K 16/30 424/133.1 |
| 2014/0120581 A1 | 5/2014 | Niwa et al. | |
| 2014/0243504 A1 | 8/2014 | Davis et al. | |
| 2015/0166661 A1* | 6/2015 | Chen | C07K 16/2809 424/135.1 |
| 2015/0203579 A1 | 7/2015 | Papadopoulos et al. | |
| 2016/0168247 A1* | 6/2016 | Van Den Brink | C07K 16/1063 424/136.1 |
| 2016/0347839 A1 | 12/2016 | Davis et al. | |
| 2017/0008951 A1 | 1/2017 | Block et al. | |
| 2018/0303953 A1 | 10/2018 | Van Berkel | |

FOREIGN PATENT DOCUMENTS

| | | | |
|---|---|---|---|
| EP | 1176981 B1 | 11/2005 | |
| EP | 1185299 B1 | 1/2007 | |
| EP | 2500353 A2 | 9/2012 | |
| EP | 2918604 A1 | 9/2015 | |
| WO | WO 97/028267 A1 | 8/1997 | |
| WO | WO 99/043713 A1 | 9/1999 | |
| WO | 99/058572 A1 | 11/1999 | |
| WO | WO 00/042072 A2 | 7/2000 | |
| WO | 03/026490 A2 | 4/2003 | |
| WO | WO 04/106380 A2 | 9/2004 | |
| WO | WO 04/106383 A2 | 12/2004 | |
| WO | WO 05/000901 A2 | 1/2005 | |
| WO | WO 05/040220 A1 | 5/2005 | |
| WO | WO 06/130458 A2 | 12/2006 | |
| WO | WO 07/024715 A2 | 3/2007 | |
| WO | WO 07/042261 A2 | 4/2007 | |
| WO | WO 07/093630 A1 | 8/2007 | |
| WO | WO 08/119567 A2 | 10/2008 | |
| WO | 09/018411 A1 | 2/2009 | |
| WO | 10/054212 A1 | 5/2010 | |
| WO | WO 10/063785 A2 | 6/2010 | |
| WO | WO 10-085682 A2 | 7/2010 | |
| WO | WO 11/090762 A1 | 7/2011 | |
| WO | WO 11/137362 A1 | 11/2011 | |
| WO | WO 12/022982 A2 | 2/2012 | |
| WO | WO 12/035141 A1 | 3/2012 | |
| WO | WO 12/087746 A1 | 6/2012 | |
| WO | WO-2012073985 A1 * | 6/2012 | C07K 16/30 |
| WO | 13/026839 A1 | 2/2013 | |
| WO | WO 13/112986 A1 | 8/2013 | |
| WO | 13/184761 A1 | 12/2013 | |
| WO | WO 14/012085 A2 | 1/2014 | |
| WO | WO 14/022540 A1 | 2/2014 | |
| WO | WO 14/047231 A1 | 3/2014 | |
| WO | 14/051433 A1 | 4/2014 | |
| WO | 14/056783 A1 | 4/2014 | |
| WO | WO 14/121087 A1 | 8/2014 | |
| WO | WO-2015006749 A2 * | 1/2015 | C07K 16/2803 |
| WO | 15/091738 A1 | 6/2015 | |
| WO | WO 15/143079 A1 | 9/2015 | |
| WO | WO 13/012733 A1 | 11/2015 | |
| WO | WO 16/081490 A1 | 5/2016 | |
| WO | 16/161010 A2 | 10/2016 | |
| WO | 17/053856 A1 | 3/2017 | |
| WO | 17/112762 A1 | 6/2017 | |

OTHER PUBLICATIONS

Kapur et al. (Immunology Letters 160 (2014) 139-144). (Year: 2014).*

U.S. Appl. No. 15/147,791, Notice of Allowance dated Mar. 1, 2018.

U.S. Appl. No. 15/386,443, Requirement for Restriction/Election dated Apr. 20, 2018.

Siiman et al., "Cell Surface Receptor-Antibody Association Constants and Enumeration of Receptor Sites for Monoclonal Antibodies," Cytometry, 40:316-326, (2000).

(56) References Cited

OTHER PUBLICATIONS

U.S. Appl. No. 15/147,791, Notice of Allowance dated Jun. 12, 2018.
Boehrer et al., "Cytotoxic effects of the trifunctional bispecific antibody FBTACI5 in ex-vivo cells of chronic lymphocytic leukaemia depend on immune-mediated mechanisms," Anti-Cancer Drugs, 22:519-530, (2011).
Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplantation, 43:383-397, (2009).
Carter, "Potent Antibody Therapeutics by Design," Journal of Immunology, Nature Pub. Group, 6:343-357, (2006).
Gall et al., "T cells armed with anti-CD3 x anti-CD20 bispecific antibody enhance killing of CD20+ malignant B cells and bypass complement-mediated rituximab resistance in vitro", Experimental Hematology, 33(4):452-459, (2005).
Klein et al., "Progress in overcoming the chain association issue in bispecific heterodimeric lgG antibodies," mAbs, Landes Bioscience, 4(6):1-11, (2012).
Klinger et al., "Immunopharmacologic response of patients with B-lineage acute lymphoblastic leukemia to continuous infusion of T cell-engaging CD19/CD3-bispecific BiTE antibody blinatumomab," Blood, 119:6226-6233, (2012).
Kontermann, "Dual targeting strategies with bispecific antibodies," mAbs, Landes Bioscience, 4(2):182-197, (2012).
Kung et al., "Monoclonal Antibodies Defining Distinctive Human T Cell Surface Antigens," Science, 206:347-349, (1979).
Leonard et al., "Targeted Treatment and New Agents in Diffuse Large B-Cell Lymphoma," Semin Hematol, 45(suppl 2):S11-S16, (2008).
Liu et al., "Improvement in soluble expression levels of a diabody by exchanging expression vectors", Protein Expression and Purification, 62:15-20, (2008).
Nagorsen et al., "Blinatumomab: A historical perspective," Pharmacology & Therapeutics, 136:334-342 (2012).
Patel et al., "IGG subclass variation of a monoclonal antibody binding to human Fc-gamma receptors", American Journal of Biochemistry and Biotechnology, 9(3):206-218, (2013).
Pessano et al., "The T3fT cell receptor complex: antigenic distinction between the two 20-kd JT3 (T3-6 and T3-€) subunits," The EMBO Journal, 4(2):337-344, (1985).
Segal et al., "Bispecific antibodies in cancer therapy, "Current Opinion in Immunology, 11:558-562, (1999).
Stanglmaier et al., "Bi20 (FBTA05), a novel trifunctional bispecific antibody (anti-CD20 x anti-CD3), mediates efficient killing of B-cell lymphoma cells even with very low CD20 expression levels", Int. J. Cancer, 123(5):1181-1189, (2008).
Stel et al., "The role of B cell-mediated T cell costimulation in the efficacy of the T cell retargeting bispecific antibody BIS20x3," J Immunol, 173(10):6009-6016, (2004).
Strop et al., "Generating Bispecific Human IgG1 and IgG2 Antibodies from Any Antibody Pair", J. Mol. Biol., 420(3):204-219, (2012).
Teeling et al., "Characterization of new human CD20 monoclonal antibodies with potent cytolytic activity against non-Hodgkin lymphomas," Blood, 104:1793-1800, (2004).
Thakur et al., "Activated T cells from umbilical cord blood armed with anti-CD3 x anti-CD20 bispecific antibody mediate specific cytotoxicity against CD20+ targets with minimal allogeneic reactivity: a strategy for providing antitumor effects after cord blood transplants", Transfusion, 52:63-75, (2012).
Van Meerten al., "CD2O-Targeted Therapy: The Next Generation of Antibodies," Semin Hematol, 47:199-210, (2010).
Wark et al., "Latest technologies for the enhancement of antibody affinity", Advanced Drug Delivery Reviews, 58(5-6):657-670, (2006).
WIPO Application No. PCT/US2013/060511, PCT International Search Report and Written Opinion of the International Searching Authority dated Feb. 20, 2014.

WIPO Application No. PCT/US2015/021322, PCT International Search Report and Written Opinion of the International Searching Authority dated Jul. 2, 2015.
Xiong et al., "Efficient inhibition of human B-cell lymphoma xenografts with an anti-CD20 X anti-CD3 bispecific diabody", Cancer Letters, 177:29-39, (2002).
Conrad et al., "TCR and CD3 Antibody Cross-Reactivity in 44 Species," Cytometry Part A, 71A:925-933, (2007).
Lum et al., "CD2O-Targeted T Cells after Stem Cell Transplantation for High Risk and Refractory Non-Hodgkin's Lymphoma," Pbiol Blood Marrow Transplant, 19(6):925-933, (2013).
Lum et al., "Multiple infusions of CD20-targeted T cells and low-dose IL-2 after SCT for high-risk non-Hodgkin's lymphoma: A pilot study," Bone Marrow Transplantation, 49:73-79, (2004). [Puplished online Sep. 23, 2013].
Sun et al., "Anti-CD20/CD3 T cell-dependent bispecific antibody for the treatment of B cell malignancies," Science Translational Medicine, 7(287):287ra70, 10 pages, (2015).
U.S. Appl. No. 14/031,075, Non-Final Office Action dated Apr. 15, 2016.
U.S. Appl. No. 14/170,166, Notice of Allowance dated Apr. 11, 2016.
Winkler et al., "Changing the Antigen Binding Specificity by Single Point Mutations of an Anti-p24 (HIV-1) Antibody," J. Immunol., 165:4505-4514, (2000).
WIPO Application No. PCT/US2015/061139, PCT International Search Report and Written Opinion of the International Searching Authority dated Feb. 18, 2016.
U.S. Appl. No. 15/527,002, Requirement for Restriction/Election dated Aug. 24, 2018.
U.S. Appl. No. 15/386,443, Requirement for Restriction/Election dated Sep. 19, 2018.
Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," Journal of Translation Medicine, vol. 11:160, (2013); 9 pages. [Retrieved from the Internet at: <http://www.translational-medicine.com/content/11/1/1160>].
U.S. Appl. No. 14/031,075, Final Office Action dated Sep. 14, 2016.
U.S. Appl. No. 14/031,075, Notice of Allowance dated Jan. 18, 2014.
WIPO Application No. PCT/US2016/025051, PCT International Search Report and Written Opinion of the International Searching Authority dated Oct. 12, 2016.
Hezareh et al., "Effector function activities of a panel of mutants of a broadly neutralizing antibody against human immunodeficiency virus type 1," J Virol, 75(24):12161-12168, doi: 10.1128/JVI.75.24.12161-12168.2001, (2001).
Shields et al., High resolution mapping of the binding site on human IgG1 for FcgammaRI, FcganmaRII, FcgammaRIII, and FcRn and design of IgG1 variants with improved binding to the FcgammaR, J Biol Chem, 276(9):6591-6604, doi: 10.1074/JBC.M009483200, (2001).
Alegre et al., "Effect of a Single Amino Acid Mutation on the Activating and Immunosuppressive Properties of a Humanized OKT3 Monoclonal Antibody", J Immunol, 148(11):3461-3468, ISSN: 0022-1767, (1992).
Vidarsson et al., "IgG Subclasses and Allotypes: From Structure to Effector Functions," Frontiers in Immunology, vol. 5, Article 520, 18 pages, doi: 10.3389/fimmu.2014.00520, (2014).
WIPO Application No. PCT/US2016/053525, PCT International Search Report and Written Opinion of the International Searching Authority dated Mar. 8, 2017.
Wu et al., "Fab-based bispecific antibody formats with robust biophysical properties and biological activity," MABS, pp. 470-482, ISSN: 1942-0870, (2015).
Cao et al., "Multiformat T-Cell-Engaging Bispecific Antibodies Targeting Human Breast Cancers," Angew Chem Int Ed Engl, 54(24):7022-7027, doi: 10.1002/anie.201500799, (2015).

(56) References Cited

OTHER PUBLICATIONS

Jung et al., "Target Cell-Induced T Cell Activation with Bi- and Trispecific Antibody Fragments", Eur J Immunol, vol. 21, pp. 2431-2435, doi: 10.1002/EJI.1830211020, (1991).
Fossati et al., "Immunological changes in the ascites of cancer patients after intraperitoneal administration of the bispecific antibody catumaxomab (anti-EpCAManti-CD3)," Gynecol Oncol, 138(2):343-351, doi: 10.1016/J.YGYNO.2015.06.003, (2015).
Schaefer et al., "Immunoglobulin domain crossover as a generic approach for the production of bispecific IgG antibodies," PNAS, 108(27):11187-11192, doi: 10.1073/pnas.1019002108, (2011).
Li et al., "A Novel Bispecific Antibody, S-Fab, Induces Potent Cancer Cell Killing," J Immunother, 38(9):350-356, doi: 10.1097/CJI.0000000000000099, (2015).
Almagro et al., "Humanization of antibodies," Front Biosci, vol. 13, pp. 1619-1163, (2008).
Baeuerle et al., "Bispecific T-cell engaging antibodies for cancer therapy," Cancer Res, 69(12):4941-4944, doi: 10.1158/0008-5472.CAN-09-0547, (2009).
Lau et al., "Chimeric Anti-CD14 IGG2/4 Hybrid Antibodies for Therapeutic Intervention in Pig and Human Models of Inflammation," J Immunol, 191:4769-4777, doi: 10.4049/jimmunol.1301653, (2013).
WIPO Application No. PCT/US2016/068003, PCT International Search Report dated Mar. 31, 2017.
WIPO Application No. PCT/US2016/068003, PCT Written Opinion of the International Searching Authority dated Mar. 31, 2017.
Schuster et al., "Immunotherapy with the trifunctional anti-CD20 x anti-CD3 antibody FBTA05 Lymphomun) in pediatric high-risk patients with recurrent CD20-positive B cell malignancies," British Journal of Haematolgy, Vol. 169 (No. 1): (Apr. 11, 2015); pp. 90-102.
Smith et al., "A novel, native-format bispecific antibody triggering T-cell killing of B-cell is robustly active in mouse tumor models and cynomolgus monkeys," Scientific Reports, vol. 5(No. 11):(Dec. 11, 2015); p. 17943.
Anonymous, "Clinical Trails Register: A Phase I Study to Assess Safety and Tolerability of REGN1979, an anti-CD20 x anti- CD3 bispecific monoclonal antibody, and REGN2810, and antiprogrammed death-1 (PD-1) monoclonal antibody, in Patients with B-cell Malignancies," p. 1, section A.3; p. 3, section E.1 [Retrieved from the Internet Mar. 14, 2017: <URL: https://www.clinicaltrailsregister.eu/ctr-search/trial/2015-001697-17/ES>].
Anonymous, "Study of REGN2810 and REGN1979 in Patients with Lymphoma or Acute Lymphoblastic Leukemia." [Retrieved from the Internet Mar. 15, 2017: <URL: https://www.api.liveclinicaltrials.com/trialpage?dcn=10963&city=Baltimore&country=UnitedStates&start=20&state=Maryland&conditions=lymphoma&id=207048402254>].
Advani et al., "New immune strategies for the treatment of acute pymphoblastic leukemia: antiobodies and chimeric antigen receptors," Hematology, vol. 2013 (No. 1): (Dec. 1, 2013).
U.S. Appl. No. 15/147,791, Non-Final Office Action dated Sep. 27, 2017.
Becker et al., "Evaluation of a combinatorial cell engineering approach to overcome apoptotic effects in XBP-1(s) expressing cells," Journal of Biotechnology, vol. 164:198-206, (2010).
"IgG-Fc Engineering for Therapeutic Use," InvivoGen Insight, 1 page, (2006). [Author Unknown] [Retrieved from the Internet Apr. 4, 2014: <URL: http://www.invivogen.comiclocs/Insight200605 pdf >].
"IgG-Fe engineering for therapeutic use," Invivogen, 2 pages, (2007). [Author Unknown] [Retrieved from the Internet Jan. 12, 2011: <URL: http://www.invivogen.com/ressource.php?ID=22].
Aalberse et al., "IgG4 breaking the rules," Immunology, 105(1):9-19, (2002).
An et al., "IgG2m4, an engineered antibody isotype with reduced Fc function," Landes Bioscience, 1(6):572-579, (2009).
Armour et al., "Differential binding to human FcγRIIa and FcγRIIb receptors by human IgG wildtype and mutant antibodies," Molecular Immunology, 40:585-593, (2003).
Armour et al., "Recombinant human IgG molecules lacking Fcγ receptor I binding and monocyte triggering activities", J. Immunol., 29: 2613-2624, (1999).
Bloom et al., "Intrachain disulfide bond in the core hinge region of human IgG4," Protein Science, 6:407-415, (1997).
Brekke et al., "The structural requirements for complement activation by IgG: does it hinge on the hinge?" Today, 16(2):85-90, (1995).
Canfield et al., "The Binding Affinity of Human Igg for Its High Affinity FC Receptor is Determined by Multiple Amino Acids in the Ch2 Domain and is Modulated by the Hinge Region," J. Exp. Med., 173(6):1483-1491, (1991).
Chappel et al., "Identification of a Secondary FcγRI Binding Site within a Genetically Engineered Human IgG," Journal of Biological Chemistry, 268(33): 25124-25131, (1993).
Chappel et al., "Identification of the Fc-Gamma Receptor Class I Binding Site in Human Igg Through the Use of Recombinant Igg1-Igg2 Hybrid and Point-Mutated Antibodies," Proc. Natl. Acad. Sci. USA, 88(20):9036-9040, (1991).
Clark, "IgG Effector Mechanisms," Chem Immunol. Basel, Karger, 65:88-110, (1997).
Dall'Acqua et al., "Modulation of the Effector Functions of a Human IgG1 through Engineering of Its Hinge Region," Journal of Immunology, 177:1129-1138, (2006).
DANGL et al., "Segmental flexibility and complement fixation of genetically engineered chimeric human, rabbit and mouse antibodies," The EMBO Journal, 7(7):1989-1994, (1988).
Duncan et al., "Localization of the binding site for the human high-affinity Fc receptor on IgG", Nature, 332:563-564, (1988).
Gergely et al., "The two binding-site models of human IgG binding Fcγ receptors", The FASEB Journal, 4:3275-3283, (1990).
Greenwood et al., "Structural Motifs Involved in Human IGG Antibody Effector Functions," Eur. J. Immunology, 23(5):1098-1104, (1993).
Jacobsen et al., "Molecular and Functional Characterization of Cynomolgus Monkey IgG Subclasses," Journal Immunology, 186:341-349, (2011).
Jefferis et al., "Interaction sites on human IgG-Fc for FcγR: current models", Immunology Letters, 82:57-65, (2002).
Jefferis et al., "Recognition sites on human IgG for Fcγ receptors: the role of glycosylation," Immunology Letters, 44:111-117, (1995).
Labrijn et al., "When binding is enough: nonactivating antibody formats", Current Opinion in Immunology, 20:479-485, (2008).
Lund et al., "Human FcγRI and FcγRII Interact with Distinct but Overlapping Sites on Human IgG", Journal of Immunology, 147(8):2657-2662, (1991).
Michaelsen et al., "Antibody Dependent Cell-Mediated Cytotoxicity Induced by Chimeric Mouse-Human IgG Subclasses and IgG3 Antibodies with Altered Hinge Region," Molecular Immunology, 29(3):319-326, (1992).
Morgan et al., "The N-terminal end of the CH2 domain of chimeric human IgG1 anti-HLA-DR is necessary for Gig, FcγRI and FcγRII binding," Immunology, 86:319-324, (1995).
Mueller et al., "Humanized Porcine VCAM-Specific Monoclonal Antibodies with Chimeric IgG2/G4 Constant Regions Block Human Leukocyte Binding to Porcine Endothelial Cells," Molecular Immunology, 34(6): 441-452, (1997).
Natsume et al., "Engineered Antibodies of IgG1IIgG3 Mixed Isotype with Enhanced Cytotoxic Activities," Cancer Research, 68:(10):3863-3872, (2008).
Oganesyan et al., "Structural characterization of a human Fc fragment engineered for lack of effector functions," Acta Crystallographica Section D Biological Crystallography, D64:700-704, (2008).
Peters et al., "Engineering an improved IgG4 Molecule with Reduced Disulfide Bond Heterogeneity and Increased Fab Domain Thermal Stability," Journal of Biological Chemistry, 287(29): 24525-24533, (2012).

(56) References Cited

OTHER PUBLICATIONS

Reddy et al., "Elimination of Fc Receptor-Dependent Effector Functions of a Modified IgG4 Monoclonal Antibody to Human CD4," Journal of Immunology, 164:1925-1933, (2000).
Rother et al., : "Discovery and development of the complement inhibitor eculizumab for the treatment of paroxysmal nocturnal hemoglobinuna," Nature Biotechnology, 25(11):1256-1264, (2007).
Roux et al., "Comparisons of the ability of human IgG3 hinge mutants, IgM, IgE and IgA2, to form small immune complexes: Arole for flexibility and geometry," The Journal of Immunology, 161:4083-4090, (1998).
Roux et al., "Flexibility of Human IgG Subclasses," Journal of Immunology, 159:3372-3382, (1997).
Salfeld, "Isotype selection in antibody engineering," Nature Biotechnology, 25(12):1369-1372, (2007).
Sarmay et al., "Mapping and Comparison of the Interaction Sites on the Fc Region of IgG Responsible for Triggering Antibody Dependent Cellular Cytotoxicity (ADCC) through Different Types of Human Fcγ Receptor," Molecular Immunology, 29(5):633-639, (1992).
Sathish et al., "Challenges and approaches for the development of safer immunomodulatory biologics," Nature Reviews Drug Discovery, 12:306-324, (2013).
Sensel et al., "Amino Acid Differences in the N-Terminus of CH2 Influence the Relative Abilities of IgG2 and IgG3 to Activate Complement", Molecular Immunology, 34(14):1019-1029, (1997).
Siberil et al., "Molecular aspects of human FcγR interactions with IgG: Functional and therapeutic consequences," Immunology Letters, 106:111-118, (2006).
Stevenson, "Chemical Engineering at the Antibody Hinge," Chem Immunol. Basel, Karger, 65:57-72, (1997).
Tan et al., "Influence of the hinge region on complement activation, C1q binding, and segmental flexibility in chimeric human immunoglobulins,", Proc. Natl. Acad. Sci. USA, 87:162-166, (1990).
Vafa, et al., "An engineered Fc variant of an IgG eliminates all immune effector functions via structural perturbations", 65:114-126, (2014). (published online Jul. 17, 2013).
Ward et al., "The effector functions of immunoglobulins: implications for therapy," Therapeutic Immunology, 2:77-94, (1995).
Wypych et al., "Human IgG2 Antibodies Display Disulfide-mediated Structural Isoforms," Journal of Biological Chemistry, 283(23):16194-16205, (2008).
Xu et al., "Residue at Position 331 in the Igg1 and Igg4 Ch2 Domains Contributes to Their Differential Ability to Blind and Activate Complement," Journal of Biological Chemistry, 269(5):3469-3474, (1994).
U.S. Appl. No. 14/031,075, Requirement for Restriction/Election dated Nov. 19, 2015.
U.S. Appl. No. 14/170,166, Non-Final Office Action dated Dec. 21, 2015.
U.S. Appl. No. 14/170,166, Requirement for Restriction/Election dated Jul. 27, 2015.
WIPO Application No. PCT/US2014/014175, PCT International Preliminary Report on Patentability dated Aug. 13, 2015.
WIPO Application No. PCT/US2014/014175, PCT International Search Report and Written Opinion of the International Searching Authority dated Jul. 9, 2014.
Grubb, "Human Immunoglobulin Allotypes and Mendelian Polymorphisms of the Human Immunoglobulin Genes," in Oss CJ, Regenmortel MHV (eds); Immunochemistry, New York, Dekker (1994); pp. 47-68.
Haso et al., "Anti-CD22-chimeric antigen receptors targeting B-cell precursor acute lymphoblastic leukemia," Blood, vol. 121(No. 7):1165-1174, (2013).
Köhnke et al., "Increase of PD-L1 expressing B-precursor ALL cells in a patient resistant to the CD19/CD3-bispecific T cell engager antibody blinatumomab," Journal of Hematology & Oncology, vol. 8 (No. 111):5 pages, (2015).
Kumar et al., "Expression of CD20 in B Cell Precursor Acute Lymphoblastic Leukemia," Indian J. Hematol Blood Transfus, vol. 30 (No. 1):16-18, (2014).
NCBI MedGen 44126 definition for "Pre-B Acute Lymphoblastic Leukemia" retrieved from the Internet on Dec. 11, 2018; pp. 1-4, available at <https://www.ncbi.nlm.nih.gov/medgen/44126> (2018).
Ontology Lookup Service, EFO 0000220, "acute lymphoblastic leukemia" retrieved from the Internet on Dec. 11, 2018, pp. 1-6; available at <httpx://www.ebi.ac.uk/ols/ontologies/efo/terms?short_form=EFO_0000220> (2018).
Thomas et al., "Chemoimmunotherapy with a modified hyper-CVAD and Rituximab Regiment improves outcome in De Novo Philadelphia Chromosome-Negative Precursor B-Lineage Acute Lymphoblastic Leukemia," Journal of Clinical Oncology, vol. 28 (No. 24):3880-3889, (2010).
Topp et al., "Safety and activity of blinatumomab for adult patients with relapsed or refractory B-precursor acute lymphoblastic leukemia: a multicentre, single-arm, phase 2 study," The Lancet, vol. 16:57-66, (2015).
U.S. Appl. No. 15/386,443, Non-Final Office Action dated Dec. 18, 2018.
U.S. Appl. No. 15/527,002, Non-Final Office Action dated Mar. 8, 2019.
Wolach et al., "Blinatumomab for the Treatment of Philadelphia Chromosome-Negative, Precursor B-cell Acute Lymphoblastic Leukemia," Clinical Cancer Research, vol. 21 (No. 19):4262-4269, (2015).
U.S. Appl. No. 61/704,029, filed Sep. 21, 2012, Expired.
U.S. Appl. No. 61/753,461, filed Jan. 17, 2013, Expired.
U.S. Appl. No. 61/763,110, filed Feb. 11, 2013, Expired.
U.S. Appl. No. 61/827,098, filed May 24, 2013, Expired.
U.S. Appl. No. 14/031,075, filed Sep. 19, 2013, 2014-0088295, Pending.
PCT/US2013/060511, Sep. 19, 2013, WO 2014/047231, Expired.
U.S. Appl. No. 61/955,663, filed Mar. 19, 2014, Expired.
U.S. Appl. No. 61/981,641, filed Apr. 18, 2014, Expired.
U.S. Appl. No. 62/007,385, filed Jun. 3, 2014, Expired.
U.S. Appl. No. 62/033,460, filed Aug. 5, 2014, Expired.
PCT/US2015/021322, Mar. 18, 2015, WO 2015/143079, Pending.
U.S. Appl. No. 61/763,110, filed Feb. 11, 2013, Expired, 9250P3.
U.S. Appl. No. 61/827,098, filed May 24, 2013, Expired, 9250P4.
U.S. Appl. No. 14/031,075, filed Sep. 19, 2013, US 2014-0088295, Pending, 9250-US.
PCT/US2013/060511, Sep. 19, 2013, WO 2014/047231, Expired, 9250-WO.
U.S. Appl. No. 14/170,166, filed Jan. 31, 2014, US 2014-0243504, Pending, 8550-US.
PCT/US2014/014175, Jan. 31, 2014, WO 14/121087, Expired, 8550-WO.
U.S. Appl. No. 61/955,663, filed Mar. 19, 2014, Expired, A0015P1.
U.S. Appl. No. 61/981,641, filed Apr. 18, 2014, Expired, A0015P2.
U.S. Appl. No. 62/007,385, filed Jun. 3, 2014, Expired, A0015P3.
U.S. Appl. No. 62/033,460, filed Aug. 5, 2014, Expired, A0015P4.
PCT/US2015/021322, Mar. 18, 2015, WO 2015/143079, Pending, A0015WO01.
U.S. Appl. No. 61/704,029, filed Sep. 21, 2012, Expired, 9250P1.
U.S. Appl. No. 61/753,461, filed Jan. 17, 2013, Expired, 9250P2.
U.S. Appl. No. 61/759,578, filed Feb. 1, 2013, Expired, 8550P1.
U.S. Appl. No. 14/170,166, filed Jan. 31, 2014, U.S. Pat. No. 9,359,437, Issued, 8550-US.
U.S. Appl. No. 62/080,716, filed Nov. 17, 2014, Expired, 10162P1-US.
U.S. Appl. No. 62/160,788, filed May 13, 2015, Expired, 10162P2-US.
PCT/US2015/061139, Nov. 17, 2015, WO 2016/081490, Pending, 10162WO01.
U.S. Appl. No. 15/147,791, filed May 5, 2016, Pending, 8550US02.
U.S. Appl. No. 61/759,578, filed Feb. 1, 2013, Expired.
U.S. Appl. No. 14/170,166, filed Jan. 31, 2014, U.S. Pat. No. 9,359,437, Issued.
U.S. Appl. No. 15/147,791, filed May 5, 2016, US 2016-0347839, Pending.
PCT/US2014/014175, Jan. 31, 2014, WO 2014/022540, Expired.

(56) References Cited

OTHER PUBLICATIONS

U.S. Appl. No. 14/031,075, filed Sep. 19, 2013, 9,657,102, Issued.
U.S. Appl. No. 15/489,666, filed Apr. 17, 2017, US 2017-0320948, Pending.
U.S. Appl. No. 15/934,447, filed Mar. 23, 2018, Pending.
PCT/US2015/021322, Mar. 18, 2015, WO 2015/143079, Expired.
U.S. Appl. No. 62/080,716, filed Nov. 17, 2014, Expired.
U.S. Appl. No. 62/160,788, filed May 13, 2015, Expired.
PCT/US2015/061139, Nov. 17, 2015, WO 2016/081490, Pending.
U.S. Appl. No. 15/527,002, filed Nov. 17, 2015, Pending.
U.S. Appl. No. 62/306,031, filed Mar. 9, 2016, Expired.
U.S. Appl. No. 15/386,443, filed Dec. 21, 2016, US 2017-0174781, Pending.
PCT/US2016/068003, Dec. 21, 2016, WO 2017/112762, Pending.
U.S. Appl. No. 62/140,350, filed Mar. 30, 2015, Expired.
PCT/US2016/025051, Mar. 30, 2016, WO 2016/161010, Pending.
U.S. Appl. No. 15/562,881, filed Mar. 30, 2016, Pending.
U.S. Appl. No. 62/222,605, filed Sep. 23, 2015, Expired.
PCT/US2016/053525, Sep. 23, 2016, WO 2017/053856, Pending.
U.S. Appl. No. 15/780,504, filed Sep. 23, 2016, Pending.
U.S. Appl. No. 15/147,791, filed May 5, 2016, US 2016-0347839, Pending, 8550U502.
PCT/US2014/014175, Jan. 31, 2014, WO 2014/022540, Expired, 8550-WO.
U.S. Appl. No. 14/031,075, filed Sep. 19, 2013, 9,657,102, Issued, 9250-US.
U.S. Appl. No. 15/489,666, filed Apr. 17, 2017, US 2017-0320948, Pending, 9250US02.
PCT/US2015/021322, Mar. 18, 2015, WO 2015/143079, Expired, A0015WO01.
U.S. Appl. No. 15/527,002, filed Nov. 17, 2015, Pending, 10162US01.
U.S. Appl. No. 62/306,031, filed Mar. 9, 2016, Expired, 10241P1-US.
U.S. Appl. No. 15/386,443, filed Dec. 21, 2016, US 2017-0174781, Pending, 10241US01.
PCT/US2016/068003, Dec. 21, 2016, WO 2017/112762, Pending, 10241WO01.
U.S. Appl. No. 62/140,350, filed Mar. 30, 2015, Expired, 10140P1-US.
PCT/US2016/025051, Mar. 30, 2016, WO 2016/161010, Pending, 10140WO01.
U.S. Appl. No. 15/562,881, filed Mar. 30, 2016, Pending, 10140US01.
U.S. Appl. No. 62/222,605, filed Sep. 23, 2015, Expired, 10151P1-US.
PCT/US2016/053525, Sep. 23, 2016, WO 2017/053856, Pending, 10151WO01.
U.S. Appl. No. 15/147,791, filed May 5, 2016, U.S. Pat No. 10,106,610, Issued.
U.S. Appl. No. 16/128,907, filed Sep. 12, 2018, US 2018-0371090, Pending.
U.S. Appl. No. 15/934,447, filed Mar. 23, 2018, US 2018-0215823, Pending.
U.S. Appl. No. 15/527,002, filed Nov. 17, 2015, US 2018-0194841, Pending.
PCT/US2016/025051, Mar. 30, 2016, WO 2016/161010, Expired.
U.S. Appl. No. 15/562,881, filed Mar. 30, 2016, US 2018-0282411, Pending.
U.S. Appl. No. 15/780,504, filed Sep. 23, 2016, US 2018/0355038, Pending.

\* cited by examiner

Construction of chimeric hinge

| | | Upper Hinge | | | | | | | | | | | Lower Hinge | | | | | | |
|---|---|---|---|---|---|---|---|---|---|---|---|---|---|---|---|---|---|---|---|
| | | E | P | K | S | C | D | K | T | H | T | C | P | | | | | | |
| IgG1 EU numbering | | 216 | 217 | 218 | 219 | 220 | 221 | 222 | 223 | 224 | 225 | 226 | 227 | | | | | | |
| IgG1 Kabat numbering | | 226 | 227 | 228 | 232[a] | 233[a] | 234[a] | | | 235 | 236 | 237 | 238 | 239 | 240 | | | | |
| IgG1 | | | | | 229[b] | 230[b] | 232[b] | | | | | | | | | | | | |
| | | | | | | | | | | | | | | P | C | P | A | P | P | V | A |
| IgG2 | EU | | | | | | | | | | | | | 228 | 229 | 230 | 231 | 232 | 233 | 234 | 235 |
| IgG2 | Kabat | | | | | | | | | | | | | 241 | 242 | 243 | 244 | 245 | 246 | 247 | 248 |
| | | E | S | K | Y | G | — | — | — | P | P | C | P | | | | | | |
| IgG4 EU numbering | | 216 | 217 | 218 | 219[b] | 220[b] | | | | 224 | 225 | 226 | 227 | | | | | | |
| IgG4 Kabat numbering | | 226 | 227 | 228 | 229 | 230 | | | | 237 | 238 | 239 | 240 | | | | | | |

- means no corresponding number reported
-- means no corresponding amino acid
[a] numbering according to the last updated IMGT Scientific Chart (IMGT®, the international ImMunoGeneTics information system®, http://www.imgt.org/IMGTScientificChart/Numbering/Hu_IGHGnber.html, created: 17 May 2001, last updated:10 Jan 2013)
[b] numbering according to EU index as reported in Kabat, E.A. et al. Sequences of Proteins of Immunological Interest. 5th ed. US Department of Health and Human Services, NIH publication No. 91-3242 (1991)
The sequences above correspond to residues 99-110 of SEQ ID NO: 45 (IgG1), residues 99-107 of SEQ ID NO: 47 (IgG4), and residues 108-115 of SEQ ID NO: 46 (IgG2).

FIG. 1

```
          10         20         30         40         50         60
ASTKGPSVFP LAPSSKSTSG GTAALGCLVK DYFPEPVTVS WNSGALTSGV HTFPAVLQSS
                                ←CH1 Upper/Lower Hinge→        CH2→

70         80         90        100        110        120
GLYSLSSVVT VPSSSLGTQT YICNVNHKPS NTKVDKKVEP KSCDKTHTCP PCPAPELLGG 130        140        150        160        170        180
PSVFLFPPKP KDTLMISRTP EVTCVVVDVS HEDPEVKFNW YVDGVEVHNA KTKPREEQYN
                                                  CH3→

190        200        210        220        230        240
STYRVVSVLT VLHQDWLNGK EYKCKVSNKA LPAPIEKTIS KAKGQPREPQ VYTLPPSRDE 250        260        270        280        290        300
LTKNQVSLTC LVKGFYPSDI AVEWESNGQP ENNYKTTPPV LDSDGSFFLY SKLTVDKSRW 310        320        330
QQGNVFSCSV MHEALHNHYT QKSLSLSPGK
```

Human IGHG1 heavy chain constant region
UniProtKB/Swiss-Prot Accn. No. P01857
(SEQ ID NO:45)

FIG. 2

```
         10         20         30         40         50         60
ASTKGPSVFP LAPCSRSTSE STAALGCLVK DYFPEPVTVS WNSGALTSGV HTFPAVLQSS

←―CH1 Upper/Lower Hinge―→CH2―→
         70         80         90        100        110        120
GLYSLSSVVT VPSSNFGTQT YTCNVDHKPS NTKVDKTVER KCCVECPPCP APPVAGPSVF 130        140        150        160        170        180
LFPPKPKDTL MISRTPEVTC VVVDVSHEDP EVQFNWYVDG VEVHNAKTKP REEQFNSTFR CH3―→
        190        200        210        220        230        240
VVSVLTVVHQ DWLNGKEYKC KVSNKGLPAP IEKTISKTKG QPREPQVYTL PPSREEMTKN 250        260        270        280        290        300
QVSLTCLVKG FYPSDISVEW ESNGQPENNY KTTPPMLDSD GSFFLYSKLT VDKSRWQQGN 310        320
VFSCSVMHEA LHNHYTQKSL SLSPGK
```

Human IGHG2 heavy chain constant region
UniProtKB/Swiss-Prot Accn. No. P01859
(SEQ ID NO:46)

FIG. 3

```
         10         20         30         40         50         60
ASTKGPSVFP LAPCSRSTSE STAALGCLVK DYFPEPVTVS WNSGALTSGV HTFPAVLQSS

← CH1 Upper/Lower Hinge → CH2 →
         70         80         90        100        110        120
GLYSLSSVVT VPSSSLGTKT YTCNVDHKPS NTKVDKRVES KYGPPCPSCP APEFLGGPSV 130        140        150        160        170        180
FLFPPKPKDT LMISRTPEVT CVVVDVSQED PEVQFNWYVD GVEVHNAKTK PREEQFNSTY CH3 →
        190        200        210        220        230        240
RVVSVLTVLH QDWLNGKEYK CKVSNKGLPS SIEKTISKAK GQPREPQVYT LPPSQEEMTK 250        260        270        280        290        300
NQVSLTCLVK GFYPSDIAVE WESNGQPENN YKTTPPVLDS DGSFFLYSRL TVDKSRWQEG 310        320
NVFSCSVMHE ALHNHYTQKS LSLSLGK
```

Human IGHG4 heavy chain constant region
UniProtKB/Swiss-Prot Accn. No. P01861
(SEQ ID NO:47)

FIG. 4

Ab1 or Control-Treatment of NSG mice implanted with Raji tumor cells and PBMCs

Ab1-Treatment of NSG mice implanted with Raji tumor cells - no PBMC control
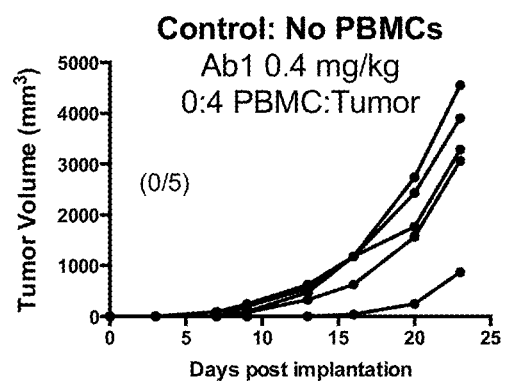
FIG. 7D
Ab1-Treatment NSG mice implanted with Raji tumor cells and PBMCs
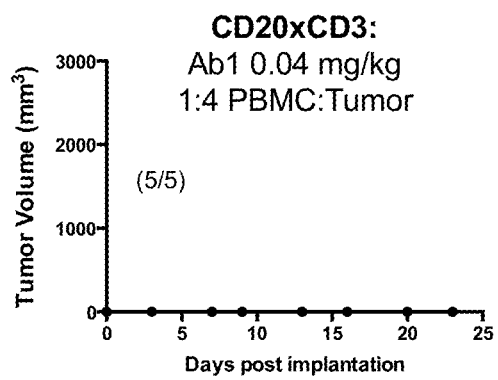 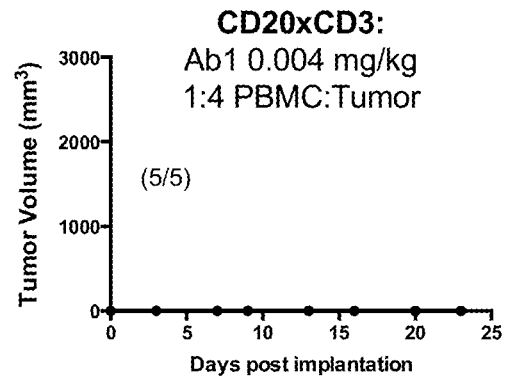
FIG. 7E      FIG. 7F

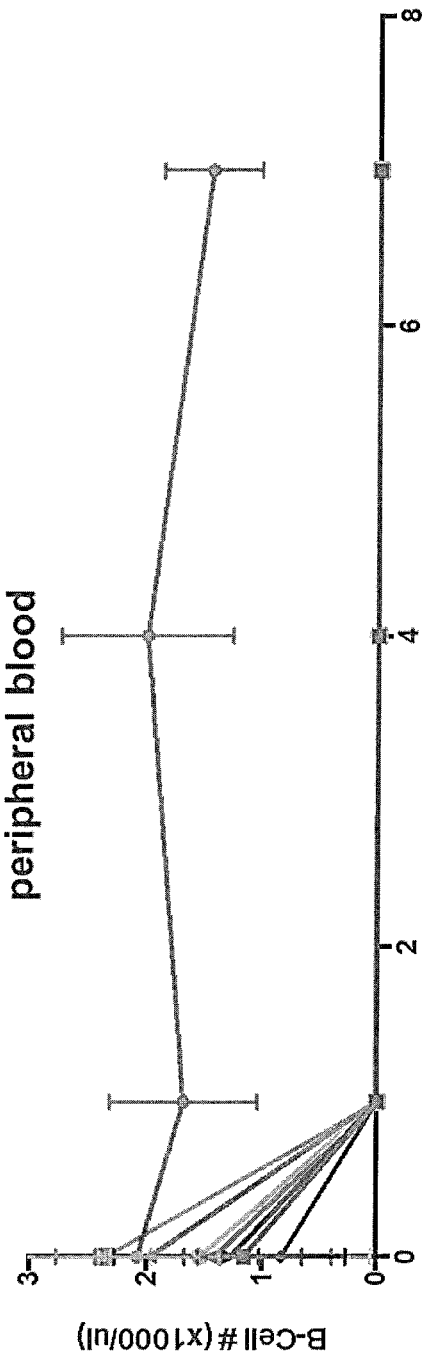
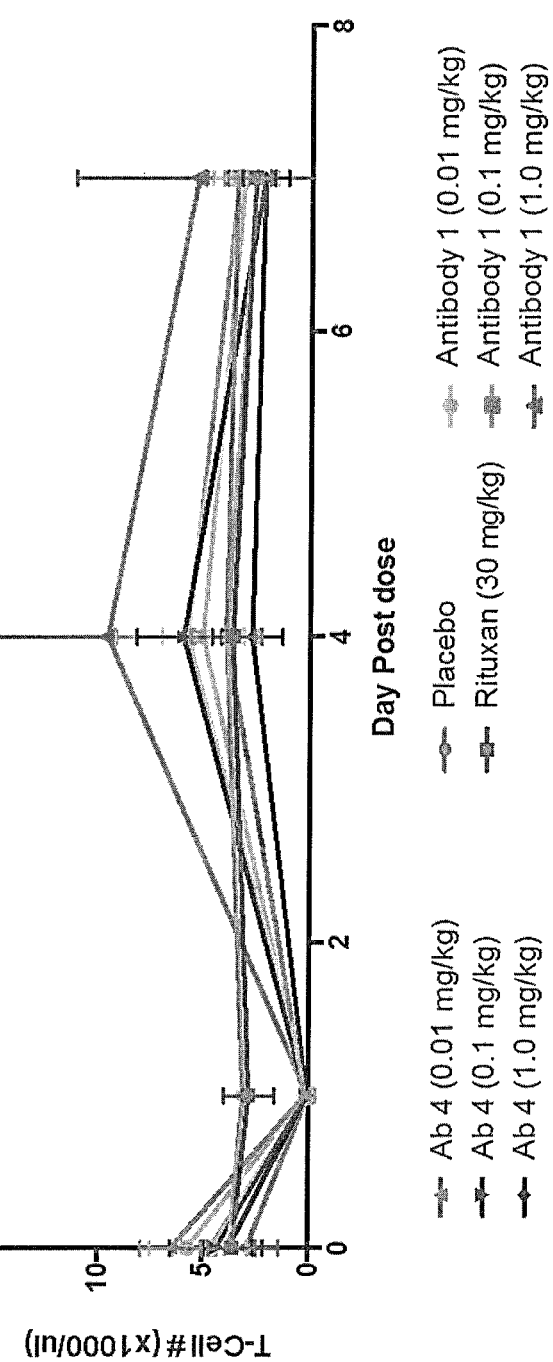
Fig. 11A
Fig. 11B

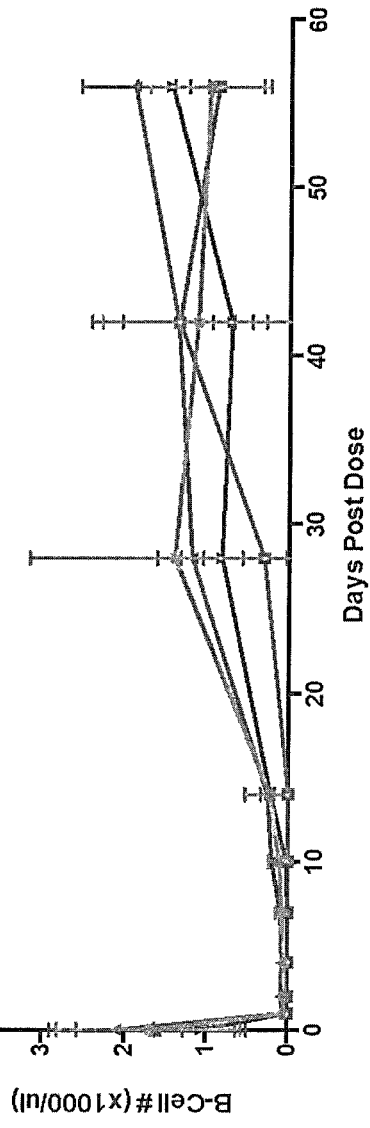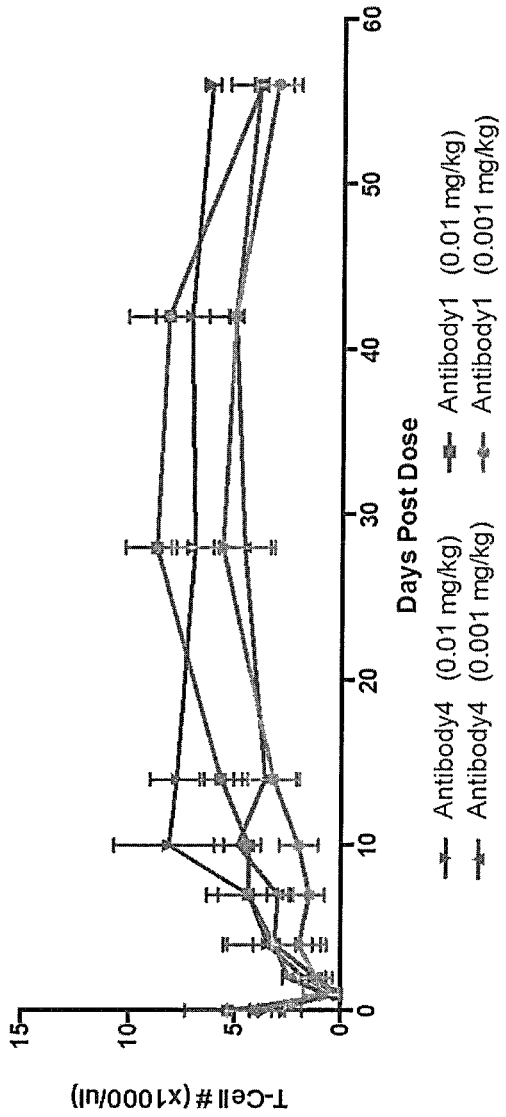
Fig. 13A
Fig. 13B

CD3xCD20 Bispecifics induce proliferation of T-cells *in vitro*

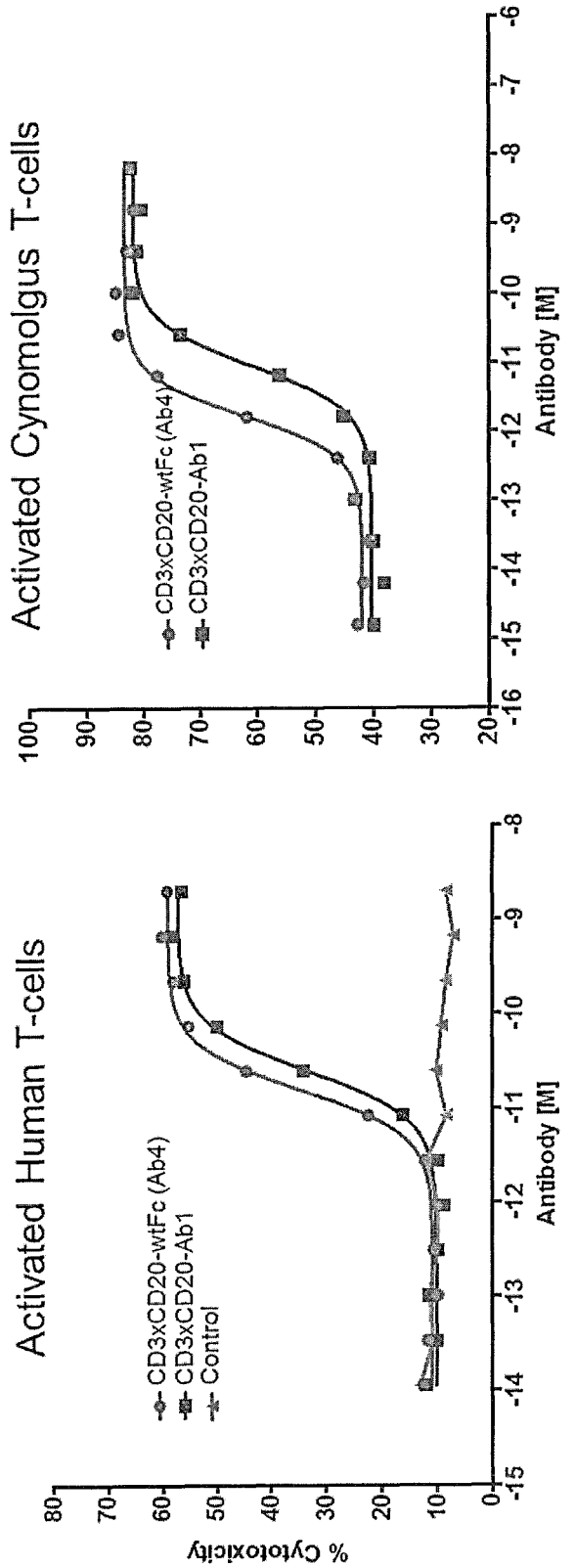

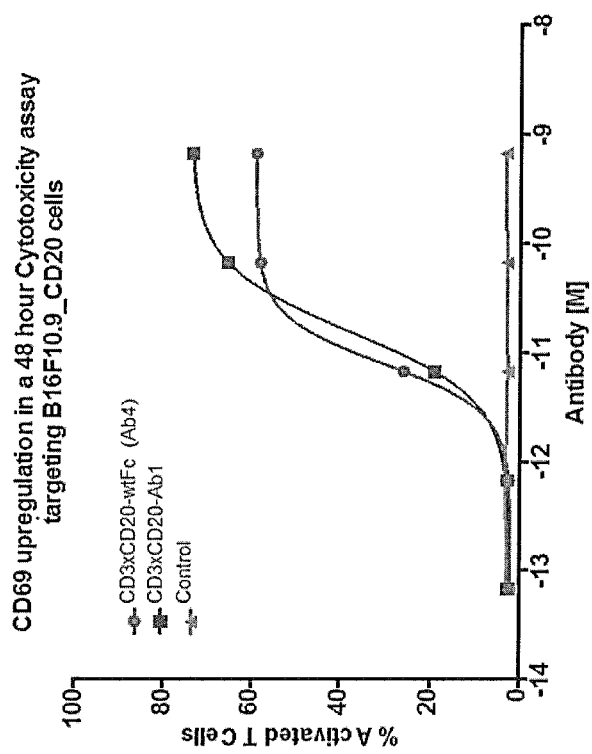

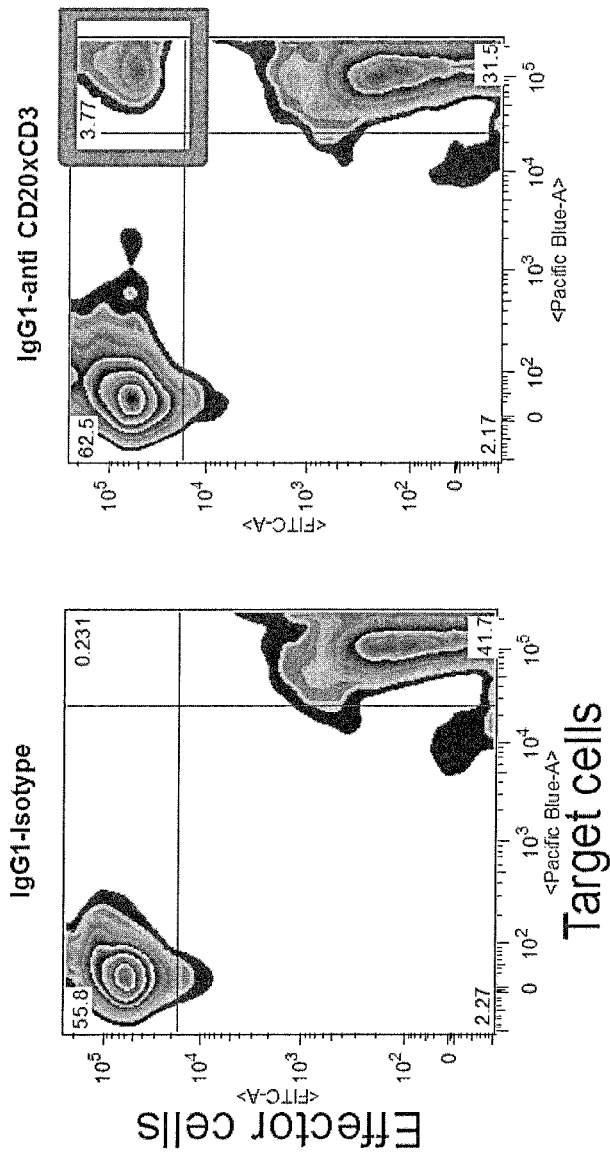

METHODS AND ANTIBODY COMPOSITIONS FOR TUMOR TREATMENT

CROSS-REFERENCE TO RELATED APPLICATIONS

This application claims the benefit under 35 USC 119(e) of U.S. Provisional Application Nos. 61/955,663, filed Mar. 19, 2014; 61/981,641, filed Apr. 18, 2014; 62/007,385, filed Jun. 3, 2014; and 62/033,460, filed Aug. 5, 2014. Each of these applications is incorporated herein by reference in its entirety for all purposes.

SEQUENCE LISTING

This application includes a sequence listing in computer readable form in a file named A0015US01-Sequence.txt created on Mar. 4, 2015 (83,454 bytes), which is incorporated by reference herein.

FIELD OF THE INVENTION

The present invention relates to bispecific antibodies, targeting CD20 and CD3 antigens, and methods of tumor killing. The present invention also relates to methods of reducing and/or controlling the effector functions that may result from Fc binding in association with antibody therapies for tumor treatment.

BACKGROUND

Dual targeting antibody strategies are being applied to complex diseases where multifactorial modulation aims to improve therapeutic efficacy. CD20 is a non-glycosylated phosphoprotein expressed on the cell membranes of mature B cells. CD20 is considered a B cell tumor-associated antigen because it is expressed by more than 95% of B-cell non-Hodgkin lymphomas (NHLs) and other B-cell malignancies, but it is absent on precursor B-cells, dendritic cells and plasma cells. Methods for treating cancer by targeting CD20 are known in the art. For example, the chimeric anti-CD20 monoclonal antibody rituximab has been used or suggested for use in treating cancers such as NHL, chronic lymphocytic leukemia (CLL) and small lymphocytic lymphoma (SLL). Anti-CD20 antibodies are believed to kill CD20-expressing tumor cells by complement dependent cytotoxicity (CDC), antibody-dependent cell mediated cytotoxicity (ADCC) and/or induction of apoptosis and sensitization to chemotherapy, although some patients have been shown to develop resistance to or exhibit incomplete responses to anti-CD20 therapy (e.g., resistance to rituximab).

CD3 is a homodimeric or heterodimeric antigen expressed on T cells in association with the T cell receptor complex (TCR) and is required for T cell activation. Functional CD3 is formed from the dimeric association of two of four different chains: epsilon, zeta, delta and gamma. Bispecific antibodies that are capable of binding CD3 and a target antigen, such as CD20, have been proposed for therapeutic uses involving targeting T cell immune responses to tissues and cells expressing the target antigen.

A bispecific antibody having a CD20-binding arm and a CD3-binding arm may provide the necessary crosstalk to augment antitumor activity. A third modality in such a bispecific antibody is the Fc domain. Modification of Fc binding properties may further augment the antitumor potency of a therapeutic antibody.

Binding of an immunoglobulin Fc domain to its receptor results in a variety of signaling and immune responses. These various "effector functions", such as CDC and ADCC, are the results of immunoglobulins of the G class (IgGs) forming a complex between the Fab domain of the IgG and a target antigen, whereas the Fc domain of the IgG binds to Fc receptors on effector cells. Some effector functions of IgG are independent of antigen binding and embody functions such as circulating serum levels and ability to transfer Ig across barriers. Other effector functions are considered essential for use in immunoglobulin therapies, such as cancer treatments. The ADCC mechanism in particular is considered to be one of the primary anti-tumor mechanisms of therapeutic antibodies already on the market such as rastuzumab (metastatic breast cancer) and rituximab (non-Hodgkin's lymphoma).

Current therapeutic strategies typically suggest that reduced effector functions (or reduced Fc gamma receptor binding) may be useful for antibodies whose aim is to neutralize or inhibit the biological activity of an antigen (e.g. antibody blockers or antagonists), or activate or initiate downstream cellular signalling (e.g. antibody agonists). However, the design of tumor targeting antibodies with reduced effector function is counterintuitive for tumor therapy, since it is expected that reduced cytotoxicity of target cells will not be efficacious to treat the disease, i.e. destroy tumor cells or inhibit tumor growth.

One strategy, described herein, utilizes differential Fc receptor binding combined with bispecific antigen binding to specifically target tumor markers as well as trigger tumor-specific T cell killing. The antibody's Fc domain is designed to carefully control Fc receptor binding to eliminate or reduce undesirable killing of cells like T cells, natural killer cells and macrophages bearing Fc receptors. A unique binding pattern with respect to Fc receptor interaction comprising FcγRII receptor binding interactions, but lacking FcγRI or FcγRIII interactions, has not been described in the art for a tumor-targeting Ig therapy.

Thus, the combination of bispecific B cell and T cell targeting antibodies with reduced binding to Fc receptors results in unexpectedly beneficial therapeutic properties. Bispecific antibodies that bind both CD3 and CD20 are especially useful in clinical settings in which specific CD20 targeting yet controlled and efficient cytotoxicity is desired.

BRIEF SUMMARY OF THE INVENTION

In a first aspect, the present invention provides bispecific antibodies with altered Fc binding domains that bind human CD3 and CD20. The antibodies according to this aspect of the invention are useful, inter alia, for targeting T cells expressing CD3, and for stimulating T cell activation, e.g., under circumstances where T cell-mediated killing is beneficial or desirable as part of a bispecific antibody that directs CD3-mediated T cell activation to specific cell types such as anti-CD20 tumor cells. The antibodies are further engineered to have specific effector functions that are not found in the immune system's natural repertoire.

Exemplary anti-CD3/CD20 antibodies of the present invention are listed in Tables 1 to 8 herein. Table 1 sets forth the amino acid sequence identifiers of the heavy chain variable regions (HCVRs) and light chain variable regions (LCVRs), as well as heavy chain complementarity determining regions (HCDR1, HCDR2 and HCDR3), and light chain complementarity determining regions (LCDR1, LCDR2 and LCDR3) of the exemplary bispecific antibodies. Table 2 sets forth the sequence identifiers of the nucleic acid molecules encoding the HCVRs, LCVRs, HCDR1, HCDR2 HCDR3, LCDR1, LCDR2 and LCDR3 of the exemplary bispecific antibodies. Table 3 sets forth the amino acid sequence identifier combinations of the exemplary bispecific antibodies including HCVR, heavy chain constant region (CH) and LCVR combinations. Table 4 sets forth the nucleic acid sequence identifiers the combinations of nucleic acid molecules encoding the HCVR, heavy chain constant region (CH) and LCVR combinations of the exemplary bispecific antibodies.

Table 5 describes the amino acid sequence identifiers for the heavy chain examples of the invention, wherein the bispecific antibody comprises an HCVR comprising a HCDR1, HCDR2 and HCDR3 of Table 5 paired with a CH of the invention. Table 6 separately describes the amino acid sequence identifiers for the light chain examples of the invention, wherein the bispecific antibody comprises an LCVR comprising an LCDR1, LCDR2 and LCDR3 of Table 6.

The present invention provides antibodies, or antigen-binding fragments thereof, comprising an HCVR comprising an amino acid sequence selected from HCVR amino acid sequences listed in Table 1, or a substantially similar sequence thereof having at least 90%, at least 95%, at least 98% or at least 99% sequence identity thereto.

The present invention also provides antibodies, or antigen-binding fragments thereof, comprising an LCVR comprising an amino acid sequence selected from the LCVR amino acid sequence listed in Table 1, or a substantially similar sequence thereof having at least 90%, at least 95%, at least 98% or at least 99% sequence identity thereto.

The present invention also provides antibodies, or antigen-binding fragments thereof, comprising an HCVR and an LCVR amino acid sequence pair (HCVR/LCVR) comprising an amino acid sequence pair contained within the exemplary anti-CD3/CD20 antibodies listed in Table 1. In certain embodiments, the HCVR/LCVR amino acid sequence pair is selected from the group consisting of SEQ ID NOs: 2/18 and 10/18 (e.g., Antibody 1 and Antibody 2).

The present invention also provides antibodies, or antigen-binding fragments thereof, comprising a heavy chain CDR1 (HCDR1) comprising an amino acid sequence selected from the HCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR2 (HCDR2) comprising an amino acid sequence selected from the HCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a heavy chain CDR3 (HCDR3) comprising an amino acid sequence selected from the HCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR1 (LCDR1) comprising an amino acid sequence selected from the LCDR1 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR2 (LCDR2) comprising an amino acid sequence selected from the LCDR2 amino acid sequences listed in Table 1 or a substantially similar sequence thereof having at least 90%, at least 95%, at least 98% or at least 99% sequence identity.

The present invention also provides antibodies, or antigen-binding fragments thereof, comprising a light chain CDR3 (LCDR3) comprising an amino acid sequence selected from the LCDR3 amino acid sequences listed in Table 1 or a substantially similar sequence thereof having at least 90%, at least 95%, at least 98% or at least 99% sequence identity.

The present invention also provides antibodies, or antigen-binding fragments thereof, comprising an HCDR3 and an LCDR3 amino acid sequence pair (HCDR3/LCDR3) comprising the HCDR3 amino acid sequences listed in Table 1 paired with any of the LCDR3 amino acid sequences listed in Table 1, such as the HCDR3/LCDR3 amino acid sequence pair selected from the group consisting of SEQ ID NOs: 8/16 (e.g., Antibody 1 or Antibody 2).

The present invention also provides antibodies, or antigen-binding fragments thereof, comprising a set of six CDRs (i.e., HCDR1-HCDR2-HCDR3-LCDR1-LCDR2-LCDR3) contained in Table 1. In certain embodiments, the HCDR1-HCDR2-HCDR3-LCDR1-LCDR2-LCDR3 set of amino acid sequences is SEQ ID NOs: 4-6-8-20-22-24; or 12-14-16-20-22-24 (e.g., Antibody 1 or Antibody 2).

In a related embodiment, the present invention provides antibodies, or antigen-binding fragments thereof, comprising a set of six CDRs (i.e., HCDR1-HCDR2-HCDR3-LCDR1-LCDR2-LCDR3) contained within an HCVR/LCVR amino acid sequence pair as defined the exemplary antibodies listed in Table 1. For example, the present invention includes antibodies, or antigen-binding fragments thereof, comprising the HCDR1-HCDR2-HCDR3-LCDR1-LCDR2-LCDR3 amino acid sequences set contained within an HCVR/LCVR amino acid sequence pair selected from the group consisting of SEQ ID NO: 2/18 (e.g., Antibody 1 or Antibody 2). Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding the antibodies or portions thereof, for example, the present invention provides nucleic acid molecules encoding the HCVR or LCVR amino acid sequences listed in Table 1; in certain embodiments the nucleic acid molecule comprises a polynucleotide sequence selected from the HCVR/LCVR nucleic acid sequences listed in Table 2, or a substantially similar sequence thereof having at least 90%, at least 95%, at least 98% or at least 99% sequence identity thereto.

The present invention also provides nucleic acid molecules encoding the HCDR1 or HCDR2 or HCDR3 amino acid sequences listed in Table 1; in certain embodiments the nucleic acid molecule comprises a polynucleotide sequence selected from any of the HCDR1 or HCDR2 or HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 or LCDR2 or LCDR3 amino acid sequences listed in Table 1; in certain embodiments the nucleic acid molecule comprises a polynucleotide sequence selected from any of the LCDR1 or LCDR2 or LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined the exemplary anti-CD3 antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-CD3 antibodies listed in Table 1.

The present invention also provides nucleic acid molecules encoding both an HCVR and an LCVR, wherein the HCVR comprises an amino acid sequence of the HCVR amino acid sequences listed in Table 1, and wherein the LCVR comprises an amino acid sequence of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-CD3 antibody listed in Table 1.

The present invention also provides antibodies, or antigen-binding fragments thereof, comprising a heavy chain constant region (CH) comprising an amino acid sequence selected from the CH amino acid sequences listed in Table 2 or a substantially similar sequence thereof having at least 90%, at least 95%, at least 98% or at least 99% sequence identity.

The present invention also provides antibodies, or antigen-binding fragments thereof, comprising a heavy chain constant region (CH) encoded by nucleic acid sequence selected from the CH nucleic acid sequences listed in Table 2 or a substantially similar sequence thereof having at least 90%, at least 95%, at least 98% or at least 99% sequence identity.

The present invention also provides recombinant expression vectors capable of expressing a polypeptide comprising a heavy or light chain variable region of an anti-CD3 antibody and a heavy or light chain variable region of an anti-CD20 antibody. For example, the present invention includes recombinant expression vectors comprising any of the nucleic acid molecules mentioned above, i.e., nucleic acid molecules encoding any of the HCVR, LCVR, and/or CDR sequences, and/or CH sequences as set forth in Table 1 and Table 2. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

In another aspect, the invention provides a therapeutically effective amount of a recombinant human antibody or fragment thereof which specifically binds CD3 and CD20, wherein the antibody comprises a chimeric Fc domain, and a pharmaceutically acceptable carrier. In a related aspect, the invention features a composition which is a combination of an anti-CD3/CD20 antibody and a second therapeutic agent. In one embodiment, the second therapeutic agent is any agent that is advantageously combined with an anti-CD3/CD20 antibody. Exemplary agents that may be advantageously combined with an anti-CD3/CD20 antibody include, without limitation, other agents that bind and/or activate CD3 signaling (including other antibodies or antigen-binding fragments thereof, etc.) and/or agents which do not directly bind CD3 but nonetheless activate or stimulate immune cell activation, or enhance tumor killing. Additional combination therapies and co-formulations involving the anti-CD3 antibodies of the present invention are disclosed elsewhere herein.

According to another aspect, the present invention provides bispecific antigen-binding molecules that bind CD3 and a target antigen, wherein the molecule comprises a chimeric Fc domain having reduced effector function. In certain embodiment the molecule comprises a chimeric Fc domain as described herein. According to certain exemplary embodiments, the bispecific antigen-binding molecules bind CD3 and CD20; such bispecific antigen-binding molecules are also referred to herein as "anti-CD3/anti-CD20 bispecific molecules." The anti-CD20 portion of the anti-CD3/anti-CD20 bispecific molecule is useful for targeting tumor cells that express CD20 (e.g., B-cell tumors), and the anti-CD3 portion of the bispecific molecule is useful for activating T-cells. The simultaneous binding of CD20 on a tumor cell and CD3 on a T-cell mediates directed killing (cell lysis) of the targeted tumor cell by the activated T-cell and facilitated by effector cells that bind the chimeric Fc domain. The anti-CD3/anti-CD20 bispecific molecules of the invention are therefore useful, inter alia, for treating diseases and disorders related to or caused by CD20-expressing tumors (e.g., lymphomas and melanoma tumors).

The anti-CD3/anti-CD20 bispecific molecules of the invention further provide a method for regression of CD20-positive tumors. The invention therefore provides a method of treating a B cell cancer in a subject, the method comprising administering a therapeutic amount of anti-CD3/anti-CD20 bispecific molecules of the invention wherein the amount is sufficient to reduce tumor burden, produce tumor regression, or reduce tumor development in the subject.

The anti-CD3/anti-CD20 bispecific molecules of the invention further provide a method for suppression or regression of CD20-positive (i.e. CD20-expressing) melanoma. The invention therefore provides a method of treating CD20-positive melanoma in a subject, the method comprising administering a therapeutic amount of anti-CD3/anti-CD20 bispecific molecules of the invention wherein the amount is sufficient to inhibit tumor growth, reduce tumor burden, or reduce tumor development in the subject.

In another aspect, the present invention provides for use of a bispecific antibody for treating or ameliorating cancer in a subject, wherein the bispecific antibody comprises a first antigen-binding domain that binds human CD3, a second antigen-binding domain that binds human CD20, and a chimeric Fc domain tethered to each of the first and second antigen-binding domains, and the treating or ameliorating cancer comprises: (a) suppressing tumor growth in the subject, (b) mediating B-cell lysis in the subject, (c) treating a B-cell cancer in the subject, (d) treating cancer that is positive for CD20 expression in the subject, or (e) treating CD20-expressing melanoma cancer in the subject.

In another aspect, the present invention provides for use of a bispecific antibody for suppressing tumor growth in a subject, wherein the bispecific antibody comprises a first antigen-binding domain that binds human CD3, a second antigen-binding domain that binds human CD20, and a chimeric Fc domain tethered to each of the first and second antigen-binding domains. In some cases, suppressing tumor growth comprises (a) inhibiting growth of tumors in the subject, (b) decreasing the size of tumor(s) in the subject, or (c) decreasing the number of tumors in the subject.

In another aspect, the present invention provides for use of a bispecific antibody for mediating B-cell lysis in a subject, wherein the bispecific antibody comprises a first antigen-binding domain that binds human CD3, a second antigen-binding domain that binds human CD20, and a chimeric Fc domain tethered to each of the first and second antigen-binding domains. In some cases the B-cells are pre-B lymphocytes, mature B-lymphocytes, or B-cell non-Hodgkin's lymphoma cells.

In another aspect, the present invention provides for use of a bispecific antibody for treating a B-cell cancer in a subject, wherein the bispecific antibody comprises a first antigen-binding domain that binds human CD3, a second antigen-binding domain that binds human CD20, and a chimeric Fc domain tethered to each of the first and second antigen-binding domains. In some cases, the B-cell cancer is selected from the group consisting of: follicular lymphoma, B-cell chronic lymphocytic leukemia, B-cell lymphoblastic lymphoma, Hodgkin lymphoma, Non-Hodgkin's lymphoma, diffuse large B-cell lymphoma, marginal zone lymphoma, Mantle cell lymphoma, hairy cell leukemia and Burkitt lymphoma. In some cases, the subject is afflicted with a tumor that is resistant to, or incompletely responsive to (a) anti-CD20 monospecific therapy alone, or (b) rituximab monotherapy. In some cases, the subject has received an anti-CD20 monospecific antibody therapy at least 1 day to 1 year prior to the administration of the bispecific antibody. In some cases, the anti-CD20 monospecific therapy comprises or consists of an anti-CD20 monospecific antibody. In some cases, the anti-CD20 monospecific antibody is rituximab.

In another aspect, the present invention provides for use of a bispecific antibody for treating a B-cell cancer in a subject, comprising: (a) selecting a subject who is afflicted with a cancer that is resistant to, or incompletely responsive to anti-CD20 monospecific therapy alone; and (b) administering to the subject a therapeutic amount of a bispecific antibody comprising a first antigen-binding domain that binds human CD3, a second antigen-binding domain that binds human CD20, and a chimeric Fc domain tethered to each of the first and second antigen-binding domains.

In some cases, the subject is selected on the basis of having a tumor that is resistant to, refractory to, or incompletely responsive to anti-CD20 monospecific therapy. In some cases, the anti-CD20 monospecific therapy comprises or consists of an anti-CD20 monospecific antibody. In some cases, the anti-CD20 monospecific antibody is rituximab. In some cases, the B-cell cancer is lymphoma. In some cases, the lymphoma is Non-Hodgkin's Lymphoma (NHL). In some cases, the B-cell cancer is Chronic Lymphocytic Leukemia (CLL).

In another aspect, the present invention provides for use of a bispecific antibody for treating a B cell cancer in a subject, wherein the bispecific antibody comprises a first antigen-binding domain that binds human CD3, a second antigen-binding domain that binds human CD20, and a chimeric Fc domain tethered to each of the first and second antigen-binding domains, and wherein the bispecific antibody is administered in an amount sufficient to reduce tumor burden, produce tumor regression, inhibit tumor growth or reduce tumor development in the subject.

In some cases, the B-cell cancer is selected from the group consisting of: follicular lymphoma, B-cell chronic lymphocytic leukemia, B-cell lymphoblastic lymphoma, Hodgkin lymphoma, Non-Hodgkin's lymphoma, diffuse large B-cell lymphoma, marginal zone lymphoma, Mantle cell lymphoma, hairy cell leukemia and Burkitt lymphoma. In some cases, the subject is afflicted with a tumor that is resistant to, or incompletely responsive to anti-CD20 monospecific therapy alone. In some cases, the subject is afflicted with a tumor that is resistant to, or incompletely responsive to rituximab monotherapy. In some cases, the subject has received an anti-CD20 monospecific antibody therapy at least 1 day to 1 year prior to the administration of the bispecific antibody. In some cases, the anti-CD20 monospecific therapy comprises or consists of an anti-CD20 monospecific antibody. In some cases, the anti-CD20 monospecific antibody is rituximab. In some cases, the amount is sufficient to reduce tumor burden, produce tumor regression, inhibit tumor growth or reduce tumor development in the subject is between about 0.001 mg/kg to about 1 mg/kg. In some cases, the amount is sufficient to reduce tumor burden, produce tumor regression, or reduce tumor development in the subject is about 0.4 mg/kg.

In another aspect, the present invention provides for use of a bispecific antibody for treating cancer that is positive for CD20 expression in a subject, comprising: (a) selecting a subject who is afflicted with a cancer and/or tumors; (b) collecting one or more biological samples from the subject; (c) identifying CD20-expressing cancer or tumor cells in the one or more samples; and (b) administering to the subject a therapeutic amount of a bispecific antibody comprising a first antigen-binding domain that binds human CD3, a second antigen-binding domain that binds human CD20, and a chimeric Fc domain tethered to each of the first and second antigen-binding domains.

In some cases, the subject is selected on the basis of having cancer or a tumor that is resistant to, refractory to, or incompletely responsive to anti-CD20 therapy. In some cases, the subject is selected on the basis of having a residual cancer. In some cases, the anti-CD20 therapy comprises or consists of an anti-CD20 monospecific antibody. In some cases, the anti-CD20 monospecific antibody is rituximab. In some cases, the cancer is lymphoma or leukemia. In some cases, the lymphoma is selected form the group consisting of follicular lymphoma, B-cell lymphoblastic lymphoma, Hodgkin lymphoma, Non-Hodgkin's lymphoma, diffuse large B-cell lymphoma, marginal zone lymphoma, Mantle cell lymphoma, hairy cell leukemia and Burkitt lymphoma. In some cases, the leukemia is B-cell chronic lymphocytic leukemia (CLL).

In another aspect, the present invention provides for use of a bispecific antibody for treating CD20-expressing melanoma cancer in a subject, comprising administering a therapeutic amount of a bispecific antibody comprising a first antigen-binding domain that binds human CD3, a second antigen-binding domain that binds human CD20, and a chimeric Fc domain tethered to each of the first and second antigen-binding domains, wherein the amount is sufficient to reduce tumor burden, inhibit tumor growth or reduce tumor development in the subject.

The bispecific antigen-binding molecules according to this aspect of the present invention comprise a first antigen-binding domain that specifically binds human CD3, and a second antigen-binding domain that specifically binds CD20, and a chimeric Fc domain. The present invention includes anti-CD3/anti-CD20 bispecific molecules (e.g., bispecific antibodies) wherein each antigen-binding domain comprises a heavy chain variable region (HCVR) paired with a light chain variable region (LCVR). In certain exemplary embodiments of the invention, the anti-CD3 antigen-binding domain and the anti-CD20 antigen binding domain each comprise different, distinct HCVRs paired with a common LCVR. For example, as illustrated in Example 2 herein, bispecific antibodies were constructed comprising a first antigen-binding domain that specifically binds CD3, wherein the first antigen-binding domain comprises an HCVR/LCVR pair derived from an anti-CD3 antibody; and a second antigen-binding domain that specifically binds CD20, wherein the second antigen-binding domain comprises an HCVR derived from an anti-CD20 antibody paired with an LCVR derived from an anti-CD3 antibody (e.g., the same LCVR that is included in the anti-CD3 antigen-binding domain). In other words, in the exemplary molecules disclosed herein, the pairing of an HCVR from an anti-CD20 antibody with an LCVR from an anti-CD3 antibody creates an antigen-binding domain that specifically binds CD20 (but does not bind CD3). In such embodiments, the first and second antigen-binding domains comprise distinct anti-CD3 and anti-CD20 HCVRs but share a common anti-CD3 LCVR.

The present invention provides anti-CD3/anti-CD20 bispecific molecules, wherein the first antigen-binding domain that specifically binds CD3 comprises any of the HCVR amino acid sequences as set forth in Table 1 or Table 2. The first antigen-binding domain that specifically binds CD3 may also comprise any of the LCVR amino acid sequences as set forth in Table 1 or Table 2. According to certain embodiments, the first antigen-binding domain that specifically binds CD3 comprises any of the HCVR/LCVR amino acid sequence pairs as set forth in Table 1 or Table 2. The present invention also provides anti-CD3/anti-CD20 bispecific molecules, wherein the first antigen-binding domain that specifically binds CD3 comprises any of the heavy chain CDR1-CDR2-CDR3 amino acid sequences as set forth in Table 1 or Table 2, and/or any of the light chain CDR1-CDR2-CDR3 amino acid sequences as set forth in Table 1 or Table 2.

According to certain embodiments, the present invention provides anti-CD3/anti-CD20 bispecific molecules, wherein the first antigen-binding domain that specifically binds CD3 comprises a heavy chain variable region (HCVR) having an amino acid sequence comprising SEQ ID NO: 10 or a substantially similar sequence thereof having at least 90%, at least 95%, at least 98% or at least 99% sequence identity.

The present invention also provides anti-CD3/anti-CD20 bispecific molecules, wherein the first antigen-binding domain that specifically binds CD3 comprises a light chain variable region (LCVR) having an amino acid sequence comprising SEQ ID NO: 18, or a substantially similar sequence thereof having at least 90%, at least 95%, at least 98% or at least 99% sequence identity.

The present invention also provides anti-CD3/anti-CD20 bispecific molecules, wherein the first antigen-binding domain that specifically binds CD3 comprises a HCVR and LCVR (HCVR/LCVR) amino acid sequence pair selected from the group consisting of SEQ ID NO: 10/18.

The present invention also provides anti-CD3/anti-CD20 bispecific molecules, wherein the first antigen-binding domain that specifically binds CD3 comprises a heavy chain CDR3 (HCDR3) domain having an amino acid sequence comprising SEQ ID NO: 16, or a substantially similar sequence thereto having at least 90%, at least 95%, at least 98% or at least 99% sequence identity; and a light chain CDR3 (LCDR3) domain having an amino acid sequence comprising SEQ ID NO: 24, or a substantially similar sequence thereof having at least 90%, at least 95%, at least 98% or at least 99% sequence identity.

In certain embodiments, the first antigen-binding domain that specifically binds CD3 comprises a HCDR3/LCDR3 amino acid sequence pair comprising SEQ ID NOs: 16/24.

The present invention also provides anti-CD3/anti-CD20 bispecific antigen-binding molecules, wherein the first antigen-binding domain that specifically binds CD3 comprises a heavy chain CDR1 (HCDR1) domain having an amino acid sequence comprising SEQ ID NO: 12, or a substantially similar sequence thereof having at least 90%, at least 95%, at least 98% or at least 99% sequence identity; a heavy chain CDR2 (HCDR2) domain having an amino acid sequence comprising SEQ ID NO: 14, or a substantially similar sequence thereof having at least 90%, at least 95%, at least 98% or at least 99% sequence identity; a light chain CDR1 (LCDR1) domain having an amino acid sequence comprising SEQ ID NO: 20, or a substantially similar sequence thereof having at least 90%, at least 95%, at least 98% or at least 99% sequence identity; and a light chain CDR2 (LCDR2) domain having an amino acid sequence comprising SEQ ID NO: 22, or a substantially similar sequence thereof having at least 90%, at least 95%, at least 98% or at least 99% sequence identity.

Certain non-limiting, exemplary anti-CD3/anti-CD20 bispecific antigen-binding molecules of the invention include a first antigen-binding domain that specifically binds CD3 comprising HCDR1-HCDR2-HCDR3-LCDR1-LCDR2-LCDR3 domains, respectively, having the amino acid sequences selected from the group consisting of: SEQ ID NO: 12-14-16-20-22-24.

The present invention also provides anti-CD3/anti-CD20 bispecific molecules, wherein the second antigen-binding domain that specifically binds CD20 comprises a heavy chain variable region (HCVR) having the amino acid sequence comprising SEQ ID NO: 2, or a substantially similar sequence thereof having at least 90%, at least 95%, at least 98% or at least 99% sequence identity.

The present invention also provides anti-CD3/anti-CD20 bispecific molecules, wherein the second antigen-binding domain that specifically binds CD20 comprises a light chain variable region (LCVR) having the amino acid sequence comprising SEQ ID NO: 18 or a substantially similar sequence thereof having at least 90%, at least 95%, at least 98% or at least 99% sequence identity. The present invention also provides anti-CD3/anti-CD20 bispecific molecules, wherein the second antigen-binding domain that specifically binds CD20 comprises a light chain variable region (LCVR) having the amino acid sequence comprising SEQ ID NO: 75 or a substantially similar sequence thereof having at least 90%, at least 95%, at least 98% or at least 99% sequence identity.

The present invention also provides anti-CD3/anti-CD20 bispecific molecules, wherein the second antigen-binding domain that specifically binds CD20 comprises a HCVR and LCVR (HCVR/LCVR) amino acid sequence pair comprising SEQ ID NO: 2/18, or SEQ ID NO: 2/75.

The present invention also provides anti-CD3/anti-CD20 bispecific molecules, wherein the second antigen-binding domain that specifically binds CD20 comprises a heavy chain CDR3 (HCDR3) domain having the amino acid sequence of SEQ ID NO: 8, or a substantially similar sequence thereto having at least 90%, at least 95%, at least 98% or at least 99% sequence identity; and a light chain CDR3 (LCDR3) domain having an amino acid sequence comprising SEQ ID NO: 24, or a substantially similar sequence thereof having at least 90%, at least 95%, at least 98% or at least 99% sequence identity.

In certain embodiments, the second antigen-binding domain that specifically binds CD20 comprises a HCDR3/LCDR3 amino acid sequence pair comprising SEQ ID NO: 8/24.

The present invention also provides anti-CD3/anti-CD20 bispecific antigen-binding molecules, wherein the second antigen-binding domain that specifically binds CD20 comprises a heavy chain CDR1 (HCDR1) domain having the amino acid sequence of SEQ ID NO: 4, or a substantially similar sequence thereof having at least 90%, at least 95%, at least 98% or at least 99% sequence identity; a heavy chain CDR2 (HCDR2) domain having the amino acid sequence of SEQ ID NO: 6, or a substantially similar sequence thereof having at least 90%, at least 95%, at least 98% or at least 99% sequence identity; a light chain CDR1 (LCDR1) domain having an amino acid sequence of SEQ ID NO: 20, or a substantially similar sequence thereof having at least 90%, at least 95%, at least 98% or at least 99% sequence identity; and a light chain CDR2 (LCDR2) domain having an amino acid sequence of SEQ ID NO: 22, or a substantially similar sequence thereof having at least 90%, at least 95%, at least 98% or at least 99% sequence identity.

Certain non-limiting, exemplary anti-CD3/anti-CD20 bispecific antigen-binding molecules of the invention include a second antigen-binding domain that specifically binds CD20 comprising HCDR1-HCDR2-HCDR3-LCDR1-LCDR2-LCDR3 domains, respectively, having the amino acid sequences selected from the group consisting of: SEQ ID NO: 4-6-8-20-22-24 (e.g. Antibody 1 or Antibody 2).

In one embodiment, the anti-CD3/anti-CD20 bispecific antigen-binding molecules of the invention include a first antigen-binding domain (A1) that specifically binds human CD3 and comprises three heavy chain complementarity determining regions (A1-HCDR1, A1-HCDR2, A1-HCDR3) and three light chain complementarity determining regions (A1-LCDR1, A1-LCDR2, A1-LCDR3), and a second antigen-binding domain (A2) that specifically binds human CD20 and comprises three heavy chain complementarity determining regions (A2-HCDR1, A2-HCDR2 and A2-HCDR3) and three light chain complementarity determining regions (A2-LCDR1, A2-LCDR2 and A2-LCDR3); wherein: (a) A1-HCDR1 comprises the amino acid sequence of SEQ ID NO: 12; (b) A1-HCDR2 comprises the amino acid sequence of SEQ ID NO: 14; (c) A1-HCDR3 comprises the amino acid sequence of SEQ ID NO: 16; (d) A1-LCDR1 comprises the amino acid sequence of SEQ ID NO: 20; (e) A1-LCDR2 comprises the amino acid sequence of SEQ ID NO: 22; (f) A1-LCDR3 comprises the amino acid sequence of SEQ ID NO: 24; (g) A2-HCDR1 comprises the amino acid sequence of SEQ ID NO: 4; (h) A2-HCDR2 comprises the amino acid sequence of SEQ ID NO: 6; (i) A2-HCDR3 comprises the amino acid sequence of SEQ ID NO: 8; (j) A2-LCDR1 comprises the amino acid sequence of SEQ ID NO: 20; (k) A2-LCDR2 comprises the amino acid sequence of SEQ ID NO: 22; and (l) A2-LCDR3 comprises the amino acid sequence of SEQ ID NO: 24.

In a related embodiment, the invention includes anti-CD3/anti-CD20 bispecific antigen-binding molecules wherein the second antigen-binding domain that specifically binds CD20 comprises the heavy and light chain CDR domains contained within heavy and light chain variable region (HCVR/LCVR) sequences of SEQ ID NOs: 2/18.

In another aspect, the present invention provides nucleic acid molecules encoding any of the HCVR, LCVR or CDR sequences of the anti-CD3/anti-CD20 bispecific antigen-binding molecules disclosed herein, including nucleic acid molecules comprising the polynucleotide sequences as set forth in Tables 2, 7 and 8 herein, as well as nucleic acid molecules comprising two of the polynucleotide sequences as set forth in Tables 2, 7 and 8 in any functional combination or arrangement thereof. Recombinant expression vectors carrying the nucleic acids of the invention, and host cells into which such vectors have been introduced, are also encompassed by the invention, as are methods of producing the antibodies by culturing the host cells under conditions permitting production of the antibodies, and recovering the antibodies produced.

The present invention includes anti-CD3/anti-CD20 bispecific antigen-binding molecules wherein any of the aforementioned antigen-binding domains that specifically bind CD3 is combined, connected or otherwise associated with any of the aforementioned antigen-binding domains that specifically bind CD20 to form a bispecific antigen-binding molecule that binds CD3 and CD20.

In another aspect, the invention provides a bispecific antibody comprising a first antigen-binding domain that binds human CD3, a second antigen-binding domain that binds human CD20, and a chimeric Fc domain tethered to each of the first and second antigen-binding domains. In a related aspect, the bispecific antibody is capable of specifically binding to human FcγRIIA and human FcγRIIB. The present invention provides anti-CD3/anti-CD20 bispecific antigen-binding molecules that preferentially bind to human FcγRIIA and human FcγRIIB and display little or no binding affinity to human FcγRI or human FcγRIII. In one aspect, the bispecific antibodies are capable of specifically binding to human FcγRIIA with a higher affinity than for binding to human FcγRIIB, human FcγRI, and/or human FcγRIII, as measured in an in vitro assay. The bispecific antibodies of the invention are capable of specifically binding to human FcγRIIA and human FcγRIIB at higher affinities than the antibodies bind to human FcγRI or human FcγRIII, as measured in an in vitro assay. In some embodiments, wherein the antibody specifically binds to both human FcγRIIA and human FcγRIIB, and exhibits less than 1 μM $K_D$ binding affinity to each of human FcγRI and human FcγRIII, as measured in an in vitro assay.

In other aspects, the invention provides a bispecific antibody comprising a first and second heavy chain polypeptide each comprising a chimeric Fc domain, wherein the first heavy chain polypeptide comprises an antigen-binding domain that binds human CD3, and wherein the second heavy chain polypeptide comprises a second antigen-binding domain that binds human CD20.

In other embodiments, the antibody exhibits a higher, i.e. stronger, binding affinity for human FcγRIIA relative to its binding human FcγRIIB, as measured in an in vitro assay. In still other embodiments, the antibody binds to human FcγRIIA and exhibits a lower $K_D$ value relative to its binding human FcγRIIB, as measured in an in vitro assay. In some embodiments, the antibody binds to the human FcγRIIA at 25° C. having a $K_D$ value between 10 and 30 μM, as measured in an in vitro assay. In some embodiments, the antibody binds to the human FcγRIIB at 25° C. having a $K_D$ value between 100 and 250 μM, as measured in an in vitro assay.

In another embodiment, the antibody exhibits little or no detectable binding affinity to human FcγRI, as measured in an in vitro assay. In some embodiments, the antibody exhibits little or no detectable binding affinity to human FcγRIII, as measured in an in vitro assay.

In some embodiments, the in vitro assay is a surface plasmon resonance assay.

In some embodiments, the antibody exhibits reduced antibody-dependent-cellular cytotoxicity (ADCC) compared to an antibody comprising a wild-type Fc domain, as measured in an in vitro cytotoxicity assay.

In some embodiments, the antibody exhibits negligible or no detectable antibody-dependent-cellular cytotoxicity (ADCC).

In some embodiments, the antibody exhibits decreased complement dependent cytotoxicity (CDC) compared to an antibody comprising a wild-type Fc domain, as measured in an in vitro cytotoxicity assay.

In some embodiments, the antibody exhibits less than 50% cytotoxicity, as determined by measurement of cell lysis in an in vitro assay.

In some embodiments, the antibody exhibits negligible or no detectable complement dependent cytotoxicity (CDC).

In some embodiments, the antibody induces decreased T cell-mediated killing of cells bearing Fc receptors, such as NK cells or macrophages, compared to an antibody comprising a wild-type Fc domain.

In certain embodiments, the antibody induces decreased killing of T-cells, mediated by Fc receptor-bearing cells such as NK cells or macrophages, compared to an antibody comprising a wild-type Fc domain.

In some embodiments, the antibody exhibits binding affinity to human FcγRIIA stronger than its binding affinity to human FcγRIIB, which is stronger than its binding affinity to human FcγRI, which is stronger than or equivalent to its binding affinity to human FcγRIII, as determined by measurement of the $K_D$ in an in vitro assay. In other embodiments, the antibody exhibits binding affinity to human FcγRIIA>human FcγRIIB>human FcγRI>=human FcγRIII, as measured in an in vitro assay.

In some embodiments, the antibody exhibits binding affinity to human FcγRIIA stronger than its binding affinity to human FcγRIIB, which is stronger than its binding affinity to human FcγRIII which is stronger than or equivalent to its binding affinity to human FcγRI, as determined by measurement of the $K_D$ in an in vitro assay. In other embodiments, the antibody exhibits binding affinity to human FcγRIIA>human FcγRIIB>human FcγRIII>=human FcγRI, as measured in an in vitro assay.

In some embodiments the human FcγRIII is human FcγRIIIA or human FcγRIIIB.

In some embodiments, the chimeric Fc domain comprises a chimeric hinge.

In another aspect, the present invention provides a bispecific antibody comprising a first antigen-binding domain, a second antigen-binding domain, and a chimeric heavy chain constant (CH) region, wherein (a) the first antigen-binding domain binds CD3, (b) the second antigen-binding domain binds CD20. In certain aspects of the invention the chimeric CH region binds with higher, i.e. stronger, affinity to human FcγRIIA and human FcγRIIB, compared to an antibody comprising a wild-type CH region, as measured in an in vitro assay. In yet another aspect, the chimeric CH binds with lower, i.e. weaker, or no affinity to human FcγRI and human FcγRIII, compared to an antibody comprising a wild-type CH region, as measured in an in vitro assay.

The invention provides bispecific antibodies comprising a chimeric hinge region. In some aspects the chimeric hinge region comprises amino acid sequence residues from positions 216 to 236 (EU numbering). The bispecific antibodies of the invention are constructed wherein the chimeric hinge comprises a human IgG2 lower hinge amino acid sequence PCPAPPVA (SEQ ID NO: 52) from positions 228 to 236 (EU numbering). In certain embodiments, the bispecific antibodies of the invention comprise a chimeric hinge and the upper hinge portion of the chimeric hinge comprises amino acid residues from positions 216 to 227 (EU numbering) of an IgG1 upper hinge. In other embodiments, the bispecific antibodies of the invention comprise a chimeric hinge and the upper hinge portion of the chimeric hinge comprises amino acid residues from positions 216 to 227 (EU numbering) of an IgG4 upper hinge.

In one embodiment, the bispecific antibody comprises a chimeric hinge amino acid sequence EPKSCDKTHTCPP-CPAPPVA (SEQ ID NO: 53). In another embodiment, the bispecific antibody comprises a chimeric hinge amino acid sequence ESKYGPPCPPCPAPPVA (SEQ ID NO: 54). In certain embodiments, the bispecific antibody of comprises a human IgG4 CH2 domain amino acid sequence from positions 237 to 340 (EU numbering). In other embodiments, the bispecific antibody comprises a CH3 domain derived from a human IgG1 CH3 domain or a human IgG4 CH3 domain. In still other embodiments, the bispecific antibody comprises a human IgG1 CH1 domain and a human IgG1 CH3 domain. In more embodiments, the bispecific antibody comprises a human IgG4 CH1 domain and a human IgG4 CH3 domain.

An aspect of the invention provides a method of making an bispecific antibody comprising a chimeric constant heavy chain region, said method comprising: (a) transfecting a host cell with a nucleic acid molecule encoding a first light chain capable of binding CD3 antigen, said nucleic acid molecule comprising a nucleotide sequence encoding the VL region of the first and a nucleotide sequence encoding the constant CL region of an Ig, wherein said nucleotide sequence encoding the VL region of a selected antigen-specific antibody and said nucleotide sequence encoding the CL region of an Ig are operably linked together; (b) transfecting the host cell of step (a) with a nucleic acid molecule encoding a first heavy chain of the antibody capable of binding CD3 antigen, said nucleic acid molecule comprising a nucleotide sequence encoding the VH region and a nucleotide sequence encoding a chimeric constant CH region of a human Ig, wherein said nucleotide sequence encoding the VH region and the nucleotide sequence encoding the CH region of said Ig are operably linked together; wherein the CH region encodes for one or more amino acid modifications in the CH3 domain that reduces or eliminates binding of the second CH3 domain to Protein A; (c) transfecting the host cell of step (a) with a nucleic acid molecule encoding a second heavy chain of the antibody capable of binding CD20 antigen, said nucleic acid molecule comprising a nucleotide sequence encoding the VH region and a nucleotide sequence encoding a chimeric CH region of a human Ig, wherein said nucleotide sequence encoding the VH region and the nucleotide sequence encoding the CH region of said Ig are operably linked together; and (c) making said antibody by co-expressing the nucleic acid molecules of (a) and (b) in said host cell.

In one embodiment, the present invention provides a method of making a bispecific antibody by: (a) transfecting a host cell with (i) a nucleic acid molecule encoding the light chain of the antibody, wherein the nucleic acid molecule comprises a nucleotide sequence encoding the LCVR comprising SEQ ID NO:18, and a nucleotide sequence encoding the constant $C_L$ region of an Ig, wherein said nucleotide sequence encoding the LCVR region of the antibody is operably linked to the nucleotide sequence encoding the $C_L$ region of an Ig; (b) transfecting the host cell of step (a) with (i) a nucleic acid molecule encoding the first heavy chain of said antibody, said nucleic acid molecule comprising a nucleotide sequence encoding the HCVR comprising SEQ ID NO:10 and a nucleotide sequence encoding a chimeric $C_H$ region of IgG, wherein the nucleotide sequence encoding the $C_H$ region comprises the nucleotide sequence encoding SEQ ID NO: 26, SEQ ID NO: 28, SEQ ID NO: 30, or SEQ ID NO: 32, wherein said nucleotide sequence encoding the HCVR is operably linked to the nucleotide sequence encoding the $C_H$ region; and (ii) a nucleic acid molecule encoding the second heavy chain of said antibody, said nucleic acid molecule comprising a nucleotide sequence encoding the HCVR comprising SEQ ID NO:2 and a nucleotide sequence encoding a chimeric $C_H$ region of IgG, wherein the nucleotide sequence encoding the $C_H$ region comprises the nucleotide sequence encoding SEQ ID NO: 26, SEQ ID NO: 28, SEQ ID NO: 30, or SEQ ID NO: 32, wherein said nucleotide sequence encoding the HCVR is operably linked to the nucleotide sequence encoding the $C_H$ region; and (c) making the antibody by co-expressing the nucleic acid molecules of (a) and (b) in said host cell. In some cases, the method further comprises the steps of culturing the host cell of step (b), in which the antibody is secreted into a cell culture medium; and isolating the antibody from the cell culture media.

In some aspects, the method of making the bispecific antibody optionally comprises transfecting the host cell of step (a) with a nucleic acid molecule encoding a second light chain capable of binding CD20 antigen, said nucleic acid molecule comprising a nucleotide sequence encoding the VL region of the second light chain and a nucleotide sequence encoding the constant CL region of an Ig, wherein said nucleotide sequence encoding the VL region of the second light chain and said nucleotide sequence encoding the CL region of an Ig are operably linked together.

In some embodiments, the first heavy chain comprises a CH3 region comprising an H95R modification (by IMGT exon numbering; H435R by EU numbering). In another embodiment, the first heavy chain comprises a CH3 region further comprising a Y96F modification (IMGT; Y436F by EU numbering). In more embodiments, the method comprises isolating the antibody using Protein A.

Another aspect of the invention provides a bispecific antibody comprising: (a) a first heavy chain comprising an antigen-binding domain capable of recognizing and binding to a first target antigen, (b) a second heavy chain comprising an antigen-binding domain capable of recognizing and binding to a second target antigen, and (c) a common light chain antigen-binding domain capable of recognizing and binding to the first or second target antigen, wherein the heavy chain of (a) or (b) or both (a) and (b) comprises the heavy chain constant region (CH) comprising a chimeric hinge region comprising the amino acid sequence of SEQ ID NO: 53 or SEQ ID NO: 54.

In certain embodiments, the heavy chain constant region (CH) comprises the amino acid sequence of SEQ ID NO: 26, SEQ ID NO: 28, SEQ ID NO: 30, or SEQ ID NO: 32. In some embodiments, the chimeric CH-encoding nucleotide sequence comprises SEQ ID NO: 25, SEQ ID NO: 27, SEQ ID NO: 29, SEQ ID NO: 31, or SEQ ID NO: 33. In other embodiments, the chimeric CH nucleotide sequence encodes the amino acid sequence of SEQ ID NO: 26, SEQ ID NO: 28, SEQ ID NO: 30, or SEQ ID NO: 32. In still other embodiments, the nucleotide sequence of the CH region comprises the nucleotide sequence encoding the amino acid sequence of SEQ ID NO: 25, SEQ ID NO: 27, SEQ ID NO: 29, SEQ ID NO: 31 or SEQ ID NO: 33.

In certain aspects, the bispecific antibody comprises a nucleic acid molecule encoding a light chain comprising the amino acid sequence of SEQ ID NO: 35. In other aspects, the bispecific antibody comprises a light chain-encoding nucleic acid molecule comprising the nucleotide sequence of SEQ ID NO: 34.

In certain aspects, the bispecific antibody comprises a nucleic acid molecule encoding a heavy chain comprising the amino acid sequence of SEQ ID NO: 37. In other aspects, the bispecific antibody comprises a heavy chain-encoding nucleic acid molecule comprising the nucleotide sequence of SEQ ID NO: 36.

In certain aspects, the bispecific antibody comprises a nucleic acid molecule encoding a heavy chain comprising the amino acid sequence of SEQ ID NO: 40. In other aspects, the bispecific antibody comprises a heavy chain-encoding nucleic acid molecule comprising the nucleotide sequence of SEQ ID NO: 38 or SEQ ID NO: 39.

In certain aspects, the bispecific antibody comprises a nucleic acid molecule encoding a heavy chain comprising the amino acid sequence of SEQ ID NO: 42. In other aspects, the bispecific antibody comprises a heavy chain-encoding nucleic acid molecule comprising the nucleotide sequence of SEQ ID NO: 41.

In certain aspects, the bispecific antibody comprises a nucleic acid molecule encoding a heavy chain comprising the amino acid sequence of SEQ ID NO: 44. In other aspects, the bispecific antibody comprises a heavy chain-encoding nucleic acid molecule comprising the nucleotide sequence of SEQ ID NO: 43.

In another aspect, the invention provides a therapeutically effective amount of the anti-CD3/anti-CD20 bispecific antigen-binding molecule as disclosed herein. In a related aspect, the invention features a composition which is a combination of an anti-CD3/anti-CD20 bispecific antigen-binding molecule and a second therapeutic agent. In one embodiment, the second therapeutic agent is any agent that is advantageously combined with an anti-CD3/anti-CD20 bispecific antigen-binding molecule. Exemplary agents that may be advantageously combined with an anti-CD3/anti-CD20 bispecific antigen-binding molecule are discussed in detail elsewhere herein.

In yet another aspect, the invention provides therapeutic methods for targeting/killing tumor cells expressing CD20 using an anti-CD3/anti-CD20 bispecific antigen-binding molecule of the invention, wherein the therapeutic methods comprise administering a therapeutically effective amount of a pharmaceutical composition comprising an anti-CD3/anti-CD20 bispecific antigen-binding molecule of the invention to a subject in need thereof. In some cases, the bispecific antigen-binding molecule (e.g., antibody) binds human cells expressing CD20 or binds human B-cells.

In another aspect, the invention provides bispecific antibodies in which the antibody: binds human cells expressing human CD3 and cynomolgus monkey cells expressing cynomolgus CD3; binds human T-cells or cynomolgus T-cells; binds to CD3-expressing human T-cells with an $EC_{50}$ value of between $1\times10^{-12}$ M and $1\times10^{-6}$ M; binds to CD3-expressing human T-cells with an $EC_{50}$ value of between $1\times10^{-9}$ M and $1\times10^{-8}$ M; binds to CD20-expressing human B-cells with an $EC_{50}$ value of between $1\times10^{-12}$ M and $1\times10^{-6}$ M; binds to CD20-expressing human B-cells with an $EC_{50}$ value of between $1\times10^{-9}$ M and $1\times10^{-8}$ M; or enhances T-cell mediated cytotoxicity of human B-cells that are resistant to or refractory to anti-CD20-mediated cytotoxicity.

In various methods or uses of the present invention, a single administration of the bispecific antibody to a subject at a dose of at least about 0.01 mg/kg causes a reduction in the number of B-cells in the subject below detectable levels by about day 2 after administration of the bispecific antibody to the subject. In some cases, the number of B-cells remains below detectable levels until at least about 7 days after administration of a single dose of at least about 0.01 mg/kg of the bispecific antibody to the subject.

The present invention includes the use of an anti-CD3/anti-CD20 bispecific antigen-binding molecule of the invention for targeting/killing tumor cells expressing CD20, and in the manufacture of a medicament for the treatment of a disease or disorder related to or caused by CD20 expression. In some cases, the bispecific antibody of the present invention is used in the manufacture of a medicament for treating or ameliorating cancer in a subject, wherein the bispecific antibody comprises a first antigen-binding domain that binds human CD3, a second antigen-binding domain that binds human CD20, and a chimeric Fc domain tethered to each of the first and second antigen-binding domains, and the treating or ameliorating cancer comprises: (a) suppressing tumor growth in the subject, (b) mediating B-cell lysis in the subject, (c) treating a B-cell cancer in the subject, (d) treating cancer that is positive for CD20 expression in the subject, or (e) treating CD20-expressing melanoma cancer in the subject.

The present invention also includes a bispecific antibody comprising a first antigen-binding domain, a second antigen-binding domain, and a chimeric heavy chain constant (CH) region, wherein: the first antigen-binding domain binds CD3, the second antigen-binding domain binds CD20, the chimeric CH region binds with higher, i.e. stronger, affinity to human FcγRIIA and human FcγRIIB, compared to an antibody comprising a wild-type CH region, such bispecific antibody for use in the manufacture of a medicament. The invention provides a bispecific antibody comprising a first antigen-binding domain which binds CD3, a second antigen-binding domain which binds CD20, and a chimeric CH region which binds with higher, i.e. stronger, affinity to human FcγRIIA than it binds to human FcγRIIB, for use in the manufacture of a medicament.

Other embodiments will become apparent from a review of the ensuing detailed description.

BRIEF DESCRIPTION OF THE FIGURES

FIG. 1 illustrates hinge amino acids used in the construction of chimeric hinge regions and the corresponding amino acid numbering conventions.

FIG. 2 represents the amino acid sequence of the human IgG1 heavy chain constant region including CH1, hinge, CH2 and CH3 domains as described as IGHG1 in UniProtKB/Swiss-Prot Accn. No. P01857 (SEQ ID NO: 45).

FIG. 3 represents the amino acid sequence of the human IgG2 heavy chain constant region including CH1, hinge, CH2 and CH3 domains as described as IGHG2 in UniProtKB/Swiss-Prot Accn. No. P01859 (SEQ ID NO: 46).

FIG. 4 represents the amino acid sequence of the human IgG4 heavy chain constant region including CH1, hinge, CH2 and CH3 domains as described as IGHG4 in UniProtKB/Swiss-Prot Accn. No. P01861 (SEQ ID NO: 47).

FIGS. 7A-7F show the tumor volume (in $mm^3$) over time in NSG mice implanted subcutaneously with a mixture of Raji tumor cells and PBMCs (or no PBMC control-FIG. 7D) whereas either a CD3×CD20 bispecific antibody of the invention (Ab1) or vehicle or control antibody was administered following tumor implantation and treatment, starting the same day of tumor implantation (Day 0), and measured for the length of the study. FIG. 7A: No mice showed tumor growth inhibition with Vehicle treatment; FIG. 7B: 1 out of 5 (1/5) mice showed tumor growth inhibition with 0.4 mg/kg Control Ab5 (anti-FeID1 Ab) treatment; FIG. 7C: 5/5 mice showed tumor growth inhibition with 0.4 mg/kg Antibody 1 (Ab1) treatment; FIG. 7D: 0/5 mice showed tumor growth inhibition where no PBMCs were implanted and with 0.4 mg/kg Ab1 treatment; FIG. 7E: 5/5 mice showed tumor growth inhibition with 0.04 mg/kg Ab1 treatment; and FIG. 7F: 5/5 mice showed tumor growth inhibition with 0.004 mg/kg Ab1 treatment.

As seen in FIG. 8A, CD3×CD20-chimericFc bispecific antibody (Ab1) demonstrates complete tumor growth inhibition over the time period tested with or without IgG supplementation in this experiment.

FIGS. 11A and 11B depict the in vivo potency of Antibody 1 and Antibody 4 CD3×CD20 bispecific antibody administration compared to monospecific antibody administration (rituximab) by measuring changes in CD20+ B-cell levels or CD3+ T-cell levels in peripheral blood of cynomolgus monkeys in a 7 day study. Antibodies or placebo were administered at Day 0. FIG. 11A: B-cell levels in the peripheral blood were significantly depleted by day 2 in all samples except placebo; FIG. 11B: A transient loss of T-cells was observed by day 2 and restored to baseline levels by day 4 in the peripheral blood of animals treated with bispecific antibodies. No loss of T-cells (below baseline) was observed in the placebo or rituximab (Rituxan) groups.

FIG. 12A: B-cell levels in the peripheral blood were significantly depleted by day 2 and levels remained depleted over the length of the study in all samples except placebo; FIG. 12B: A transient loss of T-cells was observed by day 2, then T-cells recovered to baseline levels by day 4, and remained around baseline as measured throughout the study (>80 days) for animals treated with bispecific antibodies. No transient loss of T-cells was observed in animals treated with placebo.

FIGS. 13A and 13B depict the in vivo potency of Antibody 1 and Antibody 4 CD3×CD20 bispecific antibody low dose administration by measuring changes in CD20+ B-cell levels or CD3+ T-cell levels in peripheral blood of cynomolgus monkeys in a long term (2 month) study. Bispecific antibodies were administered at either 0.01 mg/kg or 0.001 mg/kg (1 µg/kg) at Day 0. FIG. 13A: B-cell levels in the peripheral blood were significantly depleted by day 2 and levels remained depleted over the length of the study, similar to that observed for animals treated with higher doses of CD3×CD20 bispecific antibodies (see also FIG. 11A or 12A); FIG. 13B: Animals treated with very low doses (1 µg/kg) of bispecific antibodies experience the same transient loss of T-cells and recovery as seen in animals treated with higher doses of CD3×CD20 bispecific antibodies (see also FIG. 11B or 12B).

FIGS. 19A and 19B illustrates CD3×CD20-mediated Raji target killing in a cytotoxicity assay. Antibody 1 mediated target cell killing with representative $EC_{50}$ values of 25.0pM and 9.10pM for human (FIG. 19A) and cynomolgus (FIG. 19B) T cells, respectively. Antibody 4 mediated target cell killing with representative $EC_{50}$ values of 15.7pM and 1.73pM for human (FIG. 19A) and cynomolgus (FIG. 19B) T cells, respectively. No activity of the control (-▲-) was observed.

FIG. 20A shows a representative FACS scatter plot at the highest tested concentration of Antibody 4. B16F10.9 wild-type cells are labeled with CFDA-SE and B16F10.9/CD20 cells are labeled with Violet Cell Tracker. Effector cells are not labeled. The second panel of FIG. 20A shows that CD20-expressing cells are eliminated (lower right quadrant) by treatment with anti-CD3×CD20. FIG. 20B shows the proportion of surviving B16F10.9/CD20 cells after 48 hours in the presence of CD20×CD3 antibodies, i.e. Antibody 4 (wtFc), Antibody 1(chimericFc) or Control Ab 5, and PBMCs. Percent survival was determined by comparing the percentage of B16F10.9/CD20 cells to CD20 negative B16F10.9 cells in the live cell population. Ab 4 and Ab 1 specifically directed human T cells to kill only target cells expressing CD20 (FIG. 20B) in a mixed population of cells. Target cell killing was only observed in the presence of the bispecific antibodies, with B16F10.9/CD20 cells depleted in a dose-dependent manner by Antibody 4 ($EC_{50}$ 12.8pM) and Antibody 1 ($EC_{50}$ 19.5pM) (FIG. 20B). Less than 5% of CD20-expressing cells were alive at the highest dose tested (10 µg/mL).

FIG. 21 shows the percent of activated (CD69+) cells out of total CD2+ effector cells in a 48-hour cytotoxicity assay targeting B16F10.9/CD20 cells, such activation induced by either CD20×CD3 antibody, i.e. Antibody 4 (wtFc) or Antibody 1 (chimeric Fc).

FIGS. 22A and 22B illustrate that CD3×CD20 bispecific antibody induced clustering of T-cells with the target cells (CD20+ cells) via its bispecific binding arms. Effector cells are stained with CFSE and CD20+ cells are stained with Violet Cell Tracker, and gated to separate quadrants. Following incubation with an irrelevant control antibody (Control Antibody 5), no clustering (double-staining) appears in the cell mixture (FIG. 22A). Following incubation with CD3×CD20 bispecific antibody (Ab 4), cell clusters appear because they are stained with both CFSE and Violet (see the upper left quadrant on the scatterplot of FIG. 22B, as highlighted by the bold square).

FIG. 25A: hCD3 mice were implanted subcutaneously with hCD20-transduced B16F10.9 melanoma cells and treated simultaneously with 0.004 mg/kg or 0.4 mg/kg Antibody 1 (CD3× CD20-chimeric Fc antibody), or 4 mg/kg Control Ab5 (anti-FeID1 Ab), or vehicle control (i.p. 2 times per week). FIG. 25B: hCD3 mice were implanted subcutaneously with hCD20/B16F10.9 melanoma cells and established tumors were treated on day 10 and thereafter with Antibody 1 (CD3×CD20-chimeric Fc antibody) or control. Mice were treated i.p. twice per week with 0.4 mg/kg or 4 mg/kg Ab1, or 0.4 mg/kg Control Ab5 (anti-FeID1 Ab), or vehicle control.

DETAILED DESCRIPTION

Figure 5A:
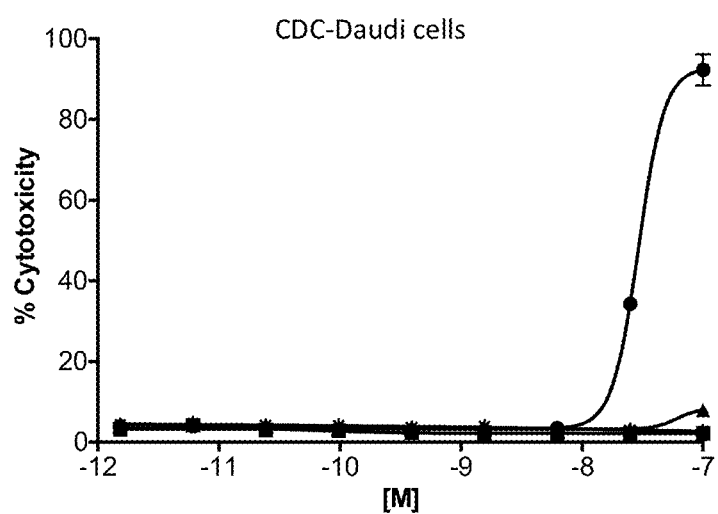
FIGS. 5A and 5B: Dose-response curves depicting lack of CDC activity with respect to Daudi (FIG. 5A) and Raji (FIG. 5B) cells in the presence of antibodies having wild-type or chimeric hinge $C_H$ regions. ("Control" Antibody 4=Bispecific Ab with wt IgG1 $C_H$; Antibody 1; Antibody 2; IgG1 Isotype Control=nonspecific Ab with wt IgG1 $C_H$.)

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described.

Definitions

The expression "CD3," as used herein, refers to an antigen which is expressed on T cells as part of the multi-molecular T cell receptor (TCR) and which consists of a homodimer or heterodimer formed from the association of two of four receptor chains: CD3-epsilon, CD3-delta, CD3-zeta, and CD3-gamma. All references to proteins, polypeptides and protein fragments herein are intended to refer to the human version of the respective protein, polypeptide or protein fragment unless explicitly specified as being from a non-human species. Thus, the expression "CD3" means human CD3 unless specified as being from a non-human species, e.g., "mouse CD3," "monkey CD3," etc.

As used herein, "an antibody that binds CD3" or an "anti-CD3 antibody" includes antibodies and antigen-binding fragments thereof that specifically recognize a single CD3 subunit (e.g., epsilon, delta, gamma or zeta), as well as antibodies and antigen-binding fragments thereof that specifically recognize a dimeric complex of two CD3 subunits (e.g., gamma/epsilon, delta/epsilon, and zeta/zeta CD3 dimers). The antibodies and antigen-binding fragments of the present invention may bind soluble CD3 and/or cell surface expressed CD3. Soluble CD3 includes natural CD3 proteins as well as recombinant CD3 protein variants such as, e.g., monomeric and dimeric CD3 constructs, that lack a transmembrane domain or are otherwise unassociated with a cell membrane.

As used herein, the expression "cell surface-expressed CD3" means one or more CD3 protein(s) that is/are expressed on the surface of a cell in vitro or in vivo, such that at least a portion of a CD3 protein is exposed to the extracellular side of the cell membrane and is accessible to an antigen-binding portion of an antibody. "Cell surface-expressed CD3" includes CD3 proteins contained within the context of a functional T cell receptor in the membrane of a cell. The expression "cell surface-expressed CD3" includes CD3 protein expressed as part of a homodimer or heterodimer on the surface of a cell (e.g., gamma/epsilon, delta/epsilon, and zeta/zeta CD3 dimers). The expression, "cell surface-expressed CD3" also includes a CD3 chain (e.g., CD3-epsilon, CD3-delta or CD3-gamma) that is expressed by itself, without other CD3 chain types, on the surface of a cell. A "cell surface-expressed CD3" can comprise or consist of a CD3 protein expressed on the surface of a cell which normally expresses CD3 protein. Alternatively, "cell surface-expressed CD3" can comprise or consist of CD3 protein expressed on the surface of a cell that normally does not express human CD3 on its surface but has been artificially engineered to express CD3 on its surface.

As used herein, the expression "anti-CD3 antibody" includes both monovalent antibodies with a single specificity, as well as bispecific antibodies comprising a first arm that binds CD3 and a second arm that binds a second (target) antigen, wherein the anti-CD3 arm comprises any of the HCVR/LCVR or CDR sequences as set forth in Table 1 or Table 2 herein. Examples of anti-CD3 bispecific antibodies are described elsewhere herein. The term "antigen-binding molecule" includes antibodies and antigen-binding fragments of antibodies, including, e.g., bispecific antibodies. Exemplary anti-CD3 antibodies are also described in US 2007/0280945A1; and in PCT International Application No. PCT/US13/60511, filed on Sep. 19, 2013, which is herein incorporated by reference in its entirety.

The term "CD20," as used herein, refers to the human CD20 protein unless specified as being from a non-human species (e.g., "mouse CD20," "monkey CD20," etc.). The human CD20 protein has the amino acid sequence as in NCBI Reference Sequence NP_690605.1.

As used herein, the expression "anti-CD20 antibody" includes monovalent antibodies with a single specificity, such as Rituxan (rituximab), as described in U.S. Pat. No. 7,879,984. Exemplary anti-CD20 antibodies are also described in U.S. Pat. No. 7,879,984 and PCT International Application No. PCT/US13/60511, filed on Sep. 19, 2013, each incorporated by reference herein.

The term "antibody", as used herein, means any antigen-binding molecule or molecular complex comprising at least one complementarity determining region (CDR) that specifically binds to or interacts with a particular antigen (e.g., CD3). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-CD3 antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant fragment (Fc) domain, or otherwise tethered to an Fc domain. The term "tethered to" refers to a direct linkage via covalent bond, or a linker polypeptide sequence, to bring together two components such as a variable domain tethered to a constant domain. Thus, in certain examples, variable domains comprising a first and second antigen-binding domain, such as those that bind CD3 and CD20 to form a bispecific antibody, are each directly linked (or tethered) via a covalent bond or a linker amino acid sequence to, e.g. (from N-terminus to C-terminus) full or partial $C_H1$, chimeric hinge, $C_H2$ and $C_H3$ domains. Non-limiting, exemplary configurations of variable and constant domains that may be found within an antigen-binding fragment of an antibody of the present invention include: (i) $V_H$-$C_H1$-hinge-$C_H2$-$C_H3$; (ii) $V_H$-hinge-$C_H2$-$C_H3$; (iii) $V_H$-$C_L$; (iv) $V_L$-$C_H1$-$C_H2$-$C_H3$; (v) $V_L$-$C_H2$-$C_H3$; and (vi) $V_L$-$C_L$. In any configuration of variable and constant domains, including any of the exemplary configurations listed above, the variable and constant domains may be either directly linked to one another or may be linked (tethered) by a full or partial chimeric hinge of the invention, or by a full or partial $C_H1$ and chimeric hinge. In some cases, a polypeptide linker (e.g., from 2 to 10 amino acids) may connect (tether) the variable and Fc domains or may comprise an additional linkage with the full or partial chimeric hinge and/or $C_H1$. A hinge region may consist of at least upper and lower hinge amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

A multispecific antibody format of the invention, including the exemplary bispecific antibody formats disclosed herein, typically comprises at least two different variable domains, wherein each variable domain is capable of specifically binding to a separate antigen. Multispecific formats may be adapted for use in the context of an antigen-binding fragment of an antibody of the present invention using routine techniques available in the art.

The antibodies of the present invention are modified to have decreased or no complement-dependent cytotoxicity (CDC) or antibody-dependent cell-mediated cytotoxicity (ADCC) as measured in vitro. "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The heavy chain constant region (CH) of an antibody is important in the ability of an antibody to fix complement and mediate cell-dependent cytotoxicity. Thus, the CH of an antibody may be selected on the basis of whether it is desirable for the antibody to mediate cytotoxicity.

In certain embodiments of the invention, the bispecific antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge region which may in production, for example, improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-CD3 or anti-CD20 variable regions disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-CD3 or anti-CD20 variable regions comprising variants of any of the HCVR, LCVR, and/or CDR amino acid sequences disclosed herein having one or more conservative substitutions. For example, the present invention includes anti-CD3 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestf it which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

Bispecific Antigen-Binding Molecules

The antibodies of the present invention may bispecific or multispecific. Multispecific antibodies may be specific for different epitopes of one target polypeptide or may contain antigen-binding domains specific for more than one target polypeptide. See, e.g., Tutt et al., 1991, J. Immunol. 147: 60-69; Kufer et al., 2004, Trends Biotechnol. 22:238-244. The anti-CD3×CD20 antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with an additional binding specificity.

Thus, the present invention includes bispecific antibodies wherein one arm of an immunoglobulin binds human CD3, and the other arm of the immunoglobulin is specific for a target antigen. The target antigen that the other arm of the CD3 bispecific antibody binds can be any antigen expressed on or in the vicinity of a cell, tissue, organ, microorganism or virus, against which a targeted immune response is desired. The CD3-binding arm can comprise any of the HCVR/LCVR or CDR amino acid sequences as set forth in Table 1 herein.

In the context of bispecific antibodies of the present invention wherein one arm of the antibody binds CD3 and the other arm binds a target antigen, the target antigen can be a tumor-associated antigen. Non-limiting examples of specific tumor-associated antigens include, e.g., AFP, ALK, BAGE proteins, BIRC5 (survivin), BIRC7, β-catenin, brc-abl, BRCA1, BORIS, CA9, carbonic anhydrase IX, caspase-8, CALR, CCR5, CD19, CD20 (MS4A1), CD22, CD30, CD40, CDK4, CEA, CTLA4, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, TAG-72, TGF-β, TMPRSS2, Thompson-nouvelle antigen (Tn), TRP-1, TRP-2, tyrosinase, and uroplakin-3.

In the context of bispecific antibodies of the present invention wherein one arm of the antibody binds CD3 and the other arm binds a target antigen, the target antigen can be an infectious disease-associated antigen. Non-limiting examples of infectious disease-associated antigens include, e.g., an antigen that is expressed on the surface of a virus particle, or preferentially expressed on a cell that is infected with a virus, wherein the virus is selected from the group consisting of HIV, hepatitis (A, B or C), herpes virus (e.g., HSV-1, HSV-2, CMV, HAV-6, VZV, Epstein Barr virus), adenovirus, influenza virus, flavivirus, echovirus, rhinovirus, coxsackie virus, coronavirus, respiratory syncytial virus, mumps virus, rotavirus, measles virus, rubella virus, parvovirus, vaccinia virus, HTLV, dengue virus, papillomavirus, molluscum virus, poliovirus, rabies virus, JC virus, and arboviral encephalitis virus. Alternatively, the target antigen can be an antigen that is expressed on the surface of a bacterium, or preferentially expressed on a cell that is infected with a bacterium, wherein the bacterium is selected from the group consisting of chlamydia, rickettsia, mycobacteria, staphylococci, streptococci, pneumonococci, meningococci, gonococci, klebsiella, proteus, serratia, pseudomonas, legionella, diphtheria, salmonella, bacilli, cholera, tetanus, botulism, anthrax, plague, leptospira, and Lyme disease bacteria. In certain embodiments, the target antigen is an antigen that is expressed on the surface of a fungus, or preferentially expressed on a cell that is infected with a fungus, wherein the fungus is selected from the group consisting of *Candida* (*albicans, krusei, glabrata, tropicalis*, etc.), *Crytococcus neoformans, Aspergillus* (*fumigatus, niger*, etc.), *Mucorales* (*mucor, absidia, rhizopus*, etc.), *Sporothrix schenkii, Blastomyces dermatitidis, Paracoccidioides brasiliensis, Coccidioides immitis*, and *Histoplasma capsulatum*. In certain embodiments, the target antigen is an antigen that is expressed on the surface of a parasite, or preferentially expressed on a cell that is infected with a parasite, wherein the parasite is selected from the group consisting of *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis, Taenia crassiceps*, and *Brugia malayi*. Non-limiting examples of specific pathogen-associated antigens include, e.g., HIV gp120, HIV CD4, hepatitis B glucoprotein L, hepatitis B glucoprotein M, hepatitis B glucoprotein S, hepatitis C E1, hepatitis C E2, hepatocyte-specific protein, herpes simplex virus gB, cytomegalovirus gB, and HTLV envelope protein.

According to certain exemplary embodiments, the present invention includes bispecific antigen-binding molecules that specifically bind CD3 and CD20. Such molecules may be referred to herein as, e.g., "anti-CD3/anti-CD20," or "anti-CD3/CD20," or "anti-CD3×CD20" or "CD3×CD20" bispecific molecules, or other similar terminology.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

As used herein, the expression "bispecific antigen-binding molecule" means a protein, polypeptide or molecular complex comprising at least a first antigen-binding domain and a second antigen-binding domain. Each antigen-binding domain within the bispecific antigen-binding molecule comprises at least one CDR that alone, or in combination with one or more additional CDRs and/or FRs, specifically binds to a particular antigen. In the context of the present invention, the first antigen-binding domain specifically binds a first antigen (e.g., CD3), and the second antigen-binding domain specifically binds a second, distinct antigen (e.g., CD20).

In certain exemplary embodiments of the present invention, the bispecific antigen-binding molecule is a bispecific antibody. Each antigen-binding domain of a bispecific antibody comprises a heavy chain variable domain (HCVR) and a light chain variable domain (LCVR). In the context of a bispecific antigen-binding molecule comprising a first and a second antigen-binding domain (e.g., a bispecific antibody), the CDRs of the first antigen-binding domain may be designated with the prefix "A1" and the CDRs of the second antigen-binding domain may be designated with the prefix "A2". Thus, the CDRs of the first antigen-binding domain may be referred to herein as A1-HCDR1, A1-HCDR2, and A1-HCDR3; and the CDRs of the second antigen-binding domain may be referred to herein as A2-HCDR1, A2-HCDR2, and A2-HCDR3.

The first antigen-binding domain and the second antigen-binding domain may be directly or indirectly connected to one another to form a bispecific antigen-binding molecule of the present invention (i.e. bispecific ScFv) further bound to an Fc domain. Alternatively, the first antigen-binding domain and the second antigen-binding domain may each be connected to a separate Fc domain. Bispecific antigen-binding molecules of the present invention will typically comprise two Fc domains that are each individually part of a separate antibody heavy chain. The first and second Fc domains may be of the same sequence, except having a mutation in the $C_H3$ domain intended for the facilitation or ease of purification of heterodimeric (i.e. bispecific) molecules.

The present invention includes bispecific antigen-binding molecules comprising a first $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H435R modification (by EU numbering; H95R by IMGT exon numbering). The second $C_H3$ may further comprise a Y436F modification (by EU numbering; Y96F by IMGT). Further modifications that may be found within the second $C_H3$ include: D356E, L358M, N384S, K392N, V397M, and V422I by EU (D16E, L18M, N44S, K52N, V57M, and V82I by IMGT) in the case of IgG1 $C_H3$ domains; and Q355R, N384S, K392N, V397M, R409K, E419Q, and V422I by EU (Q15R, N44S, K52N, V57M, R69K, E79Q, and V82I by IMGT) in the case of IgG4 $C_H3$ domains.

Other bispecific antibody formats or technologies may be used to make the bispecific antigen-binding molecules of the present invention. For example, an antibody or fragment thereof having a first antigen binding specificity can be functionally linked (e.g., by chemical coupling, genetic fusion, noncovalent association or otherwise) to one or more other molecular entities, such as another antibody or antibody fragment having a second antigen-binding specificity to produce a bispecific antigen-binding molecule. Specific exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED)body, leucine zipper, Duobody, IgG1/IgG2, dual acting Fab (DAF)-IgG, and Mab$^2$ bispecific formats (see, e.g., Klein et al. 2012, mAbs 4:6, 1-11, and references cited therein, for a review of the foregoing formats).

In the context of bispecific antigen-binding molecules of the present invention, the Fc domains may comprise one or more amino acid changes (e.g., insertions, deletions or substitutions) as compared to the specified chimeric version of the Fc domain, without changing the desired functionality. For example, the invention includes bispecific antigen-binding molecules comprising one or more modifications in the Fc domain that results in a modified Fc domain having a modified binding interaction (e.g., enhanced or diminished) between Fc and FcRn. In one embodiment, the bispecific antigen-binding molecule comprises a modification in a $C_H2$ or a $C_H3$ region, wherein the modification increases the affinity of the Fc domain to FcRn in an acidic environment (e.g., in an endosome where pH ranges from about 5.5 to about 6.0). Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

Sequence Variants

The antibodies and bispecific antigen-binding molecules of the present invention may comprise one or more amino acid substitutions, insertions and/or deletions in the framework and/or CDR regions of the heavy and light chain variable domains as compared to the corresponding germline sequences from which the individual antigen-binding domains were derived. Such mutations can be readily ascertained by comparing the amino acid sequences disclosed herein to germline sequences available from, for example, public antibody sequence databases. The antigen-binding molecules of the present invention may comprise antigen-binding domains which are derived from any of the exemplary amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antigen-binding domain was originally derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antigen-binding domain was originally derived). Furthermore, the antigen-binding domains may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antigen-binding domains that contain one or more germline mutations can be easily tested for one or more desired property such as, improved binding specificity, increased binding affinity, improved or enhanced antagonistic or agonistic biological properties (as the case may be), reduced immunogenicity, etc. Bispecific antigen-binding molecules comprising one or more antigen-binding domains obtained in this general manner are encompassed within the present invention.

The present invention also includes antigen-binding molecules wherein one or both antigen-binding domains comprise variants of any of the HCVR, LCVR, and/or CDR amino acid sequences disclosed herein having one or more conservative substitutions. For example, the present invention includes antigen-binding molecules comprising an antigen-binding domain having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, may be measured using sequence analysis software. Protein analysis software matches similar sequences using measures of similarity assigned to various substitutions, deletions and other modifications, including conservative amino acid substitutions. For instance, GCG software contains programs such as Gap and Bestf it which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

pH-Dependent Binding

The present invention includes anti-CD3/anti-CD20 bispecific antibodies, with pH-dependent binding characteristics. For example, an anti-CD3 antibody of the present invention may exhibit reduced binding to CD3 at acidic pH as compared to neutral pH. Alternatively, anti-CD3 antibodies of the invention may exhibit enhanced binding to CD3 at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding . . . at acidic pH as compared to neutral pH" is expressed in terms of a ratio of the $K_D$ value of the antibody binding to its antigen at acidic pH to the $K_D$ value of the antibody binding to its antigen at neutral pH (or vice versa). For example, an antibody or antigen-binding fragment thereof may be regarded as exhibiting "reduced binding to CD3 at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Fc Receptor Binding

Anti-CD3/anti-CD20 bispecific antigen-binding molecules and antibodies of the invention are provided comprising a chimeric Fc domain, such as a hinge-CH2-CH3 constant domain of an Ig heavy chain, derived from different IgG isotypes and having unique characteristics with regard to Fc receptor binding and activation. Certain Fc domains of the invention are engineered to comprise a chimeric hinge.

The term "chimeric", as used herein, means composed of parts of different origin. The phrase "chimeric protein" includes a first amino acid protein linked to a second amino acid protein that is not normally linked in nature. The amino acid sequences may normally exist as separate proteins or in a different arrangement on the same protein, and are brought together in a fusion polypeptide in a new arrangement. Chimeric proteins may be created by various methods known in the art, e.g. by chemical synthesis or by creating a polynucleotide that encodes for amino acids of the chimeric protein in the desired arrangement. Exemplary chimeric proteins include the chimeric hinge sequences connecting heavy chain domains of IgG, and the fusion proteins engineered to make the human antibodies and antigen-binding proteins of the present invention.

The chimeric proteins disclosed herein were designed to minimize the creation of immunogenic epitopes in the junctions, e.g. compared to a wild-type IgG Fc region or domain. The engineered proteins of the invention therefore have reduced immunogenicity, and display reduced binding to Fc receptors, as well as reduced to no effector functions.

The term "hinge", as used herein, is intended to include the region of consecutive amino acid residues that connect the C-terminus of the $C_H1$ to the N-terminus of the $C_H2$ domain of an immunoglobulin. Several amino acids of the N-terminus of the $C_H2$ domain, which are coded by the $C_H2$ exon, are also considered part of the "lower hinge". Without being bound by any one theory, amino acids of the hinge region of IgG1, IgG2 and IgG4 have been characterized as comprising 12-15 consecutive amino acids encoded by a distinct hinge exon, and several N-terminal amino acids of the $C_H2$ domain (encoded by the $C_H2$ exon) (Brekke, O. H., et al. *Immunology Today* 16(2):85-90 (1995)). On the other hand, IgG3 comprises a hinge region consisting of four segments: one upper segment resembling the hinge region of IgG1, and 3 segments that are identical amino acid repeats unique to IgG3.

The term "chimeric hinge", as used herein, is intended to include a chimeric protein comprising a first amino acid sequence derived from the hinge region of one Ig molecule and a second amino acid sequence derived from the hinge region of a different class or subclass of Ig molecule. Exemplary chimeric hinges of the present invention comprise a first amino acid sequence, or an "upper hinge" sequence, derived from a human IgG1 hinge region or human IgG4 hinge region, and a second amino acid sequence, or a "lower hinge" sequence, derived from a human IgG2 hinge region. In certain embodiments, the first or "upper hinge" sequence comprises amino acid residues from positions 216 to 227 according to EU numbering. In some embodiments, the second or "lower hinge" sequence comprises amino acid residues from positions 228 to 236 according to EU numbering.

For the purposes of this disclosure, an "upper hinge" region is intended to include amino acid residues from positions 216 to 227 according to EU numbering (amino acid residues from positions 226 to 240 according to Kabat numbering) (see FIG. 1). A "lower hinge" region is intended to include amino acid residues from positions 228 to 236 according to EU numbering (amino acid residues from positions 241 to 249 according to Kabat numbering) (see FIG. 1).

In the present disclosure for the convenience of the practitioner of the invention, amino acids of the hinge region for human IgG1, IgG2 and IgG4 have been identified herein by the EU numbering system of Kabat (Kabat, E. A. et al., Sequences of Proteins of Immunological interest. 5$^{th}$ ed. US Department of Health and Human Services, NIH publication No. 91-3242 (1991)), also known as "EU numbering" or the "EU index", as updated according to the IMGT® Scientific Chart, IMGT®, the international ImMunoGeneTics information System®, http://www.imgt.org/IMGTScientific-Chart/Numbering/Hu_IGHGnber.html, created: 17 May 2001, last updated: 10 Jan. 2013.

Correspondence between EU numbering for human IgG1, IgG2 and IgG4 hinge amino acids and IMGT unique domain numbering, IMGT exon numbering, and Kabat numbering conventions (see also Kabat, E. A. et al., 1991, supra) are described in Tables A through F as follows:

TABLE A

IgG1 hinge numbering

| IgG1 (IGHG1) amino acids [SwissProt P01857]* | IMGT Unique Numbering for the HINGE [a] | IMGT Exon Numbering [a] | EU Numbering | Kabat Numbering |
|---|---|---|---|---|
| (E) | 1 | 1 | 216 | 226 |
| P | 2 | 2 | 217 | 227 |
| K | 3 | 3 | 218 | 228 |
| S | 4 | 4 | 219 | 232[a] [229][b] |
| C | 5 | 5 | 220 | 233[a] [230][b] |
| D | 6 | 6 | 221 | 234[a] [232][b] |
| K | 7 | 7 | 222 | 235 |
| T | 8 | 8 | 223 | 236 |
| H | 9 | 9 | 224 | 237 |
| T | 10 | 10 | 225 | 238 |
| C | 11 | 11 | 226 | 239 |
| P | 12 | 12 | 227 | 240 |
| P | 13 | 13 | 228 | 241 |
| C | 14 | 14 | 229 | 242 |
| P | 15 | 15 | 230 | 243 |

*amino acid residues 99-113 of SEQ ID NO: 45.

TABLE B

IgG1 C-domain hinge numbering

| IgG1 (IGHG1) amino acids [SwissProt P01857]* | IMGT Unique Numbering for C-domains [a] | IMGT Exon Numbering [a] | EU Numbering | Kabat Numbering |
|---|---|---|---|---|
| (A) | 1.6 | 1 | 231 | 244 |
| P | 1.5 | 2 | 232 | 245 |
| E | 1.4 | 3 | 233 | 246 |
| L | 1.3 | 4 | 234 | 247 |
| L | 1.2 | 5 | 235 | 248 |
| G | 1.1 | 6 | 236 | 249 |

*amino acid residues 114-119 of SEQ ID NO: 45.

TABLE C

IgG2 hinge numbering

| IgG2 (IGHG2) amino acids [SwissProt P01859]* | IMGT Unique Numbering for the HINGE [a] | IMGT Exon Numbering [a] | EU Numbering | Kabat Numbering |
|---|---|---|---|---|
| (E) | 1 | 1 | 216 | 226 |
| R | 2 | 2 | 217 | 227 |
| K | 3 | 3 | 218 | 228 |
| C | 4 | 4 | 219[a] (221)[b] | 232 |
| C | 5 | 5 | 220[a] (—)[b] | 233 |
| V | 6 | 6 | 222 | 235 |
| E | 7 | 7 | 224 | 237 |
| C | 8 | 8 | 226 | 239 |
| P | 9 | 9 | 227 | 240 |
| P | 10 | 10 | 228 | 241 |
| C | 11 | 11 | 229 | 242 |
| P | 12 | 12 | 230 | 243 |

*amino acid residues 99-110 of SEQ ID NO: 46.

TABLE D

IgG2 C-domain hinge numbering

| IgG2 (IGHG2) amino acids [SwissProt P01859]* | EU numbering | Kabat numbering |
|---|---|---|
| (A) | 231 | 244 |
| P | 232 | 245 |
| P | 233 | 246 |
| V | 234 | 247 |
| A | 235 | 248 |
| — | 236 | 249 |

*amino acid residues 111-115 of SEQ ID NO: 46.

TABLE E

IgG4 hinge numbering

| IgG4 (IGHG4) amino acids [SwissProt P01861]* | IMGT Unique Numbering for the HINGE [a] | IMGT Exon Numbering [a] | EU Numbering | Kabat Numbering |
|---|---|---|---|---|
| (E) | 1 | 1 | 216 | 226 |
| S | 2 | 2 | 217 | 227 |
| K | 3 | 3 | 218 | 228 |
| Y | 4 | 4 | —[a] (219)[b] | 229 |
| G | 5 | 5 | —[a] (220)[b] | 230 |
| P | 6 | 6 | 224 | 237 |
| P | 7 | 7 | 225 | 238 |
| C | 8 | 8 | 226 | 239 |
| P | 9 | 9 | 227 | 240 |
| S | 10 | 10 | 228 | 241 |

TABLE E-continued

IgG4 hinge numbering

| IgG4 (IGHG4) amino acids [SwissProt P01861]* | IMGT Unique Numbering for the HINGE [a] | IMGT Exon Numbering [a] | EU Numbering | Kabat Numbering |
|---|---|---|---|---|
| C | 11 | 11 | 229 | 242 |
| P | 12 | 12 | 230 | 243 |

*amino acid residues 99-110 of SEQ ID NO: 47.

TABLE F

IgG4 C-domain hinge numbering

| IgG4 (IGHG4) amino acids [SwissProt P01861]* | EU Numbering | Kabat Numbering |
|---|---|---|
| (A) | 231 | 244 |
| P | 232 | 245 |
| E | 233 | 246 |
| F | 234 | 247 |
| L | 235 | 248 |
| G | 236 | 249 |

*amino acid residues 111-116 of SEQ ID NO: 47.
Amino acids resulting from exon splicing are shown in parentheses.
— means no corresponding number reported
— — means no corresponding amino acid in this position
[a] numbering according to the last updated IMGT Scientific Chart
[b] numbering according to EU index as reported in Kabat, EA, et al. 1991
See also, e.g., Lefranc, M. -P. et al., *Devel Comp Immunol*, 29, 185-203 (2005); and Edelman, G. M. et al. *PNAS USA*, 63:78-85 (1969).

The term "binding" in the context of the binding of an antibody, Ig, antibody-binding fragment, or Fc-containing protein to either, e.g., a predetermined antigen or to an FcγR, typically refers to an interaction or association between a minimum of two entities, or molecular structures, such as an antibody-antigen interaction, or an Fc-containing protein to an FcγR.

For instance, binding affinity typically corresponds to a $K_D$ value of about $10^{-7}$ M or less, such as about $10^{-8}$ M or less, such as about $10^{-9}$ M or less when determined by, for instance, surface plasmon resonance (SPR) technology in a BIAcore 3000 instrument using the antigen or FcR as the ligand and the antibody, Ig, antibody-binding fragment, or Fc-containing protein as the analyte (or antiligand). Accordingly, the antibody or other binding protein binds to the predetermined antigen or receptor with an affinity corresponding to a $K_D$ value that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein).

The term "$K_D$" (M), as used herein, refers to the dissociation equilibrium constant of a particular antibody-antigen interaction, or the dissociation equilibrium constant of an antibody, Ig, antibody-binding fragment, or Fc-containing protein to an FcγR. There is an inverse relationship between $K_D$ and binding affinity, therefore the smaller the $K_D$ value, the higher, i.e. stronger, the affinity. Thus, the terms "higher affinity" or "stronger affinity" relate to a higher ability to form an interaction and therefore a smaller $K_D$ value, and conversely the terms "lower affinity" or "weaker affinity" relate to a lower ability to form an interaction and therefore a larger $K_D$ value. In some circumstances, a higher binding affinity (or $K_D$) of a particular molecule (e.g. antibody) to its interactive partner molecule (e.g. receptor X) compared to the binding affinity of the molecule (e.g. antibody) to another interactive partner molecule (e.g. receptor Y) may be expressed as a binding ratio determined by dividing the larger $K_D$ value (lower, or weaker, affinity) by the smaller $K_D$ (higher, or stronger, affinity), for example expressed as 5-fold or 10-fold greater binding affinity, as the case may be.

The term "$k_d$" (sec −1 or 1/s), as used herein, refers to the dissociation rate constant of a particular antibody-antigen interaction, or the dissociation rate constant of an antibody, Ig, antibody-binding fragment, or Fc-containing protein to an FcγR. Said value is also referred to as the $k_{off}$ value.

The term "$k_a$" (M-1×sec-1 or 1/M), as used herein, refers to the association rate constant of a particular antibody-antigen interaction, or the association rate constant of an antibody, Ig, antibody-binding fragment, or Fc-containing protein to an FcγR.

The term "$K_A$" (M-1 or 1/M), as used herein, refers to the association equilibrium constant of a particular antibody-antigen interaction, or the association equilibrium constant of an antibody, Ig, antibody-binding fragment, or Fc-containing protein to an FcγR. The association equilibrium constant is obtained by dividing the $k_a$ by the $k_d$.

The term "EC50" or "$EC_{50}$", as used herein, refers to the half maximal effective concentration, which includes the concentration of an antibody which induces a response halfway between the baseline and maximum after a specified exposure time. The $EC_{50}$ essentially represents the concentration of an antibody where 50% of its maximal effect is observed. Thus, reduced binding is observed with an increased $EC_{50}$, or half maximal effective concentration value.

In one embodiment, decreased binding can be defined as an increased $EC_{50}$ antibody concentration which enables binding to the half-maximal amount of target cells.

In some embodiments, decreased cytotoxic activity, such as ADCC or CDC, can be defined as an increased $EC_{50}$ antibody concentration which enables lysis of the half-maximal amount of target cells. Cytotoxicity is also measured as percent cytotoxicity, or percent lysis which is the fraction of a total population of cells observed as lysed in a calcein release assay or equivalent assay. The percent cytotoxicity can be measured as described in Example 6.

In other embodiments, decreased proliferation can be defined as an increased $EC_{50}$ antibody concentration which enables proliferation of the half-maximal amount of target cells.

The phrase "effector functions", as used herein, is intended to include the functional capabilities imparted by an Fc-containing protein upon binding to an FcγR. Without being bound to any one theory, formation of an Fc/FcγR complex recruits a variety of effector cells to sites of bound antigen, typically resulting in diverse signaling events within the cells and important subsequent immune responses.

Chimeric Fc-containing antigen-binding proteins and antibodies of the invention display altered or reduced effector functions as compared to corresponding wild-type Fc-containing antigen-binding proteins or antibodies. See, e.g., PCT Publication No. WO 2014/121087, published 7 Aug. 2014, which is hereby incorporated by reference in its entirety.

In some embodiments, the effector function that is reduced or altered is a cytotoxic effector function, e.g., cytotoxicity, complement-dependent cytotoxicity (CDC), or antibody-dependent cytotoxicity (ADCC). In one embodiment, the effector function that is reduced or altered is complement-dependent cytotoxicity. In another embodiment, the effector function that is reduced or altered is antibody-dependent cytotoxicity. In other embodiments, the effector function that is reduced or altered is cellular proliferation of the target cells.

Several antibody effector functions are mediated at least in part by Fc receptors (FcRs), which bind the Fc region of an antibody in the constant domain (specifically, the CH2 and CH3 domain) of a typical immunoglobulin. There are a number of Fc receptors which are specific for the different classes of immunoglobulins, i.e. IgG, IgE, IgA, IgM, and IgD. The human IgG Fc receptor family is divided into three groups: FcγRI (CD64), which is capable of binding IgG with high affinity, FcγRII (CD32) and FcγRIII (CD16) both of which are low affinity receptors. Each FcγR subclass is encoded by two or three genes, and alternative RNA splicing leads to multiple transcripts, hence, a broad diversity in FcγR isoforms exists (e.g. FcγRIA (CD64; FCGR1A), FcγRIB (CD64; FCRG1B), FcγRIIA (CD32A; FCGR2A), FcγRIIB (CD32B; FCGR2B), FcγRIIC (CD32C; FCGR2C), FcγRIIIA (CD16a; FCGR3A), and FcγRIIIB (CD16b; FCGR3B)). Additionally, the FcRn, or neonatal Fc receptor (also known as the Fc receptor transporter, alpha, or FCGRT) is capable of transferring IgG antibodies from mother to fetus across the placenta. Furthermore, Fc receptors are expressed on a variety of cells, including, e.g., B cells, monocytes, dendritic cells, neutrophils, and certain lymphocytes. For example, U937 cells, a human monocyte cell line, express both FcγRI and FcγRIIA (see e.g., Jones, et al. *J Immunol* 135(5):3348-53 (1985); and Brooks, et al. *J Exp Med* 170:1369-85 (October 1989)). Each receptor referred to herein, includes any known functional form of the receptor, including transcript variants, isoforms and polymorphisms.

Binding of an Ig Fc to its receptor brings these effector cells to sites of the bound antigen, resulting ultimately in a variety of signaling and immune responses, including B cell activation, inflammatory responses, cytotoxic responses, and phagocytic responses. As such, reduced or altered binding of an Ig Fc to its receptor may result in reduced effector functions.

The phrase "antibody-dependent cellular phagocytosis", or "ADCP", relates to an effector function that eliminates (or kills) a target cell by engulfing the target cell rather than inducing cytolysis. ADCP may be an important in vivo mechanism for killing tumor cells. ADCP can be measured by two-color fluorescence flow cytometry methods, for example methods utilizing, e.g. PKH2 (green fluorescent dye) and phycoerythrin-conjugated (red) monoclonal antibodies against different cell surface proteins to differentiate the test cells, thus determining phagocytic activity and rate of phagocytosis. ADCP measurements are well-known in the art. Therapeutic strategies that selectively activate FcγRIIA relative to FcγRIIB may enhance macrophage phagocytic activity (Richards, J O, et al. 2008 *Mol Cancer Ther* 7(8):2517-27). The chimeric Fc-containing antigen-binging proteins and antibodies of the invention bind to and activate human FcγRIIA. In certain circumstances, the antigen-binding proteins and antibodies of the invention bind to human FcγRIIA with higher binding affinity than the antibodies bind FcγRIIB. In some embodiments, the antibody exhibits binding affinity to human FcγRIIA more than about 5-fold stronger than its binding affinity to human FcγRIIB, such binding affinity values expressed in $K_D$. In other embodiments, the antibody exhibits binding affinity to human FcγRIIA more than about 6-, 7-, 8-, 9-, 10-, 11-, 12-, 13-, 14-, 15-, 16-, 17-, 18-, 19-, or 20-fold stronger than its binding affinity to human FcγRIIB.

Biological Characteristics of the Antibodies and Bispecific Antigen-Binding Molecules The present invention includes antibodies and antigen-binding fragments thereof that bind human CD3 and CD20. For example, the present invention includes anti-CD3×CD20 antibodies that bind Jurkat cells (CD3+) and Raji cells (CD20+) with an $EC_{50}$ value of less than about 60 nM, as measured by an in vitro binding assay, e.g., using the assay format as defined in Example 3 herein (e.g., assessing the binding of Jurkat cells or Raji cells to the CD3×CD20 antibodies), or a substantially similar assay. In certain embodiments, the antibodies or antigen-binding fragments of the present invention bind CD3 or CD20 on the surface of the cell (e.g., Jurkat cell and/or Raji cell) with an $EC_{50}$ value of less than about 75 nM, less than about 70 nM, less than about 65 nM, less than about 60 nM, less than about 50 nM, less than about 40 nM, less than about 30 nM, or less than about 25 nM, as measured by an in vitro binding assay, e.g., using the assay format as defined in Example 4 herein, or a substantially similar assay.

The present invention includes bispecific antigen-binding molecules (e.g., bispecific antibodies) which are capable of simultaneously binding to human CD3 and human CD20. According to certain embodiments, the bispecific antigen-binding molecules of the invention specifically interact with cells that express CD3 and/or CD20. The extent to which a bispecific antigen-binding molecule binds cells that express CD3 and/or CD20 can be assessed by fluorescence activated cell sorting (FACS), as illustrated in Example 4 herein. For example, the present invention includes bispecific antigen-binding molecules which specifically bind human T-cell lines which express CD3 (e.g., Jurkat), human B-cell lines which express CD20 (e.g., Raji), and primate T-cells (e.g., cynomolgus peripheral blood mononuclear cells [PBMCs]). The present invention includes bispecific antigen-binding molecules which bind any of the aforementioned cells and cell lines with an $EC_{50}$ value of from about $8.74\times10^{-6}$ to about $5.99\times10^{-8}$, or less, as determined using a FACS assay as set forth in Example 4 or a substantially similar assay.

The present invention also includes antibodies and antigen-binding fragments thereof that bind human CD3 and induce T cell-mediated killing of tumor cells. For example, the present invention includes anti-CD3×CD20 antibodies that induce T cell-mediated killing of tumor cells with an $EC_{50}$ of less than about 60 pM, as measured in an in vitro T cell-mediated tumor cell killing assay, e.g., using the assay format as defined in Example 5 herein (e.g., assessing the extent of Raji tumor cell killing by human PBMCs in the presence of anti-CD3 antibodies), or a substantially similar assay. In certain embodiments, the antibodies or antigen-binding fragments of the present invention induce T cell-mediated tumor cell killing (e.g., PBMC-mediated killing of Raji cells) with an $EC_{50}$ value of less than about 56 pM, less than about 50 pM, less than about 45 pM, less than about 40 pM, less than about 35 pM, less than about 30 pM, less than about 25 pM, less than about 20 pM, less than about 15 pM, less than about 10 pM, less than about 5 pM, or less than about 1 pM, as measured by an in vitro T cell-mediated tumor cell killing assay, e.g., using the assay format as defined in Example 5 herein, or a substantially similar assay.

The present invention also includes antibodies and antigen-binding fragments thereof that bind human CD3/CD20 and induce complement-dependent cytotoxicity (CDC), although to a lesser extent than antibodies having a wild-type IgG Fc domain. For example, the present invention includes anti-CD3×CD20 antibodies that induce CDC killing of Raji or Daudi (CD20-expressing) cells with percent cytotoxicity (% cytotoxicity or % cell lysis) of less than about 50%, as measured in an in vitro T cell-mediated tumor cell killing assay, e.g., using the assay format as defined in Example 6 herein (e.g., assessing the extent of target cell killing (Raji or Daudi) in the presence of complement and anti-CD3×CD20 antibodies), or a substantially similar assay. In certain embodiments, the antibodies or antigen-binding fragments of the present invention induce CDC cell killing (e.g., complement-mediated killing of Raji or Daudi cells) with a percent cytotoxicity of less than about 45%, less than about 40%, less than about 35%, less than about 30%, less than about 25%, less than about 20%, less than about 15%, less than about 10%, less than about 5%, less than about 1%, less than background cytotoxicity, or no detectable cytotoxicity as measured by an in vitro complement-mediated cell killing assay, e.g., using the assay format as defined in Example 6 herein, or a substantially similar assay.

The present invention also includes antibodies and antigen-binding fragments thereof that bind human CD3/CD20 do not significantly induce antibody-dependent cell-mediated cytotoxicity (ADCC) compared to antibodies having a wild-type IgG Fc domain. For example, the present invention includes anti-CD3×CD20 antibodies with no appreciable killing of Raji or Daudi (CD20-expressing) cells with percent cytotoxicity (% cytotoxicity or % cell lysis) of less than about 20% (or less than background cytotoxicity), as measured in an in vitro NK cell-mediated cell killing assay, e.g., using the assay format as defined in Example 7 herein (e.g., assessing the extent of target cell killing (Raji or Daudi) in the presence of NK cells and anti-CD3×CD20 antibodies), or a substantially similar assay. Substantially similar assays may include the presence of NK cells, macrophages, neutrophils, eosinophils or other FcγRIII-expressing cells, including cells expressing variant FcγRIII. In certain embodiments, the antibodies or antigen-binding fragments of the present invention exhibit no detectable ADCC activity (e.g., NK cell or FcγRIII-mediated killing of Raji or Daudi cells) with a percent cytotoxicity of less than about 30%, less than about 25%, less than about 20%, less than about 15%, less than about 10%, less than about 5%, less than about 1%, less than background cytotoxicity, or no detectable cytotoxic activity as measured by an in vitro FcγRIII-mediated cell killing assay, e.g., using the assay format as defined in Example 7 herein, or a substantially similar assay.

According to certain embodiments, the present invention includes antibodies and antigen-binding fragments of antibodies that bind human FcγRIIA (e.g., at 25° C.) with a $K_D$ of less than about 23.5 μM as measured by surface plasmon resonance, e.g., using an assay format as defined in Example 8 herein. In certain embodiments, the antibodies or antigen-binding fragments of the present invention bind FcγRIIA with a $K_D$ of less than about 20.5 μM, less than about 20 μM, less than about 19.3 μM, less than about 18 μM, less than about 17 μM, less than about 16 μM, less than about 15 μM, less than about 10 μM, less than about 9 μM, less than about 8 μM, less than about 7 μM, less than about 6 μM, less than about 5 μM, less than about 4 μM, less than about 3 μM, less than about 2 μM, less than about 1 μM, less than about 900 nM, less than about 800 nM, or less than about 700 nM, as measured by surface plasmon resonance, e.g., using an assay format as defined in Example 8 herein (e.g., mAb-capture or antigen-capture format), or a substantially similar assay.

According to certain embodiments, the present invention includes antibodies and antigen-binding fragments of antibodies that bind human FcγRIIB (e.g., at 25° C.) with a $K_D$ of less than about 233 μM as measured by surface plasmon resonance, e.g., using an assay format as defined in Example 8 herein. In certain embodiments, the antibodies or antigen-binding fragments of the present invention bind FcγRIIB with a $K_D$ of less than about 200 μM, less than about 190 μM, less than about 180 μM, less than about 170 μM, less than about 160 μM, less than about 150 μM, less than about 140 μM, less than about 130 μM, less than about 125 μM, less than about 123 μM, less than about 120 μM, less than about 110 μM, less than about 100 μM, less than about 90 μM, less than about 80 μM, less than about 70 μM, less than about 60 μM, less than about 50 μM, or less than about 40 μM, as measured by surface plasmon resonance, e.g., using an assay format as defined in Example 8 herein (e.g., mAb-capture or antigen-capture format), or a substantially similar assay.

The present invention also includes antibodies and antigen-binding fragments thereof that bind CD3×CD20 with a dissociative half-life (t½) of greater than about 8 days as measured by surface plasmon resonance at 25° C. or 37° C., e.g., using an assay format as defined in Example 9 herein, or a substantially similar assay. In certain embodiments, the antibodies exhibit a t½ of greater than about 5 days, greater than 6 days, greater than about 7 days, greater than about 8 days, greater than about 9 days, greater than about 10 days, greater than about 11 days, greater than about 12 days, greater than about 13 days, greater than about 14 days, greater than about 15 days, or greater than about 20 days, as measured by surface plasmon resonance at 25° C. or 37° C., e.g., using an assay format as defined in Example 9 herein (e.g., mAb-capture or antigen-capture format), or a substantially similar assay.

The present invention also includes anti-CD3/anti-CD20 bispecific antigen-binding molecules do not exhibit substantial activity in one or more assays selected from the group consisting of: (a) inducing PBMC proliferation in vitro; (b) CDC cytotoxicity (see, e.g., Example 6 herein); (d) ADCC (see, e.g., Example 7 herein).

The present invention also includes anti-CD3/anti-CD20 bispecific antigen-binding molecules that exhibit substantial activity in one or more assays selected from the group consisting of: (a) depleting B-cells (e.g., CD45+/CD20+ B-cells) in cynomolgus monkeys (see, e.g., Examples 10 and 11 herein); (b) decreasing B-cell tumor volume (e.g., Raji tumor volume) in immunodeficient mouse models (see, e.g., Example 12A); and (c) regression of tumors in mouse models with established tumors (see, e.g., Example 12B).

The present invention includes anti-CD3/anti-CD20 bispecific antigen-binding molecules which are capable of depleting B cells in a subject (see, e.g., Example 10). For example, according to certain embodiments, anti-CD3/anti-CD20 bispecific antigen-binding molecules are provided, wherein a single administration of the bispecific antigen-binding molecule to a subject (e.g., at a dose of about 1 mg/kg, of about 0.9 mg/kg, of about 0.8 mg/kg, of about 0.7 mg/kg, of about 0.6 mg/kg, of about 0.5 mg/kg, of about 0.4 mg/kg, of about 0.3 mg/kg, of about 0.2 mg/kg, about 0.1 mg/kg, about 0.08 mg/kg, about 0.06 mg/kg about 0.04 mg/kg, about 0.03 mg/kg, about 0.02 mg/kg, about 0.01 mg/kg, or less) causes a reduction in the number of B cells in the subject (e.g., in a blood sample taken from the subject) below detectable levels. In certain embodiments, a single administration of the anti-CD3/anti-CD20 bispecific antigen-binding molecule at a dose of about 0.1 mg/kg causes a reduction in the number of B cells in the subject below detectable levels by about day 7, about day 6, about day 5, about day 4, about day 3, about day 2, or about day 1 after administration of the bispecific antigen-binding molecule to the subject. According to certain embodiments, a single administration of an anti-CD3/anti-CD20 bispecific antigen-binding molecule of the invention, at a dose of about 0.01 mg/kg, causes the number of B-cells to remain below detectable levels until at least about 7 days, 8 days, 9 days, 10 days, 11 days, 12 days, 13 days, 14 days, 15 days, 16 days, 17 days or more, following the administration. As used herein, the expression "below detectable levels" means that no B cells can be directly or indirectly detected in a blood sample drawn from a subject using standard B-cell detection assays, e.g., a FACS assay for B-cell markers, as set forth in Example 10, herein.

The present invention also provides anti-CD3/anti-CD20 bispecific antigen-binding molecules that, when administered to a subject, cause no more than a transient decrease in T cells. For example, anti-CD3/anti-CD20 bispecific antigen-binding molecules are provided that, when administered to a subject at a dose of about 0.01 mg/kg, or about 0.1 mg/kg, or about 1 mg/kg causes the number of T cells to decline at day 1 following administration, but wherein the number of T cells per microliter of blood rebounds at timepoints thereafter (e.g., by about day 2, day 4, day 7, day 14, day 28 or later following the administration). For example the present invention provides an anti-CD3/anti-CD20 bispecific antigen-binding molecule, wherein the number of T cells per microliter of blood drawn from the subject at about day 4 through about day 7 after administration of the antigen binding molecule to the subject at a dose of about 0.01 mg/kg or about 0.1 mg/kg, or about 1 mg/kg is equivalent to or greater than the number of T cells per microliter of blood drawn from the subject prior to administration of the bispecific antigen-binding molecule, as detected using standard T-cell detection assays, e.g., a FACS assay for T-cell markers, as set forth in Example 10, herein.

Epitope Mapping and Related Technologies

The epitope on CD3 or on CD20 to which the antigen-binding molecules of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of a CD3 protein. Alternatively, the epitope may consist of a plurality of non-contiguous amino acids (or amino acid sequences) of CD3 or CD20. The antibodies of the invention may interact with amino acids contained within a single CD3 chain (e.g., CD3-epsilon, CD3-delta or CD3-gamma), or may interact with amino acids on two or more different CD3 chains. The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Various techniques known to persons of ordinary skill in the art can be used to determine whether an antigen-binding domain of an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, 2004, *Methods Mol Biol* 248:443-463), and peptide cleavage analysis. In addition, methods such as epitope excision, epitope extraction and chemical modification of antigens can be employed (Tomer, 2000, *Protein Science* 9:487-496). Another method that can be used to identify the amino acids within a polypeptide with which an antigen-binding domain of an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

The present invention further includes anti-CD3 antibodies that bind to the same epitope as any of the specific exemplary antibodies described herein (e.g. antibodies comprising any of the amino acid sequences as set forth in Table 1 herein). Likewise, the present invention also includes anti-CD3 antibodies that compete for binding to CD3 with any of the specific exemplary antibodies described herein (e.g. antibodies comprising any of the amino acid sequences as set forth in Table 1 herein).

The present invention also includes bispecific antigen-binding molecules comprising a first antigen-binding domain that specifically binds human CD3, and a second antigen binding domain that specifically binds human CD20, wherein the first antigen-binding domain binds to the same epitope on CD3 as a specific exemplary CD3-specific antigen-binding domains described herein, and/or wherein the second antigen-binding domain binds to the same epitope on CD20 as a specific exemplary CD20-specific antigen-binding domains described herein.

Likewise, the present invention also includes bispecific antigen-binding molecules comprising a first antigen-binding domain that specifically binds human CD3, and a second antigen binding domain that specifically binds human CD20, wherein the first antigen-binding domain competes for binding to CD3 with any of the specific exemplary CD3-specific antigen-binding domains described herein, and/or wherein the second antigen-binding domain competes for binding to CD20 with any of the specific exemplary CD20-specific antigen-binding domains described herein.

In one aspect, the present invention includes a bispecific antibody in which a first antigen-binding domain competes for binding to human CD3 with a reference antigen-binding protein, which comprises three heavy chain complementarity determining regions (A1-HCDR1, A1-HCDR2 and A1-HCDR3) and three light chain complementarity determining regions (A1-LCDR1, A1-LCDR2 and A1-LCDR3), wherein (i) A1-HCDR1 comprises the amino acid sequence of SEQ ID NO: 12; (ii) A1-HCDR2 comprises the amino acid sequence of SEQ ID NO: 14; (iii) A1-HCDR3 comprises the amino acid sequence of SEQ ID NO: 16; (iv) A1-LCDR1 comprises the amino acid sequence of SEQ ID NO: 20; (v) A1-LCDR2 comprises the amino acid sequence of SEQ ID NO: 22; and (vi) A1-LCDR3 comprises the amino acid sequence of SEQ ID NO: 24. In some cases, the bispecific antibody comprises a first antigen-binding domain that competes for binding to human CD3 with a reference antigen-binding protein which comprises (i) the heavy chain variable region (HCVR) amino acid sequence of SEQ ID NO: 10, and (ii) the light chain variable region (LCVR) amino acid sequence of SEQ ID NO: 18.

In another aspect, the present invention includes a bispecific antibody in which a second antigen-binding domain competes for binding to human CD20 with a reference antigen-binding protein which comprises three heavy chain complementarity determining regions (A2-HCDR1, A2-HCDR2 and A2-HCDR3) and three light chain complementarity determining regions (A2-LCDR1, A2-LCDR2 and A2-LCDR3), wherein (i) A2-HCDR1 comprises the amino acid sequence of SEQ ID NO: 4; (ii) A2-HCDR2 comprises the amino acid sequence of SEQ ID NO: 6; (iii) A2-HCDR3 comprises SEQ ID NO: 8; (iv) A2-LCDR1 comprises the amino acid sequence of SEQ ID NO: 20; (v) A2-LCDR2 comprises the amino acid sequence of SEQ ID NO: 22; and (vi) A2-LCDR3 comprises the amino acid sequence of SEQ ID NO: 24. In some cases, the bispecific antibody comprises a second antigen-binding domain that competes for binding to human CD20 with a reference antigen-binding protein which comprises (i) a heavy chain variable region (HCVR) comprising the amino acid sequence of SEQ ID NO: 2, and (ii) a light chain variable region (LCVR) comprising the amino acid sequence of SEQ ID NO: 18.

In another aspect, the present invention includes a bispecific antibody having a first antigen-binding domain that competes for binding to human CD3 with a reference antigen-binding protein which comprises (i) a heavy chain variable region (HCVR) comprising the amino acid sequence of SEQ ID NO: 10, and (ii) a light chain variable region (LCVR) comprising the amino acid sequence of SEQ ID NO: 18; and having a second antigen-binding domain that competes for binding to human CD20 with a reference antigen-binding protein which comprises (iii) a heavy chain variable region (HCVR) comprising the amino acid sequence of SEQ ID NO:2, and a light chain variable region (LCVR) comprising the amino acid sequence of SEQ ID NO: 18.

One can easily determine whether a particular antigen-binding molecule (e.g., antibody) or antigen-binding domain thereof binds to the same epitope as, or competes for binding with, a reference antigen-binding molecule of the present invention by using routine methods known in the art. For example, to determine if a test antibody binds to the same epitope on CD3 (or CD20) as a reference bispecific antigen-binding molecule of the present invention, the reference bispecific molecule is first allowed to bind to a CD3 protein (or CD20 protein). Next, the ability of a test antibody to bind to the CD3 (or CD20) molecule is assessed. If the test antibody is able to bind to CD3 (or CD20) following saturation binding with the reference bispecific antigen-binding molecule, it can be concluded that the test antibody binds to a different epitope of CD3 (or CD20) than the reference bispecific antigen-binding molecule. On the other hand, if the test antibody is not able to bind to the CD3 (or CD20) molecule following saturation binding with the reference bispecific antigen-binding molecule, then the test antibody may bind to the same epitope of CD3 (or CD20) as the epitope bound by the reference bispecific antigen-binding molecule of the invention. Additional routine experimentation (e.g., peptide mutation and binding analyses) can then be carried out to confirm whether the observed lack of binding of the test antibody is in fact due to binding to the same epitope as the reference bispecific antigen-binding molecule or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antigen-binding proteins bind to the same (or overlapping) epitope if, e.g., a 1-, 5-, 10-, 20- or 100-fold excess of one antigen-binding protein inhibits binding of the other by at least 50% but preferably 75%, 90% or even 99% as measured in a competitive binding assay (see, e.g., Junghans et al., *Cancer Res.* 1990:50:1495-1502). Alternatively, two antigen-binding proteins are deemed to bind to the same epitope if essentially all amino acid mutations in the antigen that reduce or eliminate binding of one antigen-binding protein reduce or eliminate binding of the other. Two antigen-binding proteins are deemed to have "overlapping epitopes" if only a subset of the amino acid mutations that reduce or eliminate binding of one antigen-binding protein reduce or eliminate binding of the other.

To determine if an antibody or antigen-binding domain thereof competes for binding with a reference antigen-binding molecule, the above-described binding methodology is performed in two orientations: In a first orientation, the reference antigen-binding molecule is allowed to bind to a CD3 protein (or CD20 protein) under saturating conditions followed by assessment of binding of the test antibody to the CD3 (or CD20) molecule. In a second orientation, the test antibody is allowed to bind to a CD3 (or CD20) molecule under saturating conditions followed by assessment of binding of the reference antigen-binding molecule to the CD3 (or CD20) molecule. If, in both orientations, only the first (saturating) antigen-binding molecule is capable of binding to the CD3 (or CD20) molecule, then it is concluded that the test antibody and the reference antigen-binding molecule compete for binding to CD3 (or CD20). As will be appreciated by a person of ordinary skill in the art, an antibody that competes for binding with a reference antigen-binding molecule may not necessarily bind to the same epitope as the reference antibody, but may sterically block binding of the reference antibody by binding an overlapping or adjacent epitope.

Preparation of Antigen-Binding Domains and Construction of Bispecific Molecules

Antigen-binding domains specific for particular antigens can be prepared by any antibody generating technology known in the art. Once obtained, two different antigen-binding domains, specific for two different antigens (e.g., CD3 and CD20), can be appropriately arranged relative to one another to produce a bispecific antigen-binding molecule of the present invention using routine methods. (A discussion of exemplary bispecific antibody formats that can be used to construct the bispecific antigen-binding molecules of the present invention is provided elsewhere herein). In certain embodiments, one or more of the individual components (e.g., heavy and light chains) of the multispecific antigen-binding molecules of the invention are derived from chimeric, humanized or fully human antibodies. Methods for making such antibodies are well known in the art. For example, one or more of the heavy and/or light chains of the bispecific antigen-binding molecules of the present invention can be prepared using VELOCIMMUNE™ technology. Using VELOCIMMUNE™ technology (or any other human antibody generating technology), high affinity chimeric antibodies to a particular antigen (e.g., CD3 or CD20) are initially isolated having a human variable region and a mouse constant region. The antibodies are characterized and selected for desirable characteristics, including affinity, selectivity, epitope, etc. The mouse constant regions are replaced with a desired human constant region to generate fully human heavy and/or light chains that can be incorporated into the bispecific antigen-binding molecules of the present invention.

Genetically engineered animals may be used to make human bispecific antigen-binding molecules. For example, a genetically modified mouse can be used which is incapable of rearranging and expressing an endogenous mouse immunoglobulin light chain variable sequence, wherein the mouse expresses only one or two human light chain variable domains encoded by human immunoglobulin sequences operably linked to the mouse kappa constant gene at the endogenous mouse kappa locus. Such genetically modified mice can be used to produce fully human bispecific antigen-binding molecules comprising two different heavy chains that associate with an identical light chain that comprises a variable domain derived from one of two different human light chain variable region gene segments. (See, e.g., US 2011/0195454 for a detailed discussion of such engineered mice and the use thereof to produce bispecific antigen-binding molecules).

Bioequivalents

The present invention encompasses antigen-binding molecules having amino acid sequences that vary from those of the exemplary molecules disclosed herein but that retain the ability to bind CD3 and/or CD20. Such variant molecules may comprise one or more additions, deletions, or substitutions of amino acids when compared to parent sequence, but exhibit biological activity that is essentially equivalent to that of the described bispecific antigen-binding molecules.

The present invention includes antigen-binding molecules that are bioequivalent to any of the exemplary antigen-binding molecules set forth herein. Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antigen-binding proteins will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antigen-binding protein.

Bioequivalent variants of the exemplary bispecific antigen-binding molecules set forth herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antigen-binding proteins may include variants of the exemplary bispecific antigen-binding molecules set forth herein comprising amino acid changes which modify the glycosylation characteristics of the molecules, e.g., mutations which eliminate or remove glycosylation.

Species Selectivity and Species Cross-Reactivity

According to certain embodiments of the invention, antigen-binding molecules are provided which bind to human CD3 but not to CD3 from other species. Also provided are antigen-binding molecules which bind to human CD20 but not to CD20 from other species. The present invention also includes antigen-binding molecules that bind to human CD3 and to CD3 from one or more non-human species; and/or antigen-binding molecules that bind to human CD20 and to CD20 from one or more non-human species.

According to certain exemplary embodiments of the invention, antigen-binding molecules are provided which bind to human CD3 and/or human CD20 and may bind or not bind, as the case may be, to one or more of mouse, rat, guinea pig, hamster, gerbil, pig, cat, dog, rabbit, goat, sheep, cow, horse, camel, cynomolgus, marmoset, rhesus or chimpanzee CD3 and/or CD20. For example, in a particular exemplary embodiment of the present invention bispecific antigen-binding molecules are provided comprising a first antigen-binding domain that binds human CD3 and cynomologous CD3, and a second antigen-binding domain that specifically binds human CD20.

Immunoconjugates

The present invention encompasses antigen-binding molecules conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art, (see for example, WO 05/103081).

Therapeutic Formulation and Administration

As used herein, the terms "effective amount" and "therapeutically effective amount" refer to the quantity of the active therapeutic agent sufficient to yield a desired therapeutic response without undue adverse side effects such as toxicity, irritation, or allergic response. The specific "effective amount" will, obviously, vary with such factors as the particular condition being treated, the physical condition of the patient, the type of animal being treated, the duration of the treatment, the nature of concurrent therapy (if any), and the specific formulations employed and the structure of the compounds or its derivatives. In this case, an amount would be deemed therapeutically effective if it resulted in one or more of, but not limited to, the following: (a) the inhibition of tumor growth (e.g., B-cell cancer); and (b) the reversal or stabilization of a B-cell cancer.

The dose of antigen-binding molecule administered to a patient may vary depending upon the age and the size of the patient, target disease, conditions, route of administration, and the like. The preferred dose is typically calculated according to body weight or body surface area. When a bispecific antigen-binding molecule of the present invention is used for therapeutic purposes in an adult patient, it may be advantageous to intravenously administer the bispecific antigen-binding molecule of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering a bispecific antigen-binding molecule may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antigen-Binding Molecules

The present invention includes methods comprising administering to a subject in need thereof a therapeutic composition comprising an anti-CD3 antibody or a bispecific antigen-binding molecule that specifically binds CD3 and a target antigen (e.g., CD20). The therapeutic composition can comprise any of the antibodies or bispecific antigen-binding molecules as disclosed herein and a pharmaceutically acceptable carrier or diluent. As used herein, the expression "a subject in need thereof" means a human or non-human animal that exhibits one or more symptoms or indicia of cancer (e.g., a subject expressing a tumor or suffering from any of the cancers mentioned herein below), or who otherwise would benefit from an inhibition or reduction in CD20 activity or a depletion of CD20+ B cells or a regression of CD20+ B cell tumors.

The antibodies and bispecific antigen-binding molecules of the invention (and therapeutic compositions comprising the same) are useful, inter alia, for treating any disease or disorder in which stimulation, activation and/or targeting of an immune response would be beneficial. In particular, the anti-CD3/anti-CD20 bispecific antigen-binding molecules of the present invention may be used for the treatment, prevention and/or amelioration of any disease or disorder associated with or mediated by CD20 expression or activity or the proliferation of CD20+ B cells. The mechanism of action by which the therapeutic methods of the invention are achieved include killing of the cells expressing CD20 in the presence of effector cells, for example, by apoptosis, phagocytosis, or by a combination of two or more of these mechanisms or similar cytotoxic mechanisms. Cells expressing CD20 which can be inhibited or killed using the bispecific antigen-binding molecules of the invention include, for example, tumorigenic B cells.

Reduction of tumor burden or tumor regression includes the partial or complete disappearance of a tumor or tumors in a subject. It is understood that tumor regression represents a trend toward a lower tumor burden or less severe state of disease. As such, regression is a progressive decline elimination of measurable malignancies in the body, including decline in tumor size and/or decline in number of tumors. Reduction of tumor development includes a partial or complete inhibition or suppression of further or new tumor growth.

The antigen-binding molecules of the present invention may be used to target and treat, e.g., primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the bispecific antigen-binding molecules of the invention are used to treat one or more of the following cancers: renal cell carcinoma, pancreatic carcinoma, breast cancer, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, or melanoma. According to certain exemplary embodiments, the bispecific antigen-binding molecules of the present invention are used to treat a B cell cancer (e.g., Hodgkin's lymphoma, non-Hodgkin's lymphoma [NHL], precursor B cell lymphoblastic leukemia/lymphoma, mature B cell neoplasms, B cell chronic lymphocytic leukemia/small lymphocytic lymphoma, B cell prolymphocytic leukemia, lymphoplasmacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma).

The anti-CD3/anti-CD20 bispecific antigen-binding molecules of the present invention are administered in an amount sufficient to reduce tumor burden, produce tumor regression, inhibit tumor growth or reduce tumor development in the subject. In some exemplary embodiments of the invention, the administered amount is between about 0.001 mg/kg to about 1 mg/kg. In other embodiments, the administered amount is about 0.4 mg/kg. In other embodiments, the administered amount is about 0.04 mg/kg. In still other embodiments, the administered amount is about 0.004 mg/kg.

According to certain embodiments of the present invention, the antigen-binding molecules are useful for treating a patient afflicted with a B-cell lymphoma (e.g., NHL) that is resistant to, or incompletely responsive to anti-CD20 therapy alone (e.g., resistant to rituximab therapy). According to other related embodiments of the invention, methods are provided comprising administering an anti-CD3/anti-CD20 bispecific antigen-binding molecule as disclosed herein to a patient who is afflicted with a B-cell lymphoma (e.g., NHL) that is refractory to anti-CD20 therapy (e.g., a patient with a rituximab-refractory tumor or with relapsed or refractory B-cell lymphoma). Analytic/diagnostic methods known in the art, such as tumor scanning, etc., may be used to ascertain whether a patient harbors as tumor that is resistant to, incompletely responsive to, or refractory to anti-CD20 therapy alone.

The present invention also includes methods for treating residual cancer in a subject. As used herein, the term "residual cancer" means the existence or persistence of one or more cancerous cells in a subject following treatment with an anti-cancer therapy.

According to certain aspects, the present invention provides methods for treating a disease or disorder associated with CD20 expression (e.g., B cell lymphoma) comprising administering one or more of the bispecific antigen-binding molecules described elsewhere herein to a subject after the subject has received anti-CD20 mono-therapy (e.g., after administration of a pharmaceutical composition comprising an anti-CD20 antibody such as rituximab). For example, the present invention includes methods for treating B cell lymphoma comprising administering an anti-CD3/anti-CD20 bispecific antigen-binding molecule to a patient 1 day, 2 days, 3 days, 4 days, 5 days, 6 days, 1 week, 2 weeks, 3 weeks or 4 weeks, 2 months, 4 months, 6 months, 8 months, 1 year, or more after the subject has received anti-CD20 mono-therapy (e.g., rituximab treatment or an equivalent treatment thereof).

Combination Therapies and Formulations

The present invention provides methods which comprise administering a pharmaceutical composition comprising any of the exemplary antibodies and bispecific antigen-binding molecules described herein in combination with one or more additional therapeutic agents. Exemplary additional therapeutic agents that may be combined with or administered in combination with an antigen-binding molecule of the present invention include, e.g., an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2, anti-ErbB3 or anti-ErbB4 antibody or small molecule inhibitor of ErbB2, ErbB3 or ErbB4 activity), an antagonist of EGFRvIII (e.g., an antibody that specifically binds EGFRvIII), a cMET anagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody), a VEGF antagonist (e.g., a VEGF-Trap, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354), an Ang2 antagonist (e.g., an anti-Ang2 antibody disclosed in US 2011/0027286 such as H1H685P), a FOLH1 antagonist (e.g., an anti-FOLH1 antibody), a PRLR antagonist (e.g., an anti-PRLR antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin antibody), an anti-CTLA4 antibody (e.g. ipilimumab (MDX-010)), a monovalent CD20 antagonist (e.g., a monovalent anti-CD20 antibody such as rituximab), etc.

Other agents that may be beneficially administered in combination with the antigen-binding molecules of the invention include immune activators or inhibitors. Certain immune activators or inhibitors are cytokine activators or inhibitors, including small-molecule compounds and antibodies that bind to cytokines such as IL-1, IL-2, IL-3, IL-4, IL-5, IL-6, IL-8, IL-9, IL-11, IL-12, IL-13, IL-17, IL-18, or to their respective receptors. The pharmaceutical compositions of the present invention (e.g., pharmaceutical compositions comprising an anti-CD3/anti-CD20 bispecific antigen-binding molecule as disclosed herein) may also be administered as part of a therapeutic regimen comprising one or more therapeutic combinations selected from "ICE": ifosfamide (e.g., Ifex®), carboplatin (e.g., Paraplatin®), etoposide (e.g., Etopophos®, Toposar®, VePesid®, VP-16); "DHAP": dexamethasone (e.g., Decadron®), cytarabine (e.g., Cytosar-U®, cytosine arabinoside, ara-C), cisplatin (e.g., Platinol®-AQ); and "ESHAP": etoposide (e.g., Etopophos®, Toposar®, VePesid®, VP-16), methylprednisolone (e.g., Medrol®), high-dose cytarabine, cisplatin (e.g., Platinol®-AQ).

The present invention also includes therapeutic combinations comprising any of the antigen-binding molecules mentioned herein and an inhibitor of one or more of VEGF, Ang2, DLL4, EGFR, ErbB2, ErbB3, ErbB4, EGFRvIII, cMet, IGF1R, B-raf, PDGFR-α, PDGFR-β, FOLH1, PRLR, STEAP1, STEAP2, TMPRSS2, MSLN, CA9, uroplakin, or any of the aforementioned cytokines, wherein the inhibitor is an aptamer, an antisense molecule, a ribozyme, an siRNA, a peptibody, a nanobody or an antibody fragment (e.g., Fab fragment; F(ab')$_2$ fragment; Fd fragment; Fv fragment; scFv; dAb fragment; or other engineered molecules, such as diabodies, triabodies, tetrabodies, minibodies and minimal recognition units). The antigen-binding molecules of the invention may also be administered and/or co-formulated in combination with antivirals, antibiotics, analgesics, corticosteroids and/or NSAIDs. The antigen-binding molecules of the invention may also be administered as part of a treatment regimen that also includes radiation treatment and/or conventional chemotherapy.

The additional therapeutically active component(s) may be administered just prior to, concurrent with, or shortly after the administration of an antigen-binding molecule of the present invention (for purposes of the present disclosure, such administration regimens are considered the administration of an antigen-binding molecule "in combination with" an additional therapeutically active component).

The present invention includes pharmaceutical compositions in which an antigen-binding molecule of the present invention is co-formulated with one or more of the additional therapeutically active component(s) as described elsewhere herein.

Administration Regimens

According to certain embodiments of the present invention, multiple doses of an antigen-binding molecule (e.g., an anti-CD3 antibody or a bispecific antigen-binding molecule that specifically binds CD20 and CD3) may be administered to a subject over a defined time course. The methods according to this aspect of the invention comprise sequentially administering to a subject multiple doses of an antigen-binding molecule of the invention. As used herein, "sequentially administering" means that each dose of an antigen-binding molecule is administered to the subject at a different point in time, e.g., on different days separated by a predetermined interval (e.g., hours, days, weeks or months). The present invention includes methods which comprise sequentially administering to the patient a single initial dose of an antigen-binding molecule, followed by one or more secondary doses of the antigen-binding molecule, and optionally followed by one or more tertiary doses of the antigen-binding molecule.

The terms "initial dose," "secondary doses," and "tertiary doses," refer to the temporal sequence of administration of the antigen-binding molecule of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the antigen-binding molecule, but generally may differ from one another in terms of frequency of administration. In certain embodiments, however, the amount of an antigen-binding molecule contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient any number of secondary and/or tertiary doses of an antigen-binding molecule (e.g., a bispecific antigen-binding molecule that specifically binds CD20 and CD3). For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-CD3×CD20 antibodies of the present invention may also be used to detect and/or measure CD3, or CD3-expressing cells in a sample, e.g., for diagnostic purposes. For example, an anti-CD3×CD20 antibody, or fragment thereof, may be used to diagnose a condition or disease characterized by aberrant expression (e.g., over-expression, under-expression, lack of expression, etc.) of CD3. Exemplary diagnostic assays for CD3 may comprise, e.g., contacting a sample, obtained from a patient, with an anti-CD3× CD20 antibody of the invention, wherein the antibody is labeled with a detectable label or reporter molecule. Alternatively, an unlabeled anti-CD3×CD20 antibody can be used in diagnostic applications in combination with a secondary antibody which is itself detectably labeled. The detectable label or reporter molecule can be a radioisotope, such as $^3$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure CD3 in a sample include enzyme-linked immunosorbent assay (ELISA), radioimmunoassay (RIA), and fluorescence-activated cell sorting (FACS).

The anti-CD3×CD20 antibodies of the present invention may also be used to detect and/or measure CD20, or CD20-expressing cells in a sample, or to diagnose a condition or disease characterized by aberrant expression (e.g., over-expression, under-expression, lack of expression, etc.) of CD20, analogously.

Samples that can be used in CD3 or CD20 diagnostic assays according to the present invention include any tissue or fluid sample obtainable from a patient which contains detectable quantities of CD3 and/or CD20 protein, or fragments thereof, under normal or pathological conditions. Generally, levels of CD3 or CD20 in a particular sample obtained from a healthy patient (e.g., a patient not afflicted with a disease or condition associated with abnormal CD3 or CD20 levels or activity) will be measured to initially establish a baseline, or standard, level of CD3 or CD20. This baseline level of CD3 or CD20 can then be compared against the levels of CD3 measured in samples obtained from individuals suspected of having a CD3- or CD20-related disease or condition, respectively.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Anti-CD3 and Anti-CD20 Antibodies

Several methods are known for isolating anti-CD3 or anti-CD20 antibodies. Fully human anti-CD3 antibodies used in the following examples were isolated directly from antigen-positive B cells without fusion to myeloma cells, as described in US 2007/0280945A1.

Additional examples of anti-CD3 antibodies may be used in the methods, and description of such antibodies and the biological properties of such anti-CD3 antibodies are described in PCT International Application No. PCT/US13/60511, filed on Sep. 19, 2013, which is herein incorporated by reference in its entirety. Exemplary anti-CD20 antibodies and biological properties of such anti-CD20 antibodies are described in U.S. Pat. No. 7,879,984 and PCT International Application No. PCT/US13/60511, filed on Sep. 19, 2013, each incorporated by reference herein.

The anti-CD20 antibody and its method of making the antibody used to construct the bispecific antibodies of this example is as described in U.S. Pat. No. 7,879,984.

The amino acid sequence identifiers of the heavy and light chain variable regions and CDRs used to construct the anti-CD3 antigen-binding arm and anti-CD20 binding arm of the bispecific antibodies invention are set forth in Table 1. The corresponding nucleic acid sequence identifiers are set forth in Table 2.

TABLE 1

Amino Acid Sequence Identifiers (SEQ ID NOs)

| Antibody Designation | SEQ ID NOs: | | | | | | | |
|---|---|---|---|---|---|---|---|---|
|  | HCVR | HCDR1 | HCDR2 | HCDR3 | LCVR | LCDR1 | LCDR2 | LCDR3 |
| Anti-CD20 | 2 | 4 | 6 | 8 | 18 | 20 | 22 | 24 |
| Anti-CD3 | 10 | 12 | 14 | 16 | 18 | 20 | 22 | 24 |

TABLE 2

Nucleic Acid Sequence Identifiers (SEQ ID NOs)

| Antibody Designation | SEQ ID NOs: | | | | | | | |
|---|---|---|---|---|---|---|---|---|
|  | HCVR | HCDR1 | HCDR2 | HCDR3 | LCVR | LCDR1 | LCDR2 | LCDR3 |
| Anti-CD20 | 1 | 3 | 5 | 7 | 17 | 19 | 21 | 23 |
| Anti-CD3 | 9 | 11 | 13 | 15 | 17 | 19 | 21 | 23 |

Example 2. Generation of Bispecific Antibodies that Bind CD3 and CD20

Bispecific antibodies comprising an anti-CD3-specific binding domain and an anti-CD20-specific binding domain were constructed with the above sequences using standard methodologies wherein a heavy chain and a cognate light chain from an anti-CD3 antibody were combined with a heavy chain from an anti-CD20 antibody.

As such, the bispecific antibodies created in accordance with the present Example comprise two separate antigen-binding domains (i.e., binding arms). The first antigen-binding domain comprises a heavy chain variable region derived from an anti-CD20 antibody ("CD20-VH"), paired with a light chain variable region derived from an anti-CD3 antibody ("CD3-VL"). The CD20-VH/CD3-VL pairing creates an antigen-binding domain that specifically recognizes CD20. The second antigen-binding domain comprises a heavy chain variable region derived from an anti-CD3 antibody ("CD3-VH"), paired with a light chain variable region derived from an anti-CD3 antibody ("CD3-VL"). The CD3-VH/CD3-VL pairing creates an antigen-binding domain that specifically recognizes CD3. The same CD20-VH was used in all bispecific antibodies created in this example and is designated "CD20-VH-A".

The wild-type heavy chain constant domain (CH) for each heavy chain was replaced with a chimeric CH by recombinant techniques. The CH of one binding arm (e.g. anti-CD3 binding arm) contains a mutation in the CH3 region of the CH which facilitates isolation of the bispecific.

A summary of the component parts of the various bispecific antibodies made in accordance with this Example is set forth in Table 3 and Table 4.

Tables 5 and 6 set out the amino acid sequence identifiers for the various heavy chain variable regions (Table 5) and light chain variable regions (Table 6) with their corresponding CDRs of the bispecific antibodies of this Example.

TABLE 5

| Heavy Chain Amino Acid Sequence Identifiers | | | | | |
|---|---|---|---|---|---|
| Heavy Chain Identifier | Heavy Chain Variable Region (HCVR) | HCDR1 | HCDR2 | HCDR3 | Heavy Chain Constant Region (CH) |
| CD20-VH-CH-A | 2 | 4 | 6 | 8 | 26 or 28 or 30 or 32 |
| CD3-VH-CH-A | 10 | 12 | 14 | 16 | |

TABLE 6

| Light Chain Amino Acid Sequence Identifiers | | | | |
|---|---|---|---|---|
| Light Chain Identifier | Light Chain Variable Region (LCVR) | LCDR1 | LCDR2 | LCDR3 |
| CD3-VL-A | 18 | 20 | 22 | 24 |

In addition, Tables 7 and 8 set out the sequence identifiers for the nucleotide sequences encoding the various heavy chain variable regions (Table 7), heavy chain constant regions, and light chain variable regions (Table 8) with their corresponding CDRs of the bispecific antibodies of this Example.

TABLE 3

| | Amino Acid Sequence Identifiers | | | | | |
|---|---|---|---|---|---|---|
| | Anti-CD20 Antigen-Binding Domain | | | Anti-CD3 Antigen-Binding Domain | | |
| Bispecific Antibody Name | Heavy Chain Variable Region CD20-VH-A | Heavy chain Constant region CH | Light Chain Variable Region CD3-VL-A | Heavy Chain Variable Region CD3-VH-A | Heavy chain Constant region CH | Light Chain Variable Region CD3-VL-A |
| Antibody 1 | 2 | 26 | 18 | 10 | 28 | 18 |
| Antibody 2 | 2 | 30 | 18 | 10 | 32 | 18 |

TABLE 4

| | Nucleic Acid Sequence Identifiers | | | | | |
|---|---|---|---|---|---|---|
| | Anti-CD20 Antigen-Binding Domain | | | Anti-CD3 Antigen-Binding Domain | | |
| Bispecific Antibody Name | Heavy Chain Variable Region CD20-VH-A | Heavy chain Constant region CH | Light Chain Variable Region CD3-VL-A | Heavy Chain Variable Region CD3-VH-A | Heavy chain Constant region CH | Light Chain Variable Region CD3-VL-A |
| Antibody 1 | 1 | 25 | 17 | 9 | 27 | 17 |
| Antibody 2 | 1 | 29 | 17 | 9 | 31 | 17 |

TABLE 7

Heavy Chain Nucleic Acid Sequence Identifiers

| Heavy Chain Identifier | Heavy Chain Variable Region (HCVR) | HCDR1 | HCDR2 | HCDR3 | Heavy Chain Constant Region (HCVR) |
|---|---|---|---|---|---|
| CD20-VH-A | 1 | 3 | 5 | 7 | 25 or 27 or 29 or 31 |
| CD3-VH-A | 9 | 11 | 13 | 15 | |

TABLE 8

Light Chain Nucleic Acid Sequence Identifiers

| Light Chain Identifier | Light Chain Variable Region (LCVR) | LCDR1 | LCDR2 | LCDR3 |
|---|---|---|---|---|
| CD3-VL-A | 17 | 19 | 21 | 23 |

In addition to the bispecific antibodies described above, the following control antibodies were also used in certain of the experiments set out in the Examples that follow:

Control Antibody 1:
Monoclonal antibody "OKT-3" against human T-cell surface antigens as set forth in U.S. Pat. No. 4,361,549 and available from hybridoma CRL-8001 (American Type Culture Collection, Manassas, Va.).

Control Antibody 2:
Antibody "SP34" reactive against the epsilon chain of the T3 complex on human T lymphocyte cells, available from BD Pharmagen, Cat #55052.

Control Antibody 3:
Anti-CD20 therapeutic antibody, with heavy and light chain sequences of Rituxan® (Rituximab) as disclosed in U.S. Pat. No. 5,736,137.

(Control) Antibody 4:
Also known as CD3×CD20 antibody-wild-type Fc (wtFc), this antibody was made analogously to the above methods having an anti-CD20 arm comprising HCVR/LCVR amino acid sequence pair of SEQ ID NOs: 2/18 (HCDR1-HCDR2-HCDR3-LCDR1-LCDR2-LCDR3 amino acid sequences of SEQ ID NOs: 4-6-8-20-22-24), and a wild-type IgG1 CH region (SEQ ID NO: 45); and an anti-CD3 arm comprising HCVR/LCVR amino acid sequence pair of SEQ ID NOs: 10/18 (HCDR1-HCDR2-HCDR3-LCDR1-LCDR2-LCDR3 amino acid sequences of SEQ ID NOs: 12-14-16-20-22-24), and a wild-type IgG1 CH region with 2 amino acid modifications (SEQ ID NO: 48) in the CH3 domain for ease of isolation. CD3×CD20 antibody-wtFc (Antibody 4) may be referred to as a matched control antibody having a wild-type IgG1 Fc domain (i.e. matched to the antigen-binding domains of the CD3×CD20-chimeric Fc antibodies of the invention), for the purposes of comparing antibody effector functions, or other properties, to antibodies having different Fc domain sequences or structure.

Control Antibody 5: Anti-FeID1 monoclonal antibody binds a feline antigen with no cross-reactivity to human CD20 or CD3. This IgG1 non-specific antibody control was obtained by methods described in PCT Publication No. WO2013/166236, published on Nov. 7, 2013.

Control Antibody 6: Anti-FeID1 antigen-binding domain, as described in PCT Publication No. WO2013/166236, was engineered as described herein to contain a chimeric IgG4 Fc domain analogously to Ab 1. Control Ab 6 has no cross-reactivity to human CD20 or CD3, but has similar effector function to Ab 1.

Example 3. Chimeric Heavy Chain Construction

Generating the chimeric heavy chains, for example chimeric CH IgG4 (SEQ ID NO: 26) and a chimeric CH IgG1 (SEQ ID NO: 30), was done using standard cloning techniques. First, the chimeric IgG4 CH was generated through a two-step PCR amplification process. Two PCR fragments, Fragment 1 and 2, were amplified using a starting vector construct pR001 containing a wild-type hIgG4 CH DNA using primer pairs flanking the CH region, P1-P2 and P3-P4, respectively. See Table 9 below.) The primers introduced both the desired IgG2 lower hinge sequence (which encodes SEQ ID NO: 52) and the flanking restriction sites into the fragments. These two fragments were then joined using PCR primers P2 and P4. The resulting sequence was inserted into pR001 via Xho1-Not1 restriction sites generating a vector construct pR002 that contains a chimeric IgG4 CH having an IgG2 lower hinge sequence. The sequence was confirmed using primers P10 and P11

In addition, a chimeric IgG1 CH was generated through multiple step PCR amplification. Fragment 1a was generated using primers P2 and P5 (see Table 9 below) from template pR85503 (which contains a wild-type human IgG1 CH DNA). Fragment 2a was amplified with primers P6 and P8 using pR002 (containing the chimeric IgG4 CH DNA) as a template. Fragment 3 was made using primers P7 and P9 from template pR003 (wild-type hIgG1 CH DNA; SEQ ID NO: 45). Fragments 1a and 2a were joined using primers P2 and P8, which generated Fragment 4. Joining Fragments 2a and 3 using primers P6 and P9 created Fragment 5. Fragment 4 and 5 were then fused using primers P2 and P9. The resulting sequence was inserted into pR001 via Xho1-Not1 restriction sites generating a construct pR004 that has an IgG1 constant region with the IgG2 lower hinge and IgG4 CH2 domain. The sequence was confirmed using primers P10 and P11.

TABLE 9

Primers for PCR generation of chimeric $C_H$ nucleic acid constructs

| Primer name | Primer Sequence (SEQ ID NO) |
|---|---|
| P1 | 5'-TTCGCGCAGCTTAGGTTTATGCCA GGGGGGACGGGTGGCACGGGTCGTGGT GGACACCGT-3' (antisense) (SEQ ID NO: 63) |
| P2 | 5'-AAGCTTATACTCGAGCTCTAGATT GGGAACCCGGGTCTCT-3' (SEQ ID NO: 64) |
| P3 | 5'-CCCACCGTGCCCAGCACCACCTGT GGCAGGACCATCAGTCTTCCTGTTCCC CCCAAAA-3' (SEQ ID NO: 65) |
| P4 | 5'-TGTGTCTTCAGGGAGAGGGACAGA GACCCATTTACTCGCCGGCG-3' (antisense)(SEQ ID NO: 66) |
| P5 | 5'-CTCGGGTTTAGAACACTGTTTTGA GTGTGTACGGGTGGCACGGGTCGTGGT GGACACCGT-3' (antisense) (SEQ ID NO: 67) |

TABLE 9-continued

Primers for PCR generation of chimeric $C_H$ nucleic acid constructs

| Primer name | Primer Sequence (SEQ ID NO) |
|---|---|
| P6 | 5'-AAATCTTGTGACAAAACTCACACA TGCCCACCGTGCCCAGCACCACCTG TG-3' (SEQ ID NO: 68) |
| P7 | 5'-GAGAAAACCATCTCCAAAGCCAAA GGGCAGCCCCGAGAACCACAGGTGTAC ACC-3'(SEQ ID NO: 69) |
| P8 | 5'-CTCTTTTGGTAGAGGTTTCGGTTT CCCGTCGGGGCTCTTG GTGTCCACAT GTGG-3' (antisense) (SEQ ID NO: 70) |
| P9 | 5'-CTTCAGGGAGAGGGACAGAGGCCC ATTTACTCGCCGGCG-3' (antisense) (SEQ ID NO: 71) |
| P10 | 5'-GCTGACAGACTAACAGACTG-3' (SEQ ID NO: 72) |
| P11 | 5'-ATACATTATACGAAGTTATACCGG TA-3' (SEQ ID NO: 73) |

Example 4. CD20×CD3 Bispecific Antibodies Selectively Bind Jurkat, Raji and Monkey T-Cells Compared to Monospecific Antibodies CD3×CD20 antibody-wtFc (Control Antibody 4) was compared to monospecific Control antibodies, as set forth in Example 2, via a FACS binding method for their ability to bind to Jurkat (CD3+, CD20− human T-cell line), Raji (CD3−, CD20+ Human B-cell line), or cynomolgus PBMCs ("mkT cells").

FACS data was acquired using the following protocol: Cells at $2 \times 10^5$ per well were incubated with serially diluted antibodies for 30 min on ice. Post incubation, cells were washed and appropriate secondary (Jurkat, RAJI cells) or cocktail of secondary antibodies (for cyno PBMC) was added and incubated for an additional 30 minutes. After incubation, cells were washed, re-suspended in cold PBS containing 1% BSA and analyzed by flow cytometry on a BD FACS Canto II. Jurkat and Raji cells were gated by side and forward scatters, while cynomolgus T cells were also gated as a CD2+CD4+ population. The $EC_{50}$s for cell binding titration were determined using Prism software with values calculated using a 4-parameter non-linear regression analysis. Results are shown in Table 10.

TABLE 10

EC50 Binding Values (Molar) for Monospecific vs. CD3 × CD20 Bispecific Antibodies

| Antibody | FACS - Jurkat | FACS - RAJI | FACS - mkT cells |
|---|---|---|---|
| Control 1 (anti-CD3) | 1.96E−10 | NB | NB |
| Control 2 (anti-CD3) | (+) | NB | 7.03E−11 |
| Control 3 (anti-CD20) | No Binding | (+) | NB |
| Control 4 (Anti-CD3 × CD20, wild-type CH) | 3.85E−08 | 5.99E−08 | 8.74E−06 |

(+) $EC_{50}$ values not determined, but binding observed;
NB no binding;
NT not tested As shown in Table 10, the panel of tested antibodies showed a range of binding affinities on the various cell lines, depending on their specificities. Bispecific Control Antibody 4 showed the ability to bind both human and cynomolgous target lines. Control Antibody 4 comprises the same anti-CD3×CD20 variable regions with Antibody 1 and Antibody 2 of the invention, however has a wild-type IgG1 CH region. Anti-CD3 Control 1 (OKT3), anti-CD3 Control 2 (SP34), and anti-CD20 Control 3 bound to Jurkat, cynomolgus T cells, and RAJI, respectively.

Example 5. CD20×CD3 Bispecific Antibodies with Wild-Type CH Induce Cytotoxicity to Raji Cells in the Presence of Activated T-Cells The ability of CD20×CD3 bispecific antibodies to redirect T-cell mediated killing to CD20-expressing Raji cells was tested in an in vitro cytotoxicity assay. In addition, the ability of both bispecific and parental anti-CD3 antibodies to kill U937 cells via Fc/FcR interactions was also studied.

Calcein killing assays were carried out using the following protocol: Human and cynomolgus PBMC were isolated over ficoll-Plaque or via Lympholyte Mammal cell separation media, respectively. The isolated PBMCs were activated over a course of several days with media containing recombinant human IL-2 (30 U/ml) and T-cell activation beads (anti-CD3/CD28 for human PBMC, anti-CD2/CD3/CD28 for cynomolgus PBMC).

Target cells (Raji for CD20 mediated killing and U937 for FcR mediated killing) were labeled with calcein, and incubated with activated T-cells at a 10:1 effector: target ratio using 3-fold serial dilutions of antibodies over a course of 3 hours at 37° C. Following incubation, the plates were centrifuged and supernatants were transferred to a translucent black clear bottom plate for fluorescence analysis. $EC_{50}$s defined as the molar concentration of bispecific antibody that induces 50% cytotoxicity was determined using Prism. Values were calculated using a 4-parameter non-linear regression analysis. Results are summarized in Table 10.

TABLE 11

$EC_{50}$ values for CD20 × CD3-Induced Cytotoxicity to Raji and U937 cells

| Antibody | Raji Cytotoxicity Human T-cells [M] | Raji Cytotoxicity Monkey T-cells [M] | U937 Cytotoxicity Human T-cells [M] |
|---|---|---|---|
| Control Ab 1 (anti-CD3) | NA | NA | 3.04E−12 |
| Control Ab 4 (Anti-CD3 × CD20) | 5.63E−11* | 1.27E−12* | 8.86E−11* |

*Data are median values of 3 or more independent assays. Data without a (*) are representative/average values of 1 or 2 independent assays.
NA = No Activity As shown in Table 11, bispecific CD20×CD3 antibody containing human-specific and cynomolgus cross reactive anti-CD3 arms, and a wild-type IgG1 CH region, was able to specifically redirect cytotoxicity to Raji cells in the presence of human activated T cells. In the presence of cynomolgus activated T cells, Raji were killed when they were incubated with Control Ab 4 bispecific antibody that has an anti-CD3 arm that activate monkey T-cells. Both the bispecific antibody as well as Control Ab 1 (anti-CD3 mAb) showed activity in the U937 Fc/FcR dependent killing assay.

This activity could be blocked by the addition of blocking non-specific human IgG to the reaction (Data not shown).

Example 6. CD20×CD3 Bispecific Antibodies comprising Chimeric CH Regions show Decreased Effector Function in a CDC Assay CD20×CD3 Bispecific antibodies with chimeric CH regions (Antibody 1 and Antibody 2), as described above in Example 2, were engineered to alter or reduce effector function. Compared to antibodies comprising a wild-type (wt) heavy chain constant region of the IgG1 isotype (Control Ab 4), amino acid substitutions in the CH region may hinder the ability of an Ig Fc to bind to its receptor(s). Hence, signaling and immune responses, such as B cell activation or phagocytosis, may be altered. The effect of amino acid modifications in the CH region on complement dependent cytotoxicity (CDC) (in this example) and antibody-dependent cell-mediated cytotoxicity (ADCC) effector function (see Example 7) was examined.

To examine the effect of Antibody 1 and Antibody 2 on CDC effector function, CD20-expressing Raji (target) cells (5000/well) or Daudi cells were plated in the presence of 5% human serum complement. Serial dilutions of Antibody 1, Antibody 2 and control antibodies, starting at 100 nM, were added to cells for 4 h at 37° C. Target cell lysis was determined using the CytoTox Glo™ kit (Promega) and percent cytotoxicity was calculated.

Figure 5B:
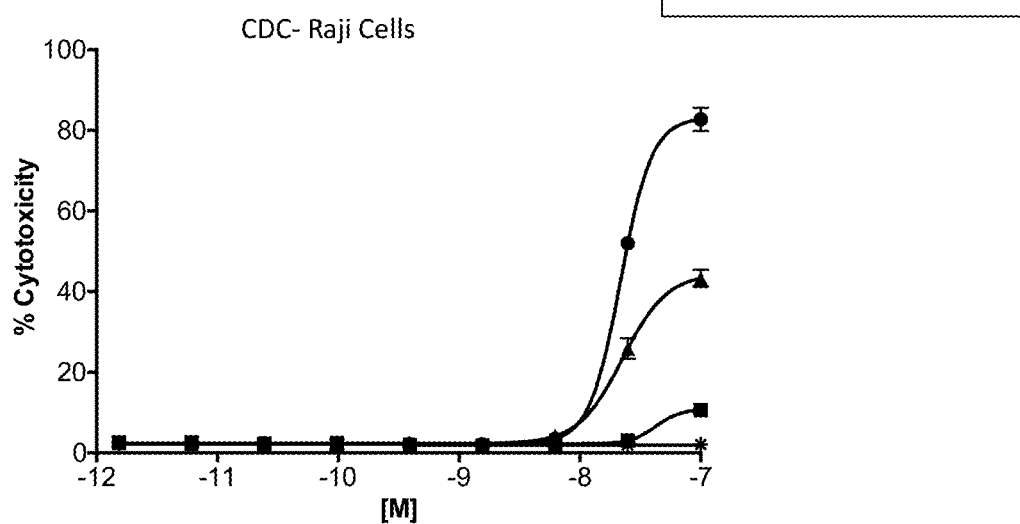

Percent cytotoxicity was calculated using the equation: % cytotoxicity=$((L_S-L_{SR})/(L_{MR}-L_{SR}))*100\%$ where $L_{SR}$ is baseline target cell luminescence and $L_{MR}$ is maximal calcein release from cells lysed by digitonin. The $EC_{50}$ for cytotoxicity was determined using Prism software (Graph Pad). Values were calculated using 4-parameter non-linear regression analysis and are shown in Table 12, and FIGS. 5A and 5B.

The CDC activity of Antibody 1 and Antibody 2 against Daudi and Raji cells is significantly diminished as compared to corresponding antibody having a wt heavy chain constant region. See Table 12, and FIGS. 5A/B. Some CDC activity was observed with Antibody 1 against Raji cells, however, overall results show that the chimeric antibodies mount weaker effector responses than wt IgG1 Fc control antibodies.

TABLE 12

CD20 × CD3 bispecific antibodies comprising chimeric CH regions display reduced activity in CDC assays measuring effector function CDC

| | Target Cell | | | |
|---|---|---|---|---|
| | Daudi | | Raji | |
| | $EC_{50}$ [M] | Maximum Cytotoxicity (%) | $EC_{50}$ [M] | Maximum Cytotoxicity (%) |
| Control Ab 4 | 6.12E−08 | ~95 | 1.98E−08 | ~85 |
| Ab 1 | NA | NA | 2.86E−08 | ~45 |
| Ab 2 | NA | NA | 3.49E−08 | ~10 |

NA: No activity

Figure 6A:
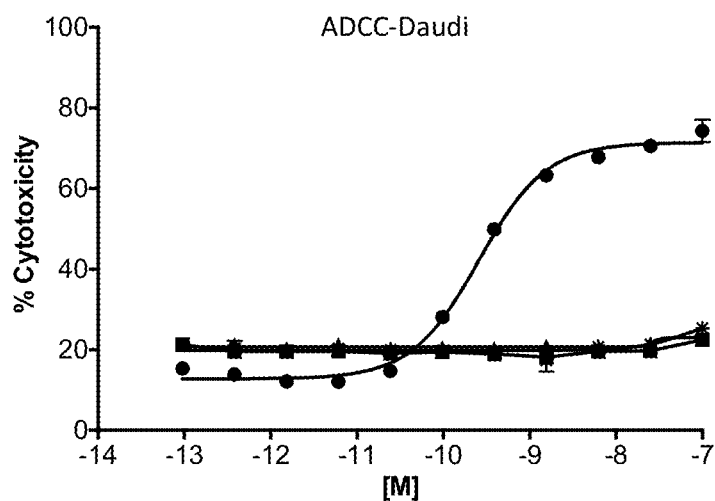
FIGS. 6A and 6B: Dose-response curves depicting lack of ADCC activity with respect to Daudi (FIG. 6A) and Raji (FIG. 6B) cells in the presence of antibodies having wild-type or chimeric hinge $C_H$ regions. ("Control" Antibody 4=Bispecific Ab with wt IgG1 $C_H$; Antibody 1; Antibody 2; IgG1 Isotype Control=nonspecific Ab with wt IgG1 $C_H$.)
Figure 6B:
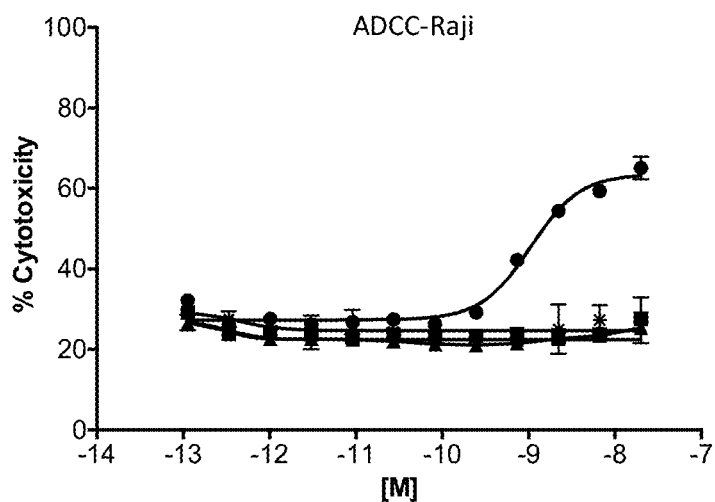

Example 7. CD3×CD20 Bispecific Antibodies Comprising Chimeric CH Regions Show Decreased Effector Function in an ADCC Assay To examine the effect of Antibody 1 and Antibody 2 vs. bispecific antibody with wild-type CH regions (and identical variable regions) on ADCC effector function, freshly isolated unstimulated CD56-positive NK cells or NK92 cells engineered to express the higher affinity V allele of FcγRIIIA were plated with Calcein-labeled CD20-positive Raji or Daudi cells in the presence of chimeric CH-antibodies (Antibody 1 and Antibody 2) and wt-CH control antibody (Control Antibody 4). Calcein release from target cells was monitored and percent cytoxicity was determined. Percent cytotoxicity and $EC_{50}$ were calculated as described for the CDC assay, above. Results are shown in Table 13 and FIGS. 6A and 6B.

The chimeric CH antibodies, Antibody 1 and Antibody 2, do not mediate ADCC activity (Table 13) against Raji or Daudi cells.

TABLE 13

CD3 × CD20 bispecific antibodies comprising chimeric CH regions display reduced activity in ADCC assays measuring effector function ADCC

| | Target Cell | | | |
|---|---|---|---|---|
| | Daudi | | Raji | |
| | EC50 [M] | Maximum Cytotoxicity (%) | EC50 [M] | Maximum Cytotoxicity (%) |
| Control Ab 4 | 1.87E−10 | ~70# | 1.48E−09 | ~65# |
| Ab 1 | NA | NA | NA | NA |
| Ab 2 | NA | NA | NA | NA |

NA: No activity;
background cytotoxicity ~20%

Example 8. Surface Plasmon Resonance Derived Binding Affinities and Kinetic Constants of Chimeric Antibodies The anti-CD3×anti-CD20 bispecific antibodies having chimeric constant heavy chain regions Antibody 1 and Antibody 2 were analyzed using Surface Plasmon Resonance (SPR) (Biacore) technology to determine their kinetic binding parameters to human and cynomolgus Fcγ receptors. Isotype controls, namely wt-IgG1 Isotype Control and wt-IgG4 CPPC Isotype Control, were tested in a similar manner.

Briefly, SPR experiments were performed at 25° C. on a Biacore T200 instrument employing a carboxymethyl dextran-coated (CM-5) chip. A mouse monoclonal anti-pentahistidine antibody (GE Healthcare) was immobilized on the surface of the CM-5 sensor chip using standard amine-coupling chemistry. 140RU-376RU of His-tagged human or monkey FcγR proteins were captured on the anti-pentahistidine amine-coupled CM-5 chip and stock solutions of antibodies were injected at 20 μl/min for 2.5 min over the captured proteins. mAb binding response was monitored and, for low affinity receptors, steady-state binding equilibrium was calculated. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D(M)=k_d/k_a$; and $t_{1/2}$ (min)=$(\ln 2/(60*k_d))$.

TABLE 14

Kinetic binding parameters for wild-type
(wt) and chimeric heavy chain antibodies
Binding to His-captured human FcγRI at 25° C.

| Antibody | $k_a$ (M$^{-1}$sec$^{-1}$) | $k_d$ ($^1$sec$^{-1}$) | $K_D$ (10$^{-9}$ M) | T$^{1/2}$ (min) |
|---|---|---|---|---|
| wt-IgG1 Isotype Control | 1.74E+05 | 7.48E−04 | 4.3 | 15 |
| wt-IgG4 CPPC Isotype Control | 1.71E+05 | 2.36E−03 | 13.9 | 5 |
| Ab 1 | NB | NB | NB | NB |
| Ab 2 | NB | NB | NB | NB |

NB: No binding detected

As the results in Table 14 demonstrate, Antibody 1 and Antibody 2 bispecific antibodies display no binding to human FcγRI, compared to antibodies having the wild-type (wt) hIgG1 or hIgG4-CPPC CH region, in the SPR assay. Chimeric heavy chain bispecific antibodies of this invention also display weak to no binding for several of the low-affinity human FcRγ receptors (e.g. weak binding at human FcRγIIA, FcRγIIB, and no binding detected at human FcRγI, FcRγIIIA, or FcRγIIIB) compared to antibodies with wt hIgG1 or hIgG4-CPPC Fc sequence (Table 15, below).

TABLE 15

Steady-state equilibrium binding for wild-type (wt) and chimeric heavy chain antibodies
Binding to His-captured low-affinity human and cynomolgus FcγR receptors at 25° C.

| | Kd (10$^{-6}$M) Values for Low Affinity FcγR Binding to Chimeric Heavy Chain Antibodies | | | | | | | | |
|---|---|---|---|---|---|---|---|---|---|
| Antibody Tested | human hFcγRIIA (H131) | human FcγRIIA (R131) | cyno FcγRIIA | human FcγRIIB | cyno FcγRIIB | human FcγRIIIA (V176) | human FcγRIIIA (F176) | cyno FcγRIIIA | human FcγRIIIB |
| wtIgG1 Isotype Control | 1.1 | 2 | 4.2 | 2 | 4.2 | 1.5 | 1.3 | 0.6 | 2.3 |
| wtIgG4 (CPPC) Isotype Control | 12 | 10 | 19.3 | 9.8 | 9.6 | 10 | 26 | 5.8 | NB |
| Ab 1 | 12 | 19.3 | 23.1 | 123 | 13.9 | NB | NB | 66.3 | NB |
| Ab 2 | 11.7 | 20.5 | 23.5 | 233 | 14.6 | NB | NB | 42.4 | NB |

NB: No binding detected

Example 9. Pharmacokinetic Profile of Chimeric Antibodies

The toxicokinetic profile of Antibody 1 and Antibody 2 was evaluated by obtaining blood samples from male cynomolgus monkeys (3 animals/treatment group) receiving a single 30-minute IV infusion, followed by a 12-week observation period. Blood samples for toxicokinetic analysis of total drug concentrations in serum were collected pre-dose and post-dose at 5 minutes, and 5, 24, 48, 72 and 168 hours, and Day 14, 21, 35, 49, 66 and 84. The resultant serum samples were analyzed by a direct enzyme linked immunosorbent assay (ELISA) to determine the total drug concentration of Ab 1 or Ab 2. The toxicokinetics of the test articles were assessed using non-compartmental analysis (Phoenix WinNonLin) to determine pharmacokinetic parameters. Results are shown in Table 16 (AUC=area under the concentration vs. time curve; $C_{max}$=observed maximum concentration in serum).

TABLE 16

Pharmacokinetic Profile of Chimeric Antibodies
in Serum of Cynomolgus monkeys Following a Single
Intravenous Infusion to Cynomolgus Monkeys

| | | 1 mg/kg Ab 2 | | 1 mg/kg Ab 1 | |
|---|---|---|---|---|---|
| Parameter | Units | Mean | SD | Mean | SD |
| $C_{max}$ | μg/mL | 33.4 | 3.79 | 26.0 | 4.72 |
| $C_{max}$/Dose | kg*μg/mL/mg | 33.4 | 3.79 | 26.0 | 4.72 |
| $t_{max}$ | day | 0.0243 | 0 | 0.0243 | 0 |
| AUC$_{0\text{-}168\ h}$ | day · μg/mL | 100 | 20.1 | 61.1 | 8.04 |
| AUC$_{0\text{-}168\ h}$/Dose | day*kg*ug/mL/mg | 100 | 20.1 | 61.1 | 8.04 |
| T$^{1/2}$ | Day | 8.14 | 1.15 | 14.0 | 2.64 |

Following a single intravenous dose of 1.0 mg/kg of Ab 1 and Ab 2 in cynomolgus monkeys, mean peak concentrations ($C_{max}$) of 33.4 and 26.0 μg/mL, respectively, and mean AUC$_{0\text{-}168h}$ values of 100 and 61.1 day*ug/mL, respectively, were observed. The apparent terminal half-life was estimated to be between 8.14-14.0 days of these two molecules. The data indicate that continuous exposure to Ab 1 and Ab 2 was maintained in all animals for the majority of the 12-week observation period and exposure was comparable across treatment groups. No apparent immunogenicity with the test articles was observed. The overall pharmacokinetic profiles of Ab 1 and Ab 2 are typical of monoclonal antibodies dosed in cynomolgus monkey.

Example 10. CD3×CD20 Bispecific Antibodies can Deplete CD20+ B-Cells in Cynomolgus Monkeys with Lower Doses than Monospecific Antibody To determine the in vivo potency of Antibody 1 and Control Antibody 4 CD3×CD20 bispecific antibody administration, changes in CD20+ B-cell levels in peripheral blood of cynomolgus monkeys were examined via FACS after administration of anti-CD3×CD20 bispecific antibody compared to monospecific anti-CD20 antibody (Control Ab 3). The study was performed in male cynomolgus monkeys (*Macaca fascicularis*) organized into eight dosing groups of 3 animals per dosing group as flows: Group 1 was the placebo group (vehicle control administration); Group 2 received monospecific antibody (Control Ab 3; rituxan) at 30 mg/kg (30 mg/kg in monkey is equivalent to the human dose of 375 mg/m$^2$ which is considered to be a maximal clinical dose); Group 3 is bispecific CD3×CD20 Control Antibody 4 at 0.01 mg/kg; Group 4—Antibody 4 at 0.1 mg/kg; Group 5—Antibody 4 at 1 mg/kg; Group 6—Antibody 1 at 0.01 mg/kg; Group 7—Antibody 1 at 0.1 mg/kg; and Group 8—Antibody 1 at 1 mg/kg. Blood was drawn at day −7 and day −4 prior to dosing animals. Doses of antibody drug or vehicle (placebo) were administered by i.v. infusion and blood was drawn at 2, 4, and 7 days post dosing. Blood samples were analyzed by FACS for B cell (CD20; Table 17) and T cell (CD3, see below) markers and the absolute number of these cell types was determined.

Briefly, 100 μl of blood was incubated with 1.5 ml RBC lysis buffer in Eppendorf tubes for three minutes. Cells were centrifuged for five minutes at 0.4×g, washed 2× with FACS wash (PBS+3% FBS), and blocked for 10 minutes at room temperature with Fc blocking reagent. Cells were then incubated for 30 minutes at 4° C. with directly conjugated antibodies to hCD45 and CD20 fluorescent reagents. Quantitative determination of B cell subsets (CD20) or T cell subsets (CD3) was first conducted using a heterogeneous gating strategy consisting of CD45 fluorescent staining and side scatter characteristic (SSC) demarcation (CD45brightSSCdim) to delineate white blood cell (WBC) populations. Then B cell populations were identified through the use of relevant fluorescently labeled antibodies (CD20 APC-Cy7). After staining, cells were washed two times before FACS acquisition by a FACSCanto cytometer and analysis with FlowJo software. Results are shown in Table 17 and FIGS. 11A and 11B.

TABLE 17

Number of circulating CD45, CD20 positive cells in monkey peripheral blood following treatment

| Treatment | Animal ID No. | CD20+ cells (E3/μL) at Study Day | | | | |
|---|---|---|---|---|---|---|
| | | −7 | −4 | 2 | 4 | 7 |
| Placebo | 78 | 1.87 | 2.69 | 1.85 | 2.09 | 1.62 |
| | 79 | 1.28 | 1.31 | 0.98 | 1.24 | 0.98 |
| | 80 | 2.41 | 2.90 | 2.23 | 2.71 | 1.78 |
| Control Ab 3 | 81 | 0.71 | 0.80 | 0.00 | 0.00 | 0.00 |
| | 82 | 0.97 | 2.49 | 0.00 | 0.00 | 0.00 |
| | 83 | 0.71 | 1.28 | 0.00 | 0.00 | 0.00 |
| CD3 × CD20-wtFc (Ab 4) 0.01 mg/kg | 84 | 2.00 | 2.82 | 0.03 | 0.02 | 0.03 |
| | 85 | 1.23 | 1.96 | 0.00 | 0.00 | 0.00 |
| | 88 | 1.50 | 2.29 | 0.01 | 0.00 | 0.00 |
| CD3 × CD20-wtFc (Ab 4) 0.1 mg/kg | 87 | 0.79 | 1.20 | 0.00 | 0.00 | 0.00 |
| | 88 | 1.72 | 3.05 | 0.00 | 0.00 | 0.00 |
| | 89 | 0.28 | 0.60 | 0.00 | 0.00 | 0.00 |
| CD3 × CD20-wtFc (Ab 4) 1 mg/kg | 90 | 0.63 | 1.02 | 0.00 | 0.00 | 0.00 |
| | 91 | 0.66 | 0.65 | 0.00 | 0.00 | 0.00 |
| | 92 | 0.56 | 1.50 | 0.00 | 0.00 | 0.00 |
| Ab 1 0.01 mg/kg | 93 | 1.16 | 1.96 | 0.00 | 0.00 | 0.00 |
| | 94 | 0.72 | 1.49 | 0.00 | 0.04 | 0.00 |
| | 95 | 1.95 | 1.94 | 0.02 | 0.02 | 0.01 |
| Ab 1 0.1 mg/kg | 96 | 0.48 | 0.60 | 0.00 | 0.00 | 0.00 |
| | 97 | 1.30 | 1.82 | 0.00 | 0.00 | 0.00 |
| | 98 | 4.87 | 5.00 | 0.00 | 0.00 | 0.00 |
| Ab 1 1 mg/kg | 99 | 0.23 | 0.34 | 0.00 | 0.00 | 0.00 |
| | 00 | 1.39 | 1.93 | 0.00 | 0.00 | 0.00 |
| | 01 | 2.29 | 2.30 | 0.00 | 0.00 | 0.00 |

As shown in Table 17 and FIG. 11A, administration of the CD3×CD20 bispecific antibodies and the anti-CD20 monospecific antibody resulted in depletion of circulating B-cells to baseline levels by the first time point measured (day 2). This depletion was not seen in the placebo control animal cohort. B-cell depletion in the bispecific cohorts was maintained for 1 week after 1 mg/kg dosing of bispecific antibodies, and B-cell depletion was maintained in the 0.01 and 0.10 mg/kg dose bispecific cohorts as well.

T-cell (CD3+) levels were also monitored in this experiment by fluorescently labeled anti-CD3 antibodies. A transient loss of circulating T-cells was observed at day 2 post-dose in the bispecific antibody cohorts (Ab 4 and Ab 1; all doses). No loss of T-cells (below baseline) was observed in the Vehicle (Placebo) Control or Control Ab 3 (Rituxan) groups at the time points measured. T-cell levels returned to baseline levels in the bispecific antibody cohorts by the day 4 time-point and maintained at baseline levels until the end of the experiment (See FIG. 11B).

Figure 12A:
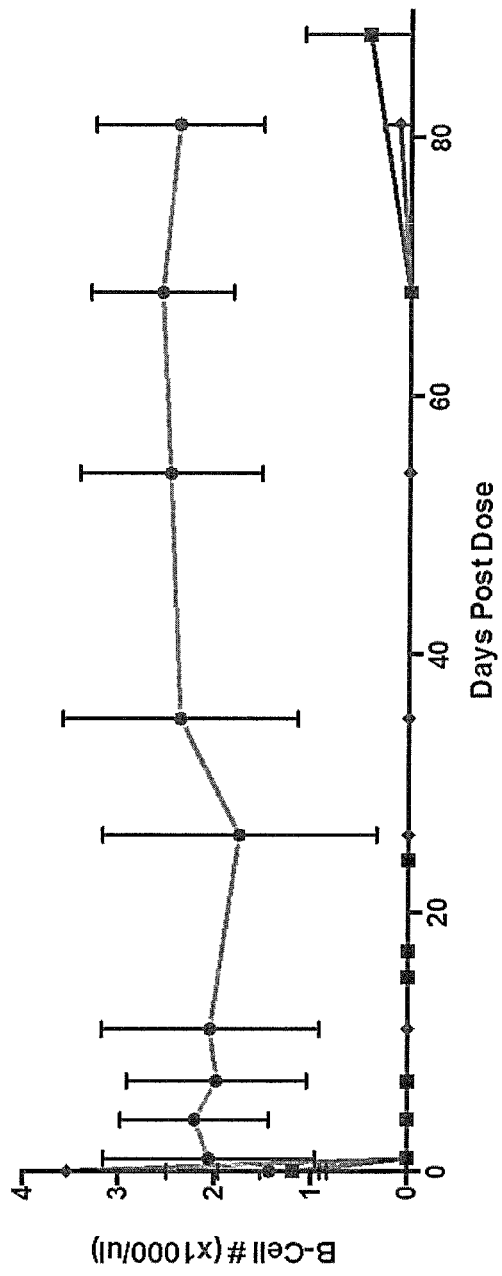
FIGS. 12A and 12B depict the in vivo potency of Antibody 1 and Antibody 4 CD3×CD20 bispecific antibody administration by measuring changes in CD20+ B-cell levels or CD3+ T-cell levels in peripheral blood of cynomolgus monkeys in a long term (3 month) study. Placebo (vehicle) or bispecific antibodies were administered at 1.0 mg/kg at Day 0.
Figure 12B:
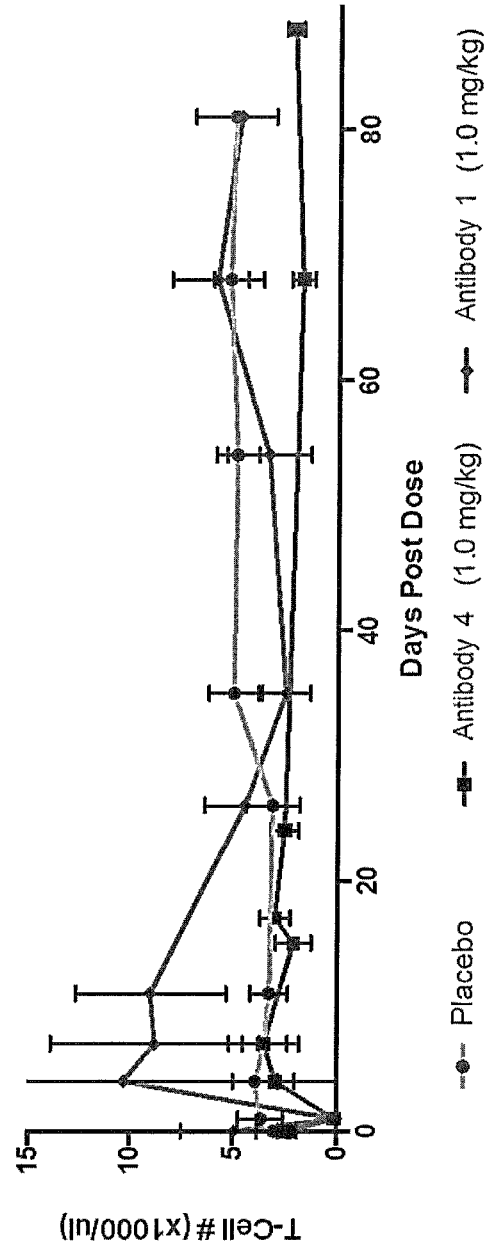

In vivo potency of Antibody 1 and Antibody 4 CD3× CD20 bispecific antibodies was measured in peripheral blood of cynomolgus monkeys in a long term (3 month) study measuring changes in CD20+ B-cell levels or CD3+ T-cell levels, analogously to the study described above. Placebo (vehicle) or bispecific antibodies were administered at 1.0 mg/kg at Day 0. B-cell levels in the peripheral blood were significantly depleted by day 2 in both bispecific antibody cohorts and levels remained depleted over the length of the study in all samples except placebo (see FIG. 12A). A transient loss of T-cells was observed by day 2 in the bispecific cohorts, then T-cells recovered to baseline levels by day 4, and remained around baseline as measured throughout the study (>80 days) for the animals treated with bispecific antibodies (FIG. 12B). No transient loss of T-cells was observed in animals treated with placebo.

To further measure the in vivo potency of Antibody 1 and Antibody 4 CD3×CD20 bispecific antibody at low doses of administration, changes in CD20+ B-cell levels or CD3+ T-cell levels were measured in peripheral blood of cynomolgus monkeys in a long term (2 month) study, analogously to the above experiments. Bispecific antibodies were administered at either 0.01 mg/kg or 0.001 mg/kg (1 μg/kg) at Day 0. B-cell levels in the peripheral blood were significantly depleted by day 2 and levels remained depleted over the length of the study for both CD3×CD20 cohorts (FIG. 13A), similar to that observed for animals treated with higher doses of CD3×CD20 bispecific antibodies (as seen in Table 17 and FIG. 11A or 12A). Animals treated with very low doses (1 μg/kg) of bispecific antibodies experience the same transient loss of T-cells and recovery as seen in animals treated with higher doses of CD3×CD20 bispecific antibodies (see FIG. 13B compared to FIG. 11B or 12B).

Figure 14:
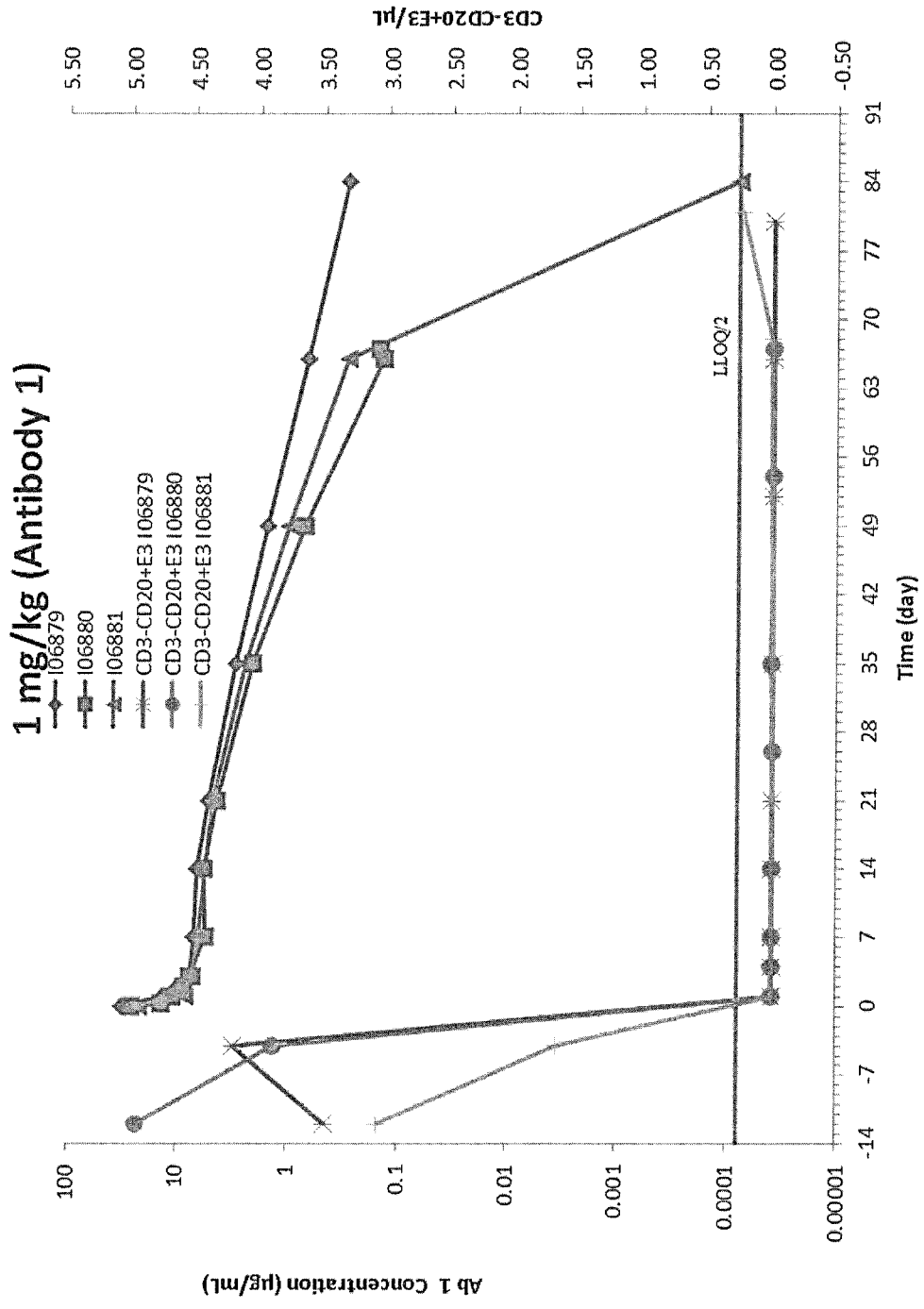
FIG. 14 shows the correlation of B-cell loss with loss of antibody in the peripheral blood of animals treated with CD3×CD20-chimericFc Antibody 1. As antibody exposure (open symbols) in the circulation of animals is depleted over time, B-cell populations (solid symbols) begin to recover (e.g. as observed at day 81 for animal no. I06881 (solid circle)).

The B-cell loss as observed in the described studies was correlated with loss of circulating antibody in the peripheral blood of animals treated with CD3×CD20-chimericFc Antibody 1 (see FIG. 14). As antibody exposure in the circulation of animals is depleted over time, B-cell populations begin to recover (e.g. as observed at day 81 for animal no. I06881).

Figure 15:
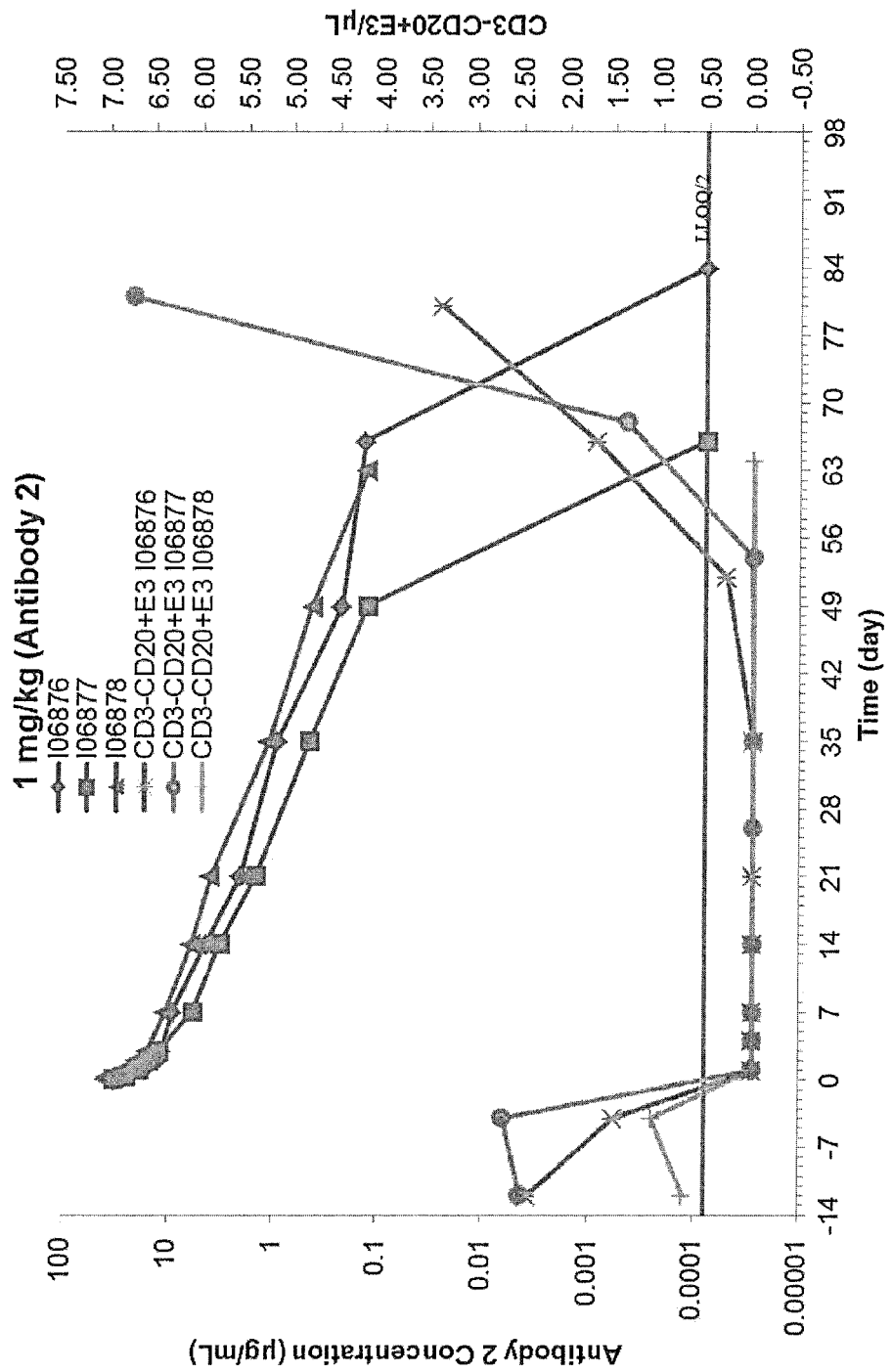
FIG. 15 shows the correlation of B-cell loss with loss of antibody in the peripheral blood of animals treated with CD3×CD20-chimericFc Antibody 2. As antibody exposure (open symbols) in the circulation of animals is depleted over time, B-cell populations (solid symbols) begin to recover (e.g. as observed at day 66 for animal no. I06876 (solid triangle), and at day 68 for animal no. I06877 (solid square)).
Figure 16:
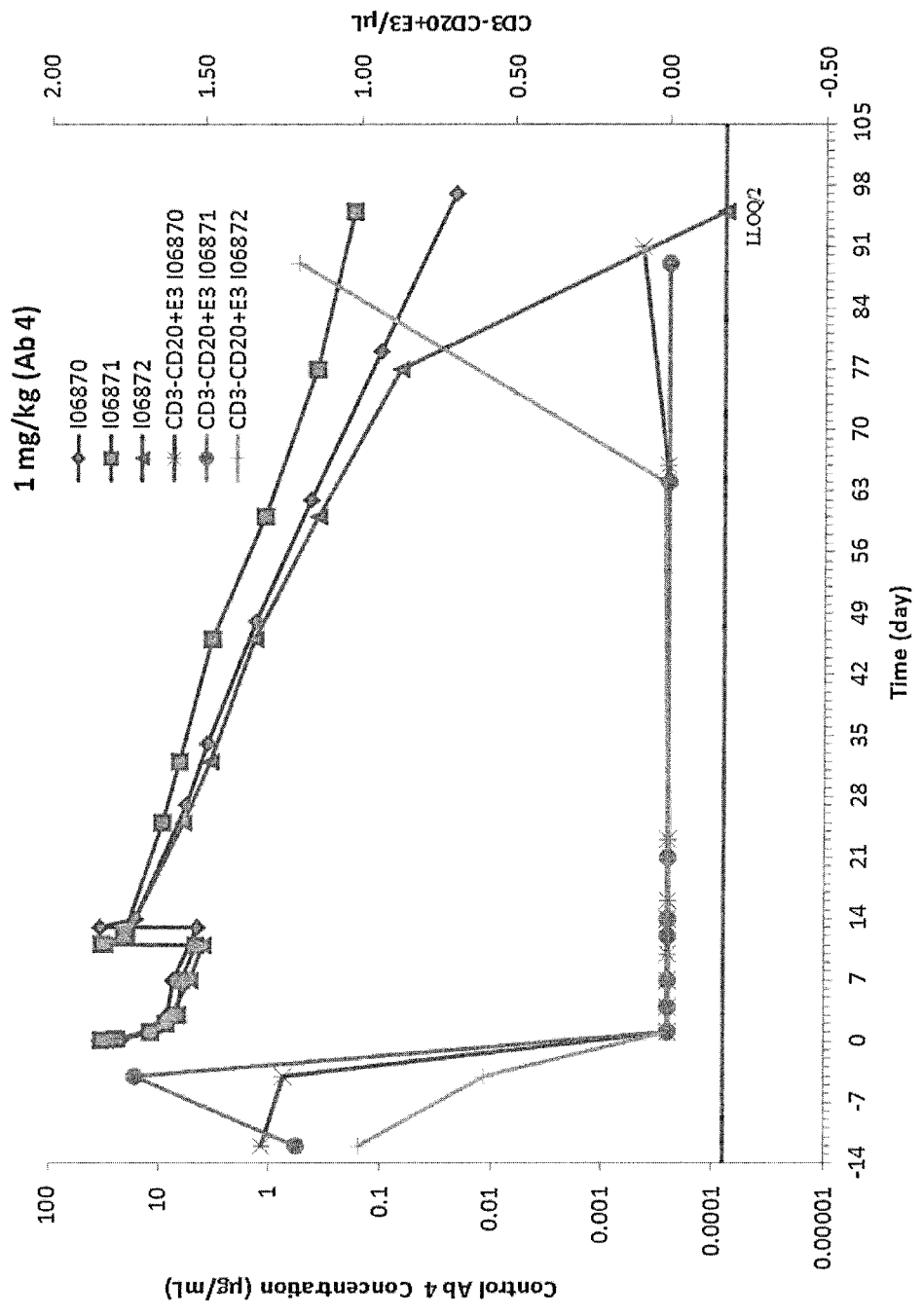
FIG. 16 shows the correlation of B-cell loss with loss of antibody in the peripheral blood of animals treated with CD3×CD20-wtFc (Ab 4) bispecific antibody. As antibody exposure (open symbols) in the circulation of animals is depleted over time, B-cell populations (solid symbols) begin to recover (e.g. as observed at day 91 for animal no. I06870 (solid triangle), and at day 64 for animal no. I06872 (solid circle)).

Correlation of B-cell loss with loss of circulating antibody in the peripheral blood was also seen in animals treated with CD3×CD20-chimericFc Antibody 2 (see FIG. 15), whereas antibody exposure in the circulation of animals is depleted over time, then B-cell populations begin to recover e.g. as observed at day 66 for animal no. I06876, and at day 68 for animal no. I06877. Similar correlation was also seen in animals treated with CD3×CD20-wtFc (Ab 4) bispecific antibody (see FIG. 16). As antibody exposure in the circulation of animals is depleted over time, B-cell populations begin to recover (see FIG. 16, e.g. as observed at day 91 for animal no. I06870, and at day 64 for animal no. I06872).

Example 11. CD3×CD20 Bispecific Antibodies can Deplete CD20+ B-Cells in Lymphoid Tissues of Cynomolgus Monkeys with Lower Doses than Monospecific Antibody Changes in CD20+ B-cell levels in lymphoid tissues of cynomolgus monkeys were examined via FACS after administration of anti-CD3×CD20 bispecific antibody (Antibody 1 or Antibody 4) compared to monospecific anti-CD20 antibody (Control Ab 3—Rituxan). The study was performed in male cynomolgus monkeys (*Macaca fascicularis*) organized into eight dosing groups of 3 animals per dosing group as flows, analogously to Groups 1-8 as outlined in Example 10, above. Doses of antibody drug or vehicle were administered by i.v. infusion and animals were sacrificed and tissues collected at 7 days post dosing. Tissue samples were analyzed by FACS for white blood cell (CD45+), and specifically B cell (CD20+), markers, then the % volume of B cells was determined.

B cell populations were identified through the use of relevant fluorescently labeled antibodies (CD20 APC-Cy7) and FACS acquisition, analogously to the method described above for Example 10. Results are shown in Table 18 and in FIGS. 17A and 17B.

TABLE 18

Percent CD20 positive cells in monkey Mesenteric Lymph Node and Spleen following treatment

| Treatment | Animal ID No. | Mesenteric Lymph Node Day 7 | Spleen Day 7 |
|---|---|---|---|
| Placebo | 78 | 38.14 | 63.22 |
| | 79 | 38.57 | 62.79 |
| | 80 | 37.36 | 49.17 |
| Control Ab 3 30 mg/kg | 81 | 6.21 | 4.5 |
| | 82 | 10.3 | 3.45 |
| | 83 | 4.21 | 2.18 |
| Ab 4 0.01 mg/kg | 84 | 13.43 | 3.14 |
| | 85 | 6.88 | 2.27 |
| | 86 | 10.78 | 1.39 |
| Ab 4 0.1 mg/kg | 87 | 1.51 | 2.37 |
| | 88 | 0.45 | 1.65 |
| | 89 | 1.24 | 2.4 |
| Ab 4 1 mg/kg | 90 | 0.63 | 0.97 |
| | 91 | 0.62 | 1.93 |
| | 92 | 1.08 | 1.22 |
| Ab 1 0.01 mg/kg | 93 | 5.38 | 1.22 |
| | 94 | 6.37 | 1.89 |
| | 95 | 13.25 | 6.99 |
| Ab 1 0.1 mg/kg | 96 | 0.43 | 1.55 |
| | 97 | 0.68 | 1.75 |
| | 98 | 2.36 | 2.97 |
| Ab 1 1 mg/kg | 99 | 0.33 | 1.79 |
| | 00 | 1.6 | 1.71 |
| | 01 | 0.5 | 1.21 |

Figure 17A:
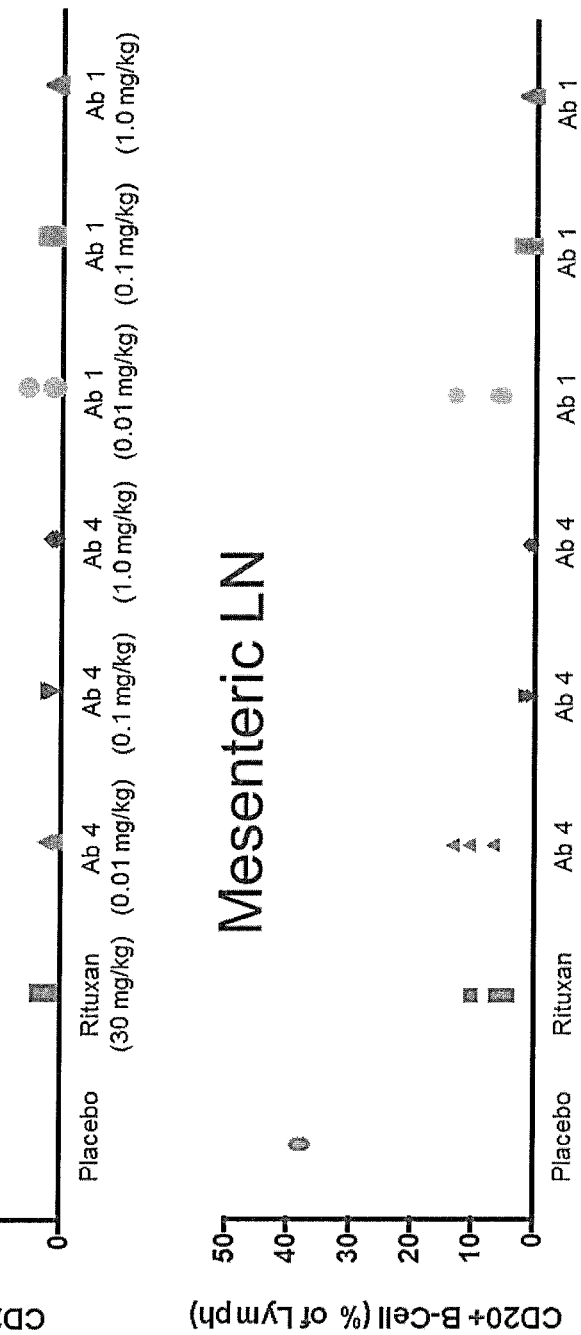
FIGS. 17A and 17B depict the depletion of tissue B-cells in spleen (FIG. 17A) or mesenteric lymph nodes (FIG. 17B) of cynomolgus monkeys resulting from administration of the CD3×CD20 bispecific antibodies compared to the anti-CD20 monospecific antibody, with much lower doses (0.01 to 1.0 mg/kg doses) administered to the bispecific cohorts. This depletion was not seen in the placebo control animal cohort in either tissue. Both CD3×CD20 bispecific antibodies (Ab1 and Ab 4) caused a dose-dependent B-cell depletion in the lymphoid organs, and at doses equivalent to or greater than 0.1 mg/kg, the bispecific antibodies deplete B-cells more effectively than rituximab.

As shown in Table 18 and FIG. 17A, administration of the CD3×CD20 bispecific antibodies compared to the anti-CD20 monospecific antibody resulted in depletion of tissue B-cells in spleen at much lower doses (0.01 to 1.0 mg/kg dose) for the bispecific cohorts. This depletion was not seen in the placebo control animal cohort.

Figure 17B:

As shown in Table 18 and FIG. 17B, administration of the CD3×CD20 bispecific antibodies compared to the anti-CD20 monospecific antibody resulted in depletion of tissue B-cells in mesenteric lymph nodes at much lower doses (0.01 to 1.0 mg/kg dose) for the bispecific cohorts, with the 0.1 mg/kg dose and 1 mg/kg dose of bispecific antibody resulting in more efficient B-cell depletion than in the monospecific cohort. This depletion was not seen in the placebo control animal cohort. Upon immunohistochemical staining for CD20 (data not shown), residual B-cells were detected in lymph nodes of the monospecific-treated (Rituxan® 30 mg/kg) cohort. No residual B-cells were detected in the tissues collected from cohorts treated with doses of 0.1 to 1.0 mg/kg bispecific anti-CD3×CD20 antibody. These data demonstrate that Ab1 and Ab1 have a depth of killing of B cells that is stronger than Ab3.

Example 12. Tumor Treatment with CD3×CD20 Bispecific Antibody

A. Treatment with CD20×CD3 Bispecific Antibody Suppresses Raji Tumor Growth in NSG Mice To assess the efficacy of selected anti-CD3×CD20 bispecific antibodies in reducing Raji tumor growth, NSG mice (NOD/LtSz-scid/IL2Rγ$^{null}$ mice) purchased from Jackson Laboratories (Bar Harbor, Me., USA) were subcutaneously co-implanted with $2\times10^6$ Raji tumor cells and $5\times10^5$ human PBMCs (Day 0). On the same day, mice were treated with an intraperitoneal dose of 0.4, 0.04 or 0.004 mg/kg per mouse (N=5 mice per treatment group) of either Antibody 1, or Control Antibody 5 (an IgG1 antibody to an irrelevant target), or Vehicle Control. Starting on Day 0, the mice were treated twice weekly with an intraperitoneal dose of drug or vehicle for the remainder of the study. Tumor size was measured two times per week using calipers, and tumor volume calculated as Volume=(length×width$^2$)/2. Statistical analyses were performed utilizing GraphPad software Prism 5.0 (Macintosh Version).

Statistical significance was determined by two-way ANOVA with Tukey's multiple comparisons post-test. Data from each of the readouts were compared across treatment groups. A threshold of p<0.05 was considered statistically significant.

Figure 7A:
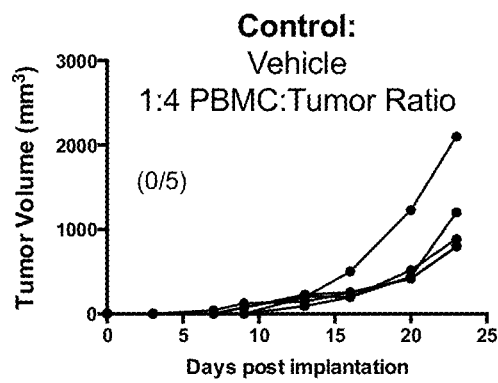
Figure 7B:
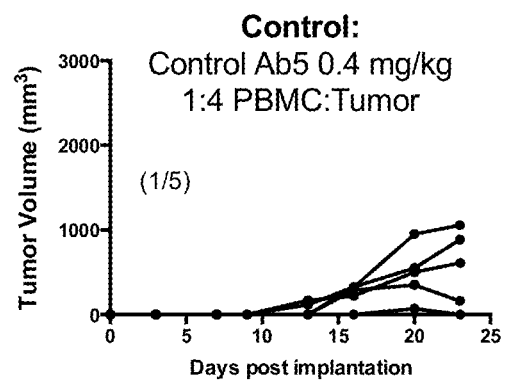
Figure 7C:
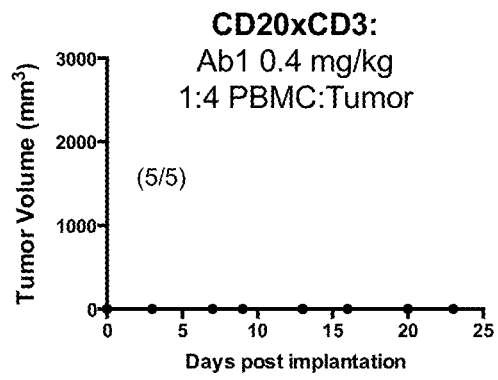

Results are shown in FIGS. 7A-7F. These results show that Antibody 1 (CD3×CD20-chimericFc) targets Raji tumors in mice which have co-implanted human immune cells, resulting in complete tumor growth suppression at the doses tested (FIG. 7C: 0.4 mg/kg Ab1; FIG. 7E: 0.04 mg/kg Ab1; FIG. 7F: 0.004 mg/kg Ab1). This Example demonstrates that treatment with CD3×CD20 bispecific Antibody 1 was effective in inhibiting tumor growth starting at the time of tumor implantation. Raji tumor growth remained completely suppressed up to 23 days post implantation in mice given doses of 0.4, 0.04 or 0.004 mg/kg Antibody 1, relative to control. It was also observed that neither Antibody 1 nor the Control Antibody had a significant effect on mouse body weight during the study (data not shown).

The antitumor effect of CD3×CD20 bispecific antibodies was further tested in a similar NSG mouse model (as described above), however each NSG mouse was dosed with 1 mg mouse IgG (mIgG2a Fc) on Day −1, and one time per week thereafter. Results are shown in FIGS. 8A-8B.

Figure 8A:
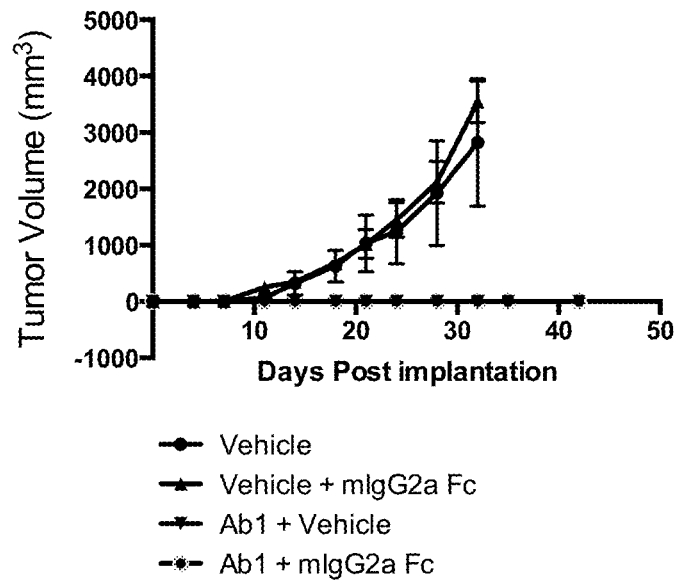
FIGS. 8A and 8B show the tumor volume (in $mm^3$) over time in NSG mice implanted subcutaneously with a mixture of Raji tumor cells and PBMCs, and treated with Ab1 (CD3×CD20-chimericFc) compared to vehicle, with or without IgG supplementation (FIG. 8A), or treated with Ab4 (CD3×CD20-wtFc) compared to vehicle, with or without IgG supplementation (FIG. 8B). Both CD3×CD20 bispecific antibodies demonstrate significant tumor growth inhibition with IgG supplementation in this model.
Figure 8B:
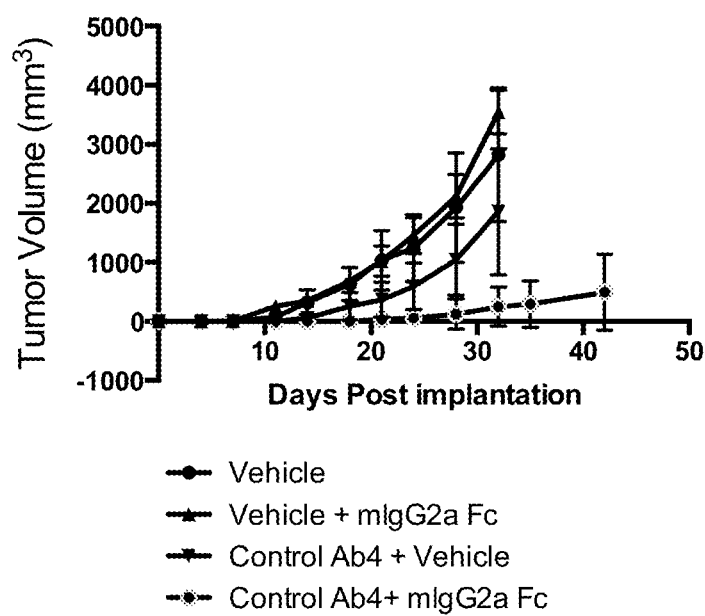

This experiment demonstrates that treatment with either CD3×CD20 bispecific Antibody 1 (CD3×CD20-chimericFc) or CD3×CD20 bispecific Antibody 4 (CD3×CD20-wtFc) was effective in inhibiting tumor growth starting at the time of tumor implantation at the doses of bispecific Ab tested in the presence of circulating IgG (FIGS. 8A-8B). As seen in FIG. 8A, Antibody 1 (CD3×CD20-chimericFc bispecific antibody) demonstrates complete tumor growth inhibition over the time period tested with or without IgG supplementation in this experiment.

B. Treatment with CD3×CD20 Bispecific Antibody Shrinks Established Tumors in NSG Mice The efficacy of selected anti-CD3×CD20 bispecific antibodies in reducing established tumors in NSG mice was assessed. NSG mice (NOD/LtSz-scid/IL2Rγ$^{null}$ mice) were purchased from Jackson Laboratories (Bar Harbor, Me., USA) and were subcutaneously co-implanted with HLA-matched Raji tumor cells ($2\times10^6$) and human PBMCs ($5\times10^5$)(Day −15). Tumors were allowed to establish in the host for 15 days prior to treatment. At one day prior to drug administration (Day −1), the mice were each dosed with supplements of 5 mg mIgG2a Fc. The mice were subsequently dosed with mIgG2a Fc at 5 mg per mouse one time per week during the length of the experiment (Day 7, Day 14, etc.). Mice were separated into 2 experimental groups prior to drug administration according to tumor size: Group 1: ~200-400 mm$^3$ or Group 2: ~500-900 mm$^3$.

Figure 9:
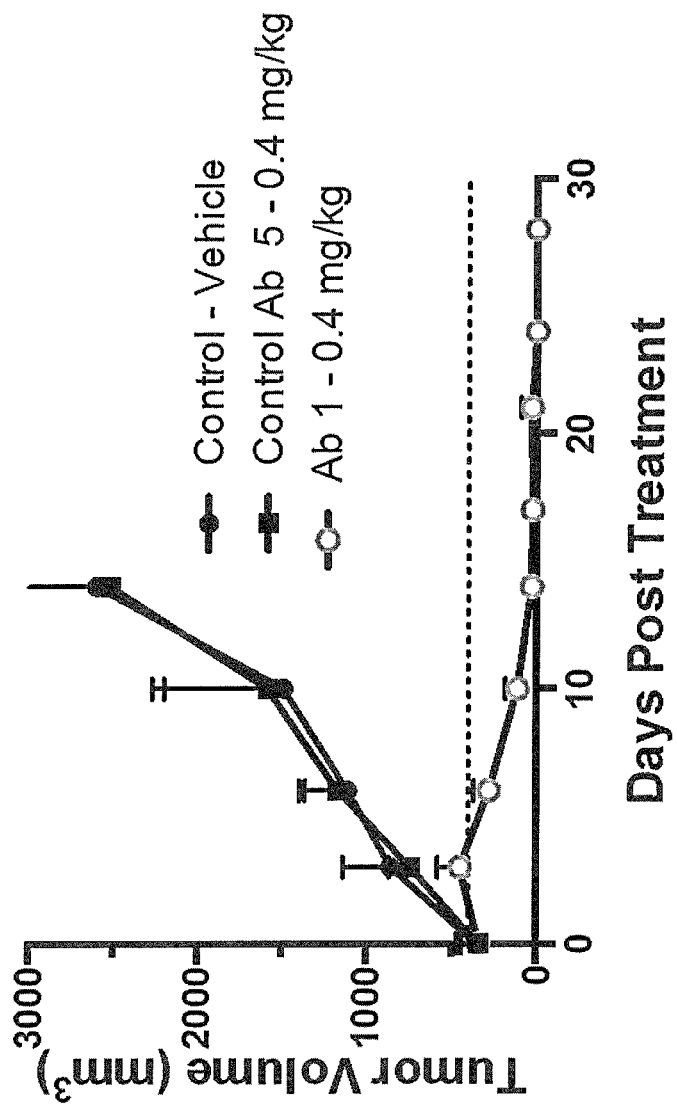
FIG. 9 illustrates regression of established tumors (~200-400 $mm^3$) by the $14^{th}$ day in NSG mice treated with CD3×CD20 bispecific antibody. NSG mice were implanted subcutaneously with a mixture of Raji tumor cells and PBMCs 15 days prior to treatment to allow tumors to become established. Mice were subsequently treated with 0.4 mg/kg Antibody 1 (CD3×CD20-chimeric Fc antibody), or 0.4 mg/kg Control Ab5 (anti-FeID1 Ab), or vehicle control once per week (Day 7, Day 14, Day 21).
Figure 10:
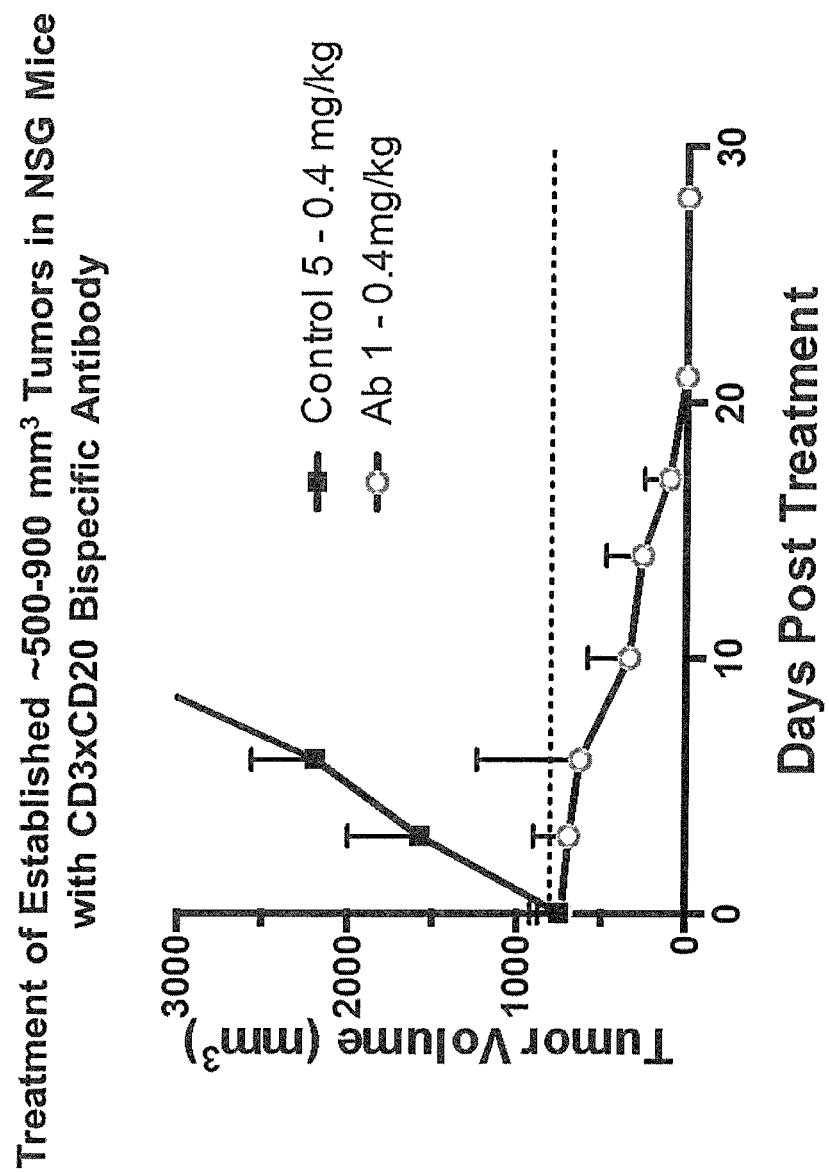
FIG. 10 illustrates regression of established tumors (~500-900 $mm^3$) by the $21^{st}$ day in NSG mice treated with CD3×CD20 bispecific antibody. NSG mice were implanted subcutaneously with a mixture of Raji tumor cells and PBMCs 15 days prior to treatment to allow tumors to become established. Mice were treated with 0.4 mg/kg Antibody 1 (CD3×CD20-chimeric Fc antibody), or 0.4 mg/kg Control Ab5 (anti-FeID1 Ab) once per week (Day 7, Day 14, Day 21).

Following drug treatment, tumor size was monitored and recorded in each mouse at Day 0, 3, 6, 10, 14, 17, 21 and 28. Tumor size was measured two times per week using calipers, and tumor volume calculated as Volume=(length×width2)/2. Presence of tumors was also determined by palpability. Statistical analyses were performed utilizing GraphPad software Prism 5.0 (Macintosh Version). Data from each of the readouts were compared across treatment groups. Results are shown in FIGS. 9 and 10.
- a. Group 1: ~200-400 mm$^3$ tumors. Starting at Day 0, several cohorts of 4 or 5 mice each were treated with the indicated dose of drug or vehicle one time per week (i.e. Day 7, Day 14, etc.) as follows:
  i. Control: vehicle alone
  ii. Control Antibody 5, 0.4 mg/kg
  iii. Antibody 1 (CD20×CD3-chimericFc), 0.4 mg/kg
- b. Group 2: ~500-900 mm$^3$ tumors. Starting at Day 0, several cohorts of 4 mice each were treated with the indicated dose of drug one time per week (i.e. Day 7, Day 14, etc.) as follows:
  i. Control Antibody 5, 0.4 mg/kg
  ii. Antibody 1 (CD20×CD3-chimericFc), 0.4 mg/kg Tumors fully regressed in the cohort administered with 0.4 mg/kg Antibody 1 (CD20×CD3-chimericFc) by 14 days. See FIG. 9.

In the model with larger established tumors (i.e. Group 2, ~500-900 mm$^3$), Antibody 1 (CD20×CD3-chimericFc) treatment (0.4 mg/kg) resulted in complete ablation of observed tumors in mice by 21 days. See FIG. 10, which demonstrates the effectiveness of Ab1 in treating mice with large lymphoma masses (i.e. tumors positive for CD20 expression) greater than 0.5 cm and up to 0.9 cm in volume.

Example 13. CD3×CD20 Bispecific Antibodies Induce PBMC Proliferation In Vitro The ability of selected CD3×CD20 bispecific antibodies and Control constructs to stimulate Peripheral Blood Mononuclear Cells (PBMCs) and induce proliferation was assessed using ATP catalyzed quantification (CellTiter Glo®). The activation of PBMCs results in the release of cytokines which drive cellular proliferation.

Proliferation data was acquired using the following protocol: Human or cynomolgus monkey derived PBMCs (5×10$^5$/well) were incubated with serial dilutions of CD3× CD20 bispecific antibodies or control antibody and commercial anti-CD28 antibody (human: 200 ng/mL, cyno: 500 ng/mL) for 72 hours at 37° C. Cells were quantitated using Cell Titer Glo® and luminescence as readout for cell viability was measured using a VICTOR X5 multi-label plate reader (PerkinElmer) to detect live cells. Cell viability (fold induction of stimulated versus unstimulated cells) was determined by dividing the luminescence of stimulated cells by the baseline luminescence of unstimulated cells and graphed using Prism software. Results are summarized in Table 19 and FIGS. 18A and 18B.

TABLE 19

EC$_{50}$s for human and cynomolgus PBMC proliferation induced by anti-CD3 × CD20 bispecific antibodies

| Antibody | Human PBMC Proliferation EC$_{50}$ [M] | Cyno PBMC Proliferation EC$_{50}$ [M] |
|---|---|---|
| Control Ab 5 | NA | NA |
| CD3 × CD20-wtFc (Ab 4) | 8.427E−12 | 3.325E−11 |
| Antibody 1 | 1.163E−10 | 1.275E−11 |

Data are median values of 3 or more independent assays.
NA = no activity.

Figure 18A:
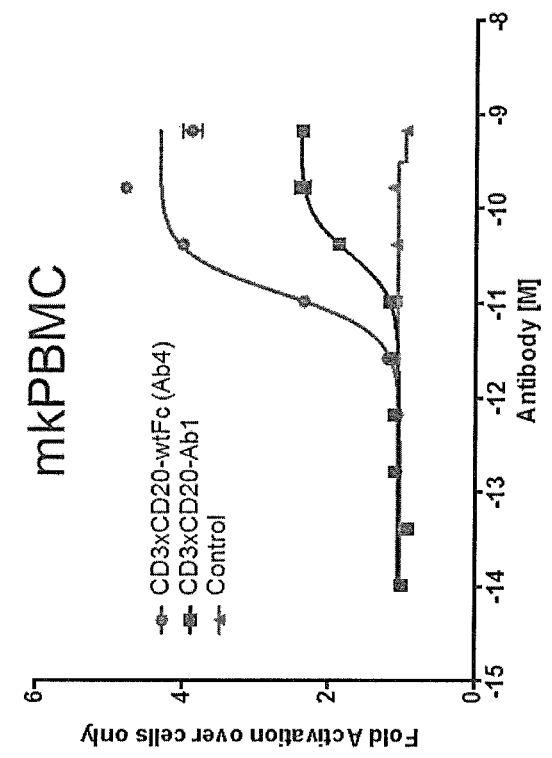
FIGS. 18A and 18B illustrate that CD3×CD20 bispecific antibodies induce proliferation of human PBMCs (FIG. 18A) or cynomolgus PBMCs (FIG. 18B) in an in vitro bioassay, whereas Control Antibody 5 (-▲-; not specific to CD3×CD20) exhibited no activity.
Figure 18B:
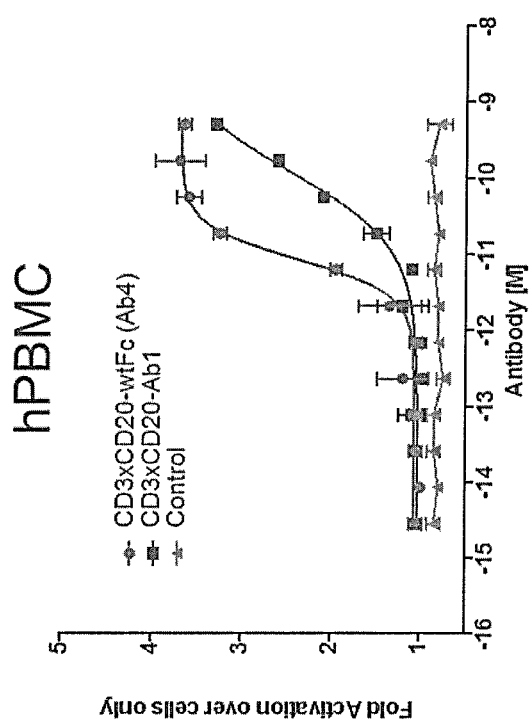

As shown in Table 19 and FIGS. 18A-18B, both CD20× CD3 bispecific antibodies of the invention induced proliferation of human or cynomolgus PBMCs. Antibody 1 induced proliferation of both human and cynomolgus PBMC with approximately equal potency. Control Ab 5 exhibited no activity.

Example 14. CD20×CD3 Bispecifics Mediate Cell Killing by Activated T-Cells In Vitro Human or cynomolgus PBMCs were isolated over Ficoll-Paque or using Lympholyte Mammal cell separation media, respectively. Isolated PBMCs (1×10$^6$ cells/mL human PBMCs or 5×10$^6$ cells/mL cynomolgus PBMCs) were activated for 7 and 21 days, respectively, in complete media (RPMI supplemented with 10% FBS, 100 U/mL penicillin, 100 μg/mL streptomycin, 292 μg/mL L-glutamine) containing recombinant human IL-2 (30 U/mL for human PBMCs, 100 U/mL for cynomolgus PBMCs) and T cell activation beads (anti-CD3/CD28 for human PBMCs, anti-CD2/CD3/CD28 for cynomolgus PBMCs). CD20 expressing Raji cells (2×10$^6$ cells/mL) were labeled with 8 μM Calcein-AM for 30 minutes at 37° C. and washed 3 times with media. Calcein-labeled target cells (10,000-20,000 cells/well) were plated in 200 μL with activated T cells (effector/target cell ratio 10:1) and serial dilutions of Antibody 1, Ab 4 or Control Ab 5 (human concentration range: 2 nM to 0.00003 nM; cynomolgus concentration range: 6.6 nM to 0.002 pM) in complete media for 2 hours at 37° C. Following incubation, the plates were centrifuged and supernatants were transferred to a translucent black clear bottom plate for fluorescence analysis. Percent cytotoxicity was calculated using the equation:

$$\% \text{ cytotoxicity} = ((FS-FSR)/(FMR-FSR)) * 100\%,$$

where FS is calcein release from the test well, FSR is spontaneous calcein release and FMR is maximal calcein release from cells lysed by Triton-X.

The EC$_{50}$ of cell viability (ATP catalyzed quantification) was determined using Prism software. Cell lysis (cytotoxicity) was measured by calcein release as a fraction of maximal release. The percent cell cytotoxicity was calculated as the observed release compared to maximal release and EC$_{50}$ values determined. Results are shown in Table 20 and FIGS. 19A (human T-cells) and 19B (monkey T-cells).

TABLE 20

EC$_{50}$ values for CD3 × CD20-Induced Cytotoxicity to Raji cells

| Antibody | Raji Cytotoxicity Activated Human T-cells [M] | Raji Cytotoxicity Activated Monkey T-cells [M] |
|---|---|---|
| Control Ab 5 | NA | NT |
| CD3 × CD20-wtFc (Ab 4) | 1.571E−11 | 1.730E−12 |
| Antibody 1 | 2.503E−11 | 9.104E−12 |

NA = No Activity;
NT = Not tested.

As shown in Table 20, Antibody 1 mediated target cell killing with representative EC$_{50}$ values of 25.0pM and 9.10pM for human (FIG. 19A) and cynomolgus (FIG. 19B) T cells, respectively. Antibody 4 mediated target cell killing with representative EC$_{50}$ values of 15.7pM and 1.73pM for human (FIG. 19A) and cynomolgus (FIG. 19B) T cells, respectively. No activity of the control was observed.

In order to monitor the specific killing of CD20-bearing target cells by flow cytometry, B16F10.9 parental murine myeloma cells (that do not express CD20) and B16F10.9 cells engineered to stably express human CD20 (B16F10.9/CD20) were labeled with 1 μM of the fluorescent tracking dyes carboxyfluorescein diacetate succinimidyl ester (CFDA-SE) and Violet Cell Tracker, respectively. After labeling, cells were mixed at a 1:1 ratio, and plated overnight at 37° C. Separately, human PBMCs were plated in supplemented RPMI media at 1×10$^6$ cells/mL and incubated overnight at 37° C. in order to enrich for lymphocytes by depleting adherent macrophages, dendritic cells, and some monocytes. The next day, target cells were co-incubated with adherent cell-depleted naïve PBMC (Effector/Target cell 4:1 ratio) and a serial dilution of the test CD3×CD20 bispecific antibodies or the IgG1 Control Antibody 5 (concentration range: 66.7 nM to 0.25pM) for 48 hours at 37° C. Cells were removed from cell culture plates using an enzyme-free cell dissociation buffer, and analyzed by FACS. For FACS analysis, cells were stained with a dead/live far red cell tracker (Invitrogen). For the assessment of specificity of killing, cells were gated on live Violet and CFDA-SE labeled populations. Percent of each population was reported for the calculation of adjusted survival as follows: Adjusted survival=(R1/R2)*100, where R1=[(B16F10.9/CD20)/bystander cells (B16F10.9)]*100 in the absence of antibody, and R2=the same ratio but in the presence of test antibody.

TABLE 21

EC$_{50}$ values for target-specific killing in B16F10.9/CD20 cells

| Antibody | % Survival B16F10.9/CD20 cells [M] |
|---|---|
| Control Ab 5 | NA |
| CD3 × CD20-wtFc (Ab 4) | 1.282E−11 |
| Antibody 1 | 1.952E−11 |

NA = No Activity.

Figure 20A:
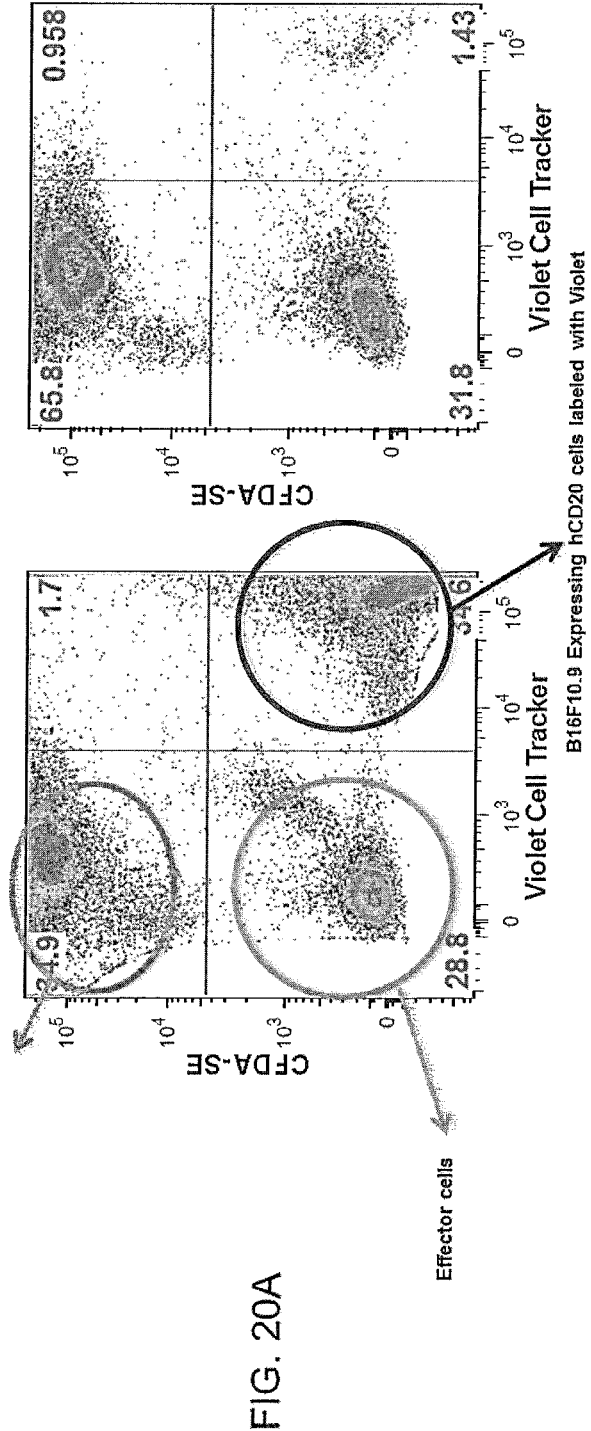
FIGS. 20A and 20B illustrate that CD3×CD20 bispecific antibody mediates cell killing by naïve T-cells.
Figure 20B:
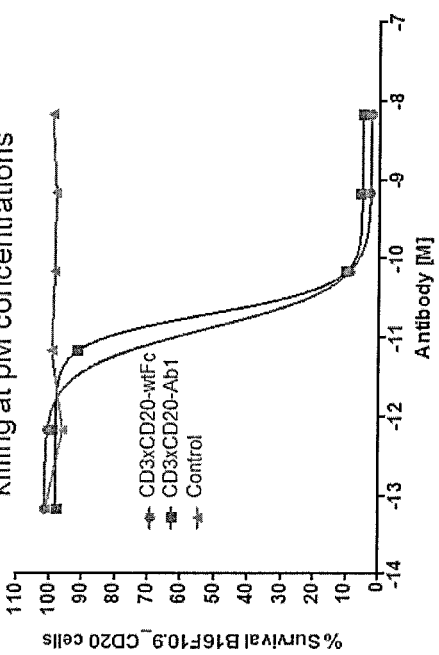

Both CD3×CD20-chimericFc (Antibody 1) and CD3×CD20-wtFc (Antibody 4) specifically directed human T cells to kill only target cells expressing CD20 (FIGS. 20A-B) in a mixed population of cells. Target cell killing was only observed in the presence of the bispecific antibody, with B16F10.9/CD20 cells depleted in a dose-dependent manner by Antibody 1 (EC$_{50}$ 19.5pM) and Antibody 4 (EC$_{50}$ 12.8pM) (FIG. 20B). Less than 5% of CD20-expressing cells were alive at the highest dose tested (10 μg/mL) (FIG. 20B). No evidence of cell death was observed in the parental B16F10.9 cell population or in the B16F10.9/CD20 population with Control Ab 5, an IgG1 control antibody.

Example 15. CD3×CD20 Bispecific Antibody Upregulates the Early Activation Marker CD69 on T Cells in a 20 Hour FACS In Vitro Assay CD69+ is one of the earliest inducible cell surface markers indicating that T cells have been activated. T-cell activation can be determined by examining the up-regulation of specific cell surface markers, such as CD69.

The ability of CD3×CD20 bispecific antibody to upregulate the early activation marker CD69 on human or cynomolgus T cells in whole blood was determined by a 20 hour in vitro FACS assay. Briefly, T cell activation was assessed by incubating freshly isolated human or cynomolgus whole blood (100 μL) in flat bottom 96 well plates with 5-fold (human) or 10-fold (cynomolgus) serial dilutions of Antibody 1, Antibody 4 or Control Ab 5 (concentration range 50 nM to 0.0006 nM) in RPMI+L-glutamate at a final volume of 200 μL for 20 hours at 37° C. Following incubation, the plates were spun down for 5 minutes at 1000 rpm and plasma removed. To measure CD69 upregulation on T cells, a phenotyping cocktail containing directly conjugated antibodies to CD2 and CD69, as well as CD45, CD4, CD8, and either CD19 (human) or CD16 (cynomolgus) was added directly to the blood for 30 minutes at 4° C. Red blood cells were lysed for 15 minutes with 1.5 mL PharmLyse buffer following manufacturer's instructions. Cells were washed two times, resuspended in 200 μL cold PBS+1% FBS, and analyzed by flow cytometry using a BD FACSCanto cytometer. CD4+ T cells were identified by first gating on viable small CD45+ lymphocytes and then gating on CD19−/CD2+/CD4+ T cells (human) or CD16−/CD2+/CD4+ T cells (cynomolgus).

The percent of activated (CD69+) T cells out of total CD2+ effector cells is reported. See Table 22 and also FIG. 21. The results show that CD3×CD20 bispecific antibodies significantly activated T cells as detected by the early activation marker CD69.

TABLE 22

EC$_{50}$ values for target-specific killing in B16F10.9/CD20 cells

| Antibody | % Activated T cells (CD69+) [M] |
|---|---|
| Control Ab 5 | NA |
| CD3 × CD20-wtFc (Ab 4) | 7.907E−11 |
| CD3 × CD20-chimericFc (Antibody 1) | 1.560E−11 |

NA = No Activity.

Example 16. CD3×CD20 Bispecific Antibodies Induce Clustering of T Cells with Target Cells A cell clustering format was used to determine that CD3×CD20 bispecific antibody bridged T-cells with the target cells (CD20+ cells) via its bispecific binding arms. Effector cells were prestained with CFSE, and CD20+ cells were prestained with Violet Cell Tracker for 24 hours, and gated to separate quadrants following incubation with an irrelevant control antibody (Control Antibody 5, irrelevant IgG1 isotype antibody). See FIG. 22A, which depicts no clustering (double-staining) in the cell mixture for treatment with irrelevant antibody. Following incubation with CD3×CD20 bispecific antibody, cell clusters appear due to staining with both CFSE and Violet (see FIG. 22B, in the upper left quadrant on the scatterplot as highlighted by the bold square).

Example 17. Expression of Inhibitory Tim-3 and PD-1 Markers on CD3+ Cells

T cell dysfunction, or exhaustion, occurs in tumor-bearing hosts. Tim-3 and PD-1 receptors have been identified as markers of exhausted T cells in chronic disease states. According to researchers Sakuishi, K. et al. (*J. Exp. Med.* 207(10):2187-2194, 2010), tumor-infiltrating lymphocytes (TILs) that are positive for Tim-3 and PD-1 (Tim-3+PD-1+ TILs) exhibit the most severe exhausted phenotype as defined by failure to proliferate and produce IL-2, TNF, and IFN-γ.

CD3-positive cells were extracted from blood and tumors of NSG mice that were subcutaneously co-implanted with HLA-matched Raji tumor cells and human PBMCs—see Example 12B, hereinabove. Briefly, tumors were allowed to establish in the host for 15 days prior to treatment-then the mice were separated into two treatment groups based on tumor size (see Example 12B). Blood was extracted from the treated (bispecific Ab) and untreated mice on Day 9 from each study group, i.e. Group 1, ~200-400 mm$^3$ or Group 2, ~500-900 mm$^3$. Mice that were untreated (vehicle or the Control Ab) having tumors reaching 1500 mm$^3$ were sacrificed at the end of the study and these tumors were tested for expression of PD1 and Tim-3.

For circulating T cell experiments, viable CD45+CD3+ T cells fractions were selected for marker identification using directly-labeled antibodies to either Tim-3 or PD-1 (commercially available from Biolegend). Tim-3+PD-1+ cells were the predominant fraction of circulating T cells in the blood of untreated animals. However, T cells in the blood of CD20×CD3 bispecific antibody (Ab 1) treated animals displayed lower fractions of Tim-3+PD-1+ cells.

Tumor cells from untreated hosts were separated and stained for viability. FACS analysis was done for viable single cells to sort for CD45+CD3+ cell fractions, which were then tested for Tim-3 or PD-1 expression.

We have found that the inhibitory receptors Tim-3 and PD-1 were expressed on CD3+ TILs in the NSG B cell lymphomas of untreated mice during the experiments described in Example 12B, and that the Tim-3+PD-1+ cells were the predominant fraction of T cell infiltrating tumors.

Example 18. Treatment with CD3×CD20 Bispecific Antibody is more Effective than Anti-CD20+ Antibody in NSG Mice with Established Raji Tumors The efficacy of selected anti-CD3×CD20 bispecific antibodies in reducing established tumors in NSG mice was assessed. NSG mice (NOD/LtSz-scid/IL2Rγnull mice; Jackson Laboratories) were subcutaneously co-implanted with Raji tumor cells (2×10$^6$) and human PBMCs (5×10$^6$)(at Day −14) (similarly to Example 12B herein above).

Figure 23:
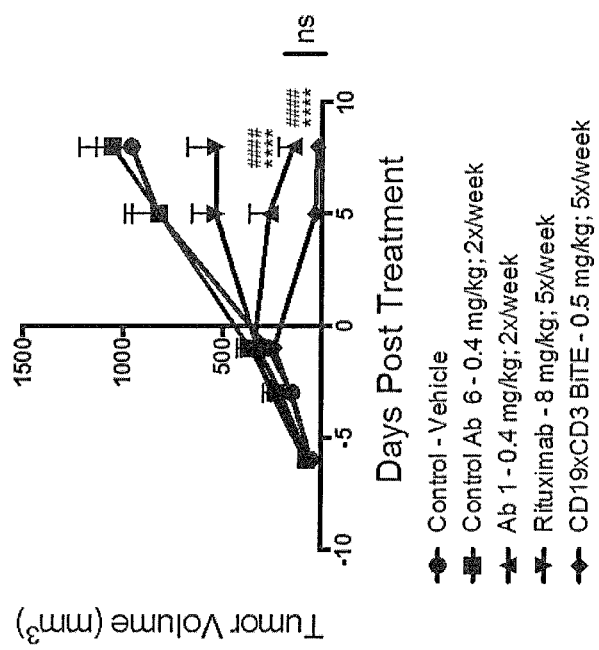
FIG. 23 shows a tumor volume (in mm$^3$) study in NSG mice implanted subcutaneously with a mixture of Raji tumor cells and PBMCs whereas a CD3×CD20 bispecific antibody of the invention (Ab 1) at 0.4 mg/kg, 2×/week (i.p), irrelevant antibody Control Ab 6 at 0.4 mg/kg, 2×/week (i.p), or vehicle was compared to rituximab, anti-CD20 antibody at 8 mg/kg, 5×/week (i.p), and CD19×CD3 BiTE at 0.5 mg/kg, 5×/week (i.v). (For CD19×CD3 BiTE, see Nagorsen D, et al. *Pharmacol Ther.* 2012 December; 136(3):334-42, 2012.) Treatment was administered to mice with established tumors (~100-500 mm3). Data are expressed as mean (SEM) and were subjected to ANOVA analysis. Ab1, which was dosed 2× per week i.p., was comparable to the potency of CD19× CD3 BiTE which was dosed 5×/week i.v. in this in vivo model.
Figure 24:
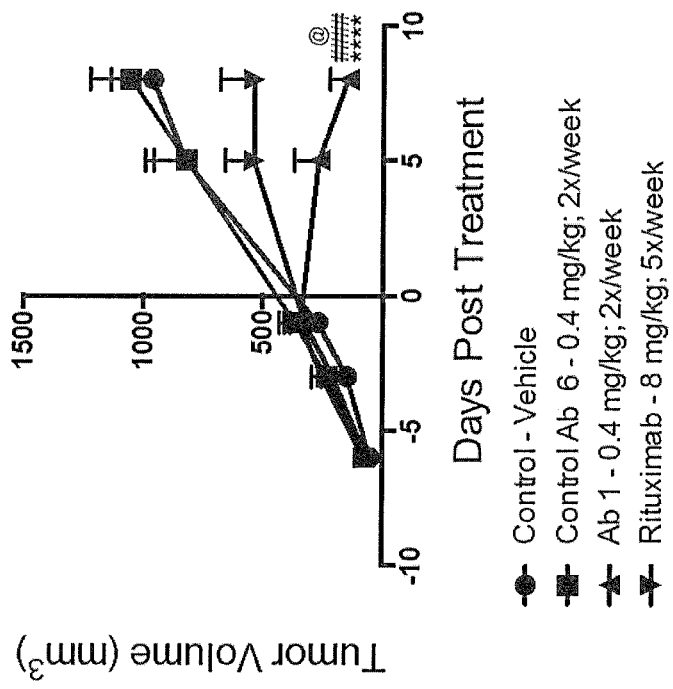
FIG. 24 shows the tumor volume (in mm$^3$) study in NSG mice implanted subcutaneously with Raji/PBMC mixture, analogously to FIG. 23, however ANOVA analysis is provided for Ab 1, Control Ab 6, rituximab and vehicle control. Ab 1 dosed 2× per week was superior to rituximab therapy (dosed at 8 mg/kg; 5×/week i.p.) in suppressing established Raji tumors.

The CD20×CD3 bispecific Ab1 (dosed at 0.4 mg/kg; 2×/week i.p.) was comparable to the CD19×CD3 BiTE (dosed at 0.5 mg/kg; 5×/week i.v.) (FIG. 23) and superior to rituximab therapy (dosed at 8 mg/kg; 5×/week i.p.) (FIG. 24) in suppressing established Raji tumors, thereby demonstrating that Ab1 was effective at treating mammals with large lymphoma masses greater than 0.5 cm in volume.

Example 19. Treatment of CD20+ Melanoma with CD3×CD20 Bispecific Antibody

Researchers have determined that certain subpopulations of melanoma cancers in patients, such as CD20+ melanoma tumor cells, may represent tumor-initiating characteristics and higher risk of disease recurrence (Pinc et al. *Mol Ther.* 20(5):1056-1062, 2012, epub 2012 Feb. 21). The CD20×CD3 bispecific antibody Ab1 demonstrated potent activity against B16F10.9 tumor cells expressing CD20, as it significantly delayed hCD20-transduced B16F10.9 (B16F10.9/CD20) tumor growth in immune-competent mice.

Figures 25A, 25B:
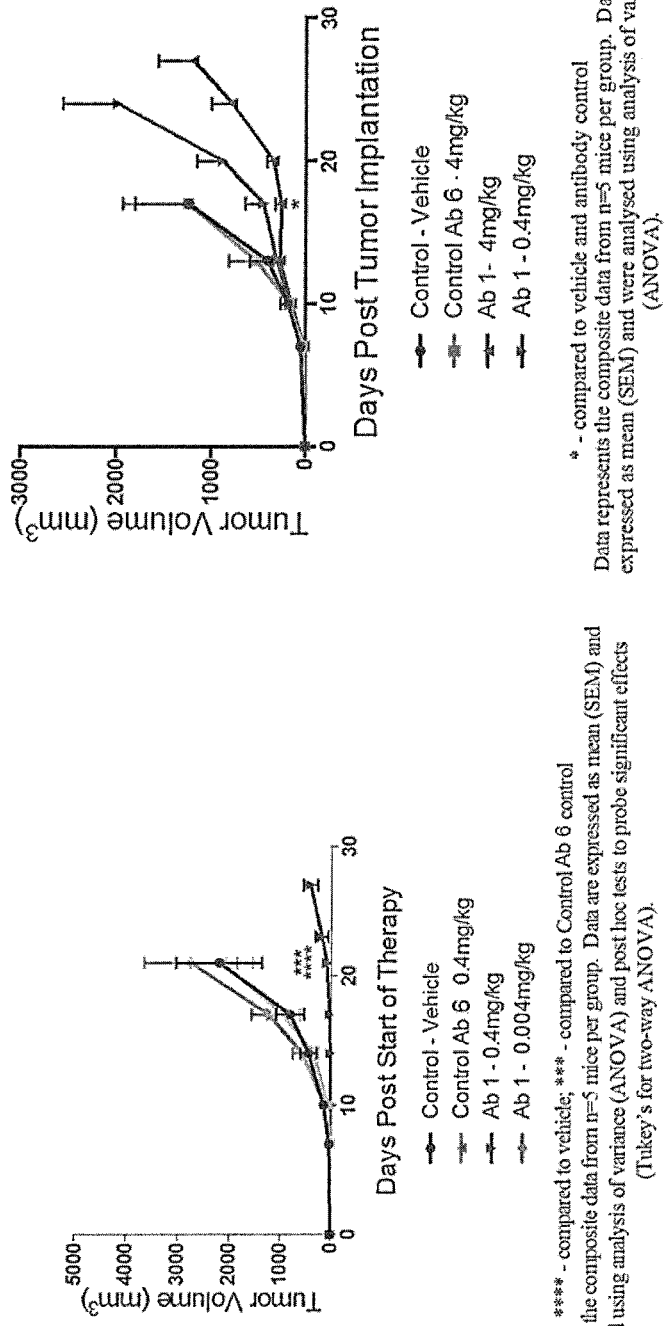
FIGS. 25A and 25B illustrate delayed tumor growth when treatment was initiated simultaneously or subsequently with hCD20/B16F10.9 tumor transplantation in humanized mice treated with CD3×CD20 bispecific antibody.

Mice humanized for CD3 (humanized CD3γε mice) were humanized at the CD20 locus such that the mice expressed both humanized proteins. Humanized CD3/CD20 mice were implanted subcutaneously with 2×10$^5$ B16F10.9 melanoma tumor cells (K. Peters/Charles Lin; Duke University) transduced with human CD20. Starting at Day 0 (day of tumor transplantation), mice were treated intraperitoneally 2 times per week with either vehicle (PBS; n=5), 0.4 mg/kg control Ab5 (control antibody to irrelevant antigen; n=5), 0.4 mg/kg of Ab1 (N=5), or 0.004 mg/kg Ab1 (n=5). Tumor volumes were measured as indicated in FIG. 25A. Mice were sacrificed when tumors reached volume of greater than 1500 mm$^3$. As demonstrated in FIG. 25A, treatment with Ab1 delayed tumor growth when treatment was initiated simultaneously with tumor transplantation.

In a separate experiment, ability of Ab1 to inhibit tumor growth in an already established tumor was also tested (FIG. 25B). Humanized CD3/CD20 mice were implanted subcutaneously with 2×10$^5$ B16F10.9 melanoma tumor cells expressing human CD20. On day 10 post tumor implantation, mice were randomized based on tumor size and organized into the following treatment groups, 5 mice in each group: vehicle (PBS), 4 mg/kg control Ab5 (control antibody to irrelevant antigen), 4 mg/kg of Ab1, or 0.4 mg/kg Ab1. All mice were treated i.p. 2 times a week. Mice were sacrificed when tumors reached volume of greater than 1500 mm$^3$. As shown in FIG. 25B, treatment with Ab1 delayed tumor growth of already established tumors, demonstrating that Ab1 displayed potent activity against B16F10.9 melanoma cells expressing CD20.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method for treating a CD20-positive B-cell cancer in a subject, the method comprising administering to the subject a therapeutic amount of a bispecific antibody comprising a first antigen-binding domain that binds human CD3, a second antigen-binding domain that binds human CD20, and a chimeric heavy chain constant (CH) region tethered to each of the first and second antigen-binding domains, wherein:
- (a) the first antigen-binding domain (AI) that binds human CD3 comprises three heavy chain complementarity determining regions (HCDR1, HCDR2, HCDR3) and three light chain complementarity determining regions (LCDR1, LCDR2, LCDR3), wherein
  A1-HCDR1 comprises the amino acid sequence of SEQ ID NO: 12;
  A1-HCDR2 comprises the amino acid sequence of SEQ ID NO: 14;
  A1-HCDR3 comprises the amino acid sequence of SEQ ID NO: 16;
  A1-LCDR1 comprises the amino acid sequence of SEQ ID NO: 20;
  A1-LCDR2 comprises the amino acid sequence of SEQ ID NO: 22; and
  A1-LCDR3 comprises the amino acid sequence of SEQ ID NO: 24;
- (b) the second antigen-binding domain (A2) that binds human CD20 comprises three heavy chain complementarity determining regions (HCDR1, HCDR2, HCDR3) and three light chain complementarity determining regions (LCDR1, LCDR2, LCDR3), wherein
  A2-HCDR1 comprises the amino acid sequence of SEQ ID NO: 4;
  A2-HCDR2 comprises the amino acid sequence of SEQ ID NO: 6;
  A2-HCDR3 comprises the amino acid sequence of SEQ ID NO: 8;
  A2-LCDR1 comprises the amino acid sequence of SEQ ID NO: 20;
  A2-LCDR2 comprises the amino acid sequence of SEQ ID NO: 22; and
  A2-LCDR3 comprises the amino acid sequence of SEQ ID NO: 24;
- (c) the chimeric CH region comprises an amino acid sequence selected from the group consisting of SEQ ID NO: 26, SEQ ID NO: 28, SEQ ID NO: 30 and SEQ ID NO: 32; and wherein the bispecific antibody binds to human FcγRIIA and FcγRIIB, exhibits a higher binding affinity for human FcγRIIA relative to human FcγRIIB, and exhibits little or no detectable binding affinity to human FcγRI and human FcγRIII, as measured in a surface plasmon resonance assay.

2. The method of claim 1, wherein the therapeutic amount is sufficient to reduce tumor burden, produce tumor regression, inhibit tumor growth or reduce tumor development in the subject.

3. The method of claim 1, wherein the B-cell cancer is selected from the group consisting of: follicular lymphoma, B-cell chronic lymphocytic leukemia, B-cell lymphoblastic lymphoma, Hodgkin lymphoma, Non-Hodgkin's lymphoma, diffuse large B-cell lymphoma, marginal zone lymphoma, Mantle cell lymphoma, hairy cell leukemia and Burkitt lymphoma.

4. The method of claim 1, wherein the subject is afflicted with a tumor that is resistant to, or incompletely responsive to anti-CD20 monospecific therapy alone.

5. The method of claim 4, wherein the subject is afflicted with a tumor that is resistant to, or incompletely responsive to rituximab monotherapy.

6. The method of claim 4, wherein the subject has received an anti-CD20 monospecific antibody therapy at least 1 day to 1 year prior to the administration of the bispecific antibody.

7. The method of claim 4, wherein the anti-CD20 monospecific therapy comprises or consists of an anti-CD20 monospecific antibody.

8. The method of claim 7, wherein the anti-CD20 monospecific antibody is rituximab.

9. The method of claim 1, wherein the therapeutic amount is between about 0.001 mg/kg and about 1 mg/kg.

10. The method of claim 1, wherein the antibody:
- (a) binds to the human FcγRIIA at 25° C. having a $K_D$ value between 10 and 30 µM, as measured in an in vitro assay; or
- (b) binds to the human FcγRIIB at 25° C. having an $K_D$ value between 100 and 250 µM, as measured in an in vitro assay.

11. The method of claim 10, wherein the in vitro assay is a surface plasmon resonance assay.

12. The method of claim 1, wherein the antibody:
- (a) exhibits reduced antibody-dependent-cellular cytotoxicity (ADCC) compared to an antibody comprising a wild-type Fc domain, as measured in an in vitro cytotoxicity assay;
- (b) exhibits negligible or no detectable ADCC;
- (c) exhibits decreased complement dependent cytotoxicity (CDC) compared to an antibody comprising a wild-type Fc domain, as measured in an in vitro cytotoxicity assay;
- (d) exhibits less than 50% cytotoxicity, as detected by measurement of cell lysis in an in vitro assay; or
- (e) exhibits negligible or no detectable CDC.

13. The method of claim 1, wherein the antibody:
- (a) induces decreased T cell-mediated killing of cells bearing Fc receptors, such as NK cells or macrophages, compared to an antibody comprising a wild-type Fc domain; or
- (b) induces decreased killing of T-cells mediated by Fc receptor-bearing cells, such as NK cells or macrophages, compared to an antibody comprising a wild-type Fc domain.

14. The method of claim 1, wherein the human FcγRIII is human FcγRIIIA or human FcγRIIIB.

15. The method of claim 1, wherein the first antigen-binding domain comprises a heavy chain variable region (HCVR) amino acid sequence comprising SEQ ID NO: 10.

16. The method of claim 1, wherein the first antigen-binding domain comprises a light chain variable region (LCVR) amino acid sequence comprising SEQ ID NO: 18.

17. The method of claim 1, wherein the second antigen-binding domain comprises a heavy chain variable region (HCVR) amino acid sequence comprising SEQ ID NO: 2.

18. The method of claim 1, wherein the first antigen-binding domain that specifically binds human CD3 comprises a heavy chain variable region (HCVR) amino acid sequence comprising SEQ ID NO: 10, and a light chain variable region (LCVR) amino acid sequence comprising SEQ ID NO:18.

19. The method of claim 1, wherein the second antigen-binding domain that specifically binds human CD20 comprises a heavy chain variable region (HCVR) amino acid sequence comprising SEQ ID NO: 2, and a light chain variable region (LCVR) amino acid sequence comprising SEQ ID NO:18.

20. The method of claim 1, wherein the first antigen-binding domain comprises (i) a heavy chain variable region (HCVR) comprising the amino acid sequence of SEQ ID NO: 10, and (ii) a light chain variable region (LCVR) comprising the amino acid sequence of SEQ ID NO: 18; and wherein the second antigen-binding domain comprises (iii) a heavy chain variable region (HCVR) comprising the amino acid sequence of SEQ ID NO:2, and a light chain variable region (LCVR) comprising the amino acid sequence of SEQ ID NO: 18.

21. The method of claim 1, wherein a single administration of the bispecific antibody to a subject at a dose of at least about 0.01 mg/kg causes a reduction in the number of B-cells in the subject below detectable levels by about day 2 after administration of the bispecific antibody to the subject.

22. The method of claim 21, wherein the number of B-cells remains below detectable levels until at least about 7 days after administration of a single dose of at least about 0.01 mg/kg of the bispecific antibody to the subject.

23. The method of claim 1, wherein the bispecific antibody comprises a chimeric CH region comprising the amino acid sequence of SEQ ID NO: 26.

24. The method of claim 1, wherein the bispecific antibody comprises a chimeric CH region comprising the amino acid sequence of SEQ ID NO: 28.

25. The method of claim 1, wherein the bispecific antibody comprises a chimeric CH region comprising the amino acid sequence of SEQ ID NO: 30.

26. The method of claim 1, wherein the bispecific antibody comprises a chimeric CH region comprising the amino acid sequence of SEQ ID NO: 32.

27. The method of claim 1, wherein the bispecific antibody comprises a chimeric CH region comprising the amino acid sequence of SEQ ID NO: 26 and a chimeric CH region comprising the amino acid sequence of SEQ ID NO: 28.

28. The method of claim 1, wherein the bispecific antibody comprises a chimeric CH region comprising the amino acid sequence of SEQ ID NO: 30 and a chimeric CH region comprising the amino acid sequence of SEQ ID NO: 32.

29. The method of claim 1, wherein the B-cell cancer is follicular lymphoma.

30. The method of claim 1, wherein the B-cell cancer is diffuse large B-cell lymphoma.

31. The method of claim 1, wherein the B-cell cancer is marginal zone lymphoma.

32. The method of claim 1, wherein the B-cell cancer is mantle cell lymphoma.

* * * * *

UNITED STATES PATENT AND TRADEMARK OFFICE
CERTIFICATE OF CORRECTION

PATENT NO. : 10,550,193 B2
APPLICATION NO. : 14/661334
DATED : February 4, 2020
INVENTOR(S) : Eric Smith et al.

Page 1 of 1

It is certified that error appears in the above-identified patent and that said Letters Patent is hereby corrected as shown below:

In the Claims

Claim 1
Column 141, Line 18 "(Al)" should read --(A1)--

Claim 6
Column 142, Line 20 "claim 4" should read --claim 1--

Column 7
Column 142, Line 24 "claim 4" should read --claim 6--

Signed and Sealed this
Thirty-first Day of March, 2020

Andrei Iancu
*Director of the United States Patent and Trademark Office*

SEQUENCE LISTING

<160> NUMBER OF SEQ ID NOS: 75

<210> SEQ ID NO 1

<211> LENGTH: 382
<212> TYPE: DNA
<213> ORGANISM: Artificial Sequence
<220> FEATURE:
<223> OTHER INFORMATION: Synthetic

<400> SEQUENCE: 1

```
gaagtacagc tggtggagtc tgggggaggc ttggtacagc ctggcaggtc cctgagactc    60
tcctgtgtag cctctggatt cacctttaat gattatgcca tgcactgggt ccggcaagct   120
ccagggaagg gcctggaatg ggtctcagtt attagttgga atagtgatag cataggctat   180
gcggactctg tgaagggccg attcaccatc tccagagaca cgccaagaa ctccctgtat    240
ctgcaaatgc acagtctgag agctgaggac acggccttgt attactgtgc aaaagataat   300
cactatggtt cggggagtta ttactactac caatacggta tggacgtctg gggccaaggg   360
accacggtca ccgtctcctc ag                                            382
```

<210> SEQ ID NO 2
<211> LENGTH: 127
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Tyr Gln Tyr
            100                 105                 110

Gly Met Asp Val Trp Gly Gln Gly Thr Thr Val Thr Val Ser Ser
        115                 120                 125

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggattcacct ttaatgatta tgcc                                           24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Phe Thr Phe Asn Asp Tyr Ala

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attagttgga atagtgatag cata                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Ser Trp Asn Ser Asp Ser Ile
1               5

<210> SEQ ID NO 7
<211> LENGTH: 60
<212> TYPE: DNA
<213> ORGANISM: Artificial Sequence
<220> FEATURE:
<223> OTHER INFORMATION: Synthetic

<400> SEQUENCE: 7
gcaaaagata atcactatgg ttcggggagt tattactact accaatacgg tatggacgtc   60

<210> SEQ ID NO 8
<211> LENGTH: 20
<212> TYPE: PRT
<213> ORGANISM: Artificial Sequence
<220> FEATURE:
<223> OTHER INFORMATION: Synthetic

<400> SEQUENCE: 8

Ala Lys Asp Asn His Tyr Gly Ser Gly Ser Tyr Tyr Tyr Tyr Gln Tyr
1               5                   10                  15
Gly Met Asp Val
            20

<210> SEQ ID NO 9
<211> LENGTH: 369
<212> TYPE: DNA
<213> ORGANISM: Artificial Sequence
<220> FEATURE:
<223> OTHER INFORMATION: Synthetic

<400> SEQUENCE: 9
gaagtgcagc tggtggagtc tgggggaggc ttggtacagc ctggcaggtc cctgagactc   60
tcctgtgcag cctctggatt cacctttgat gattatacca tgcactgggt ccggcaagct  120
ccagggaagg gcctggagtg ggtctcaggt attagttgga atagtggtag tataggctat  180
gcggactctg tgaagggccg attcaccatc tccagagaca cgccaagaa gtccctgtat  240 ctgcaaatga acagtctgag agctgaggac acggccttgt attactgtgc aaaagataat  300
agtggctacg gtcactacta ctacggaatg gacgtctggg gccaagggac cacggtcacc  360
gtcgcctca                                                         369

```
<210> SEQ ID NO 10
<211> LENGTH: 123
<212> TYPE: PRT
<213> ORGANISM: Artificial Sequence
<220> FEATURE:
<223> OTHER INFORMATION: Synthetic

<400> SEQUENCE: 10

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser
        115                 120

<210> SEQ ID NO 11
<211> LENGTH: 24
<212> TYPE: DNA
<213> ORGANISM: Artificial Sequence
<220> FEATURE:
<223> OTHER INFORMATION: Synthetic

<400> SEQUENCE: 11
ggattcacct ttgatgatta tacc                                          24

<210> SEQ ID NO 12
<211> LENGTH: 8
<212> TYPE: PRT
<213> ORGANISM: Artificial Sequence
<220> FEATURE:
<223> OTHER INFORMATION: Synthetic

<400> SEQUENCE: 12

Gly Phe Thr Phe Asp Asp Tyr Thr
1               5

<210> SEQ ID NO 13
<211> LENGTH: 24
<212> TYPE: DNA
<213> ORGANISM: Artificial Sequence
<220> FEATURE:
<223> OTHER INFORMATION: Synthetic

<400> SEQUENCE: 13
attagttgga atagtggtag tata                                          24

<210> SEQ ID NO 14
<211> LENGTH: 8
<212> TYPE: PRT
<213> ORGANISM: Artificial Sequence
<220> FEATURE:
<223> OTHER INFORMATION: Synthetic
```

<400> SEQUENCE: 14

Ile Ser Trp Asn Ser Gly Ser Ile
1               5

<210> SEQ ID NO 15
<211> LENGTH: 48
<212> TYPE: DNA
<213> ORGANISM: Artificial Sequence
<220> FEATURE:
<223> OTHER INFORMATION: Synthetic

<400> SEQUENCE: 15
gcaaaagata atagtggcta cggtcactac tactacggaa tggacgtc           48

<210> SEQ ID NO 16
<211> LENGTH: 16
<212> TYPE: PRT
<213> ORGANISM: Artificial Sequence
<220> FEATURE:
<223> OTHER INFORMATION: Synthetic

<400> SEQUENCE: 16

Ala Lys Asp Asn Ser Gly Tyr Gly His Tyr Tyr Tyr Gly Met Asp Val
1               5                   10                  15

<210> SEQ ID NO 17
<211> LENGTH: 320
<212> TYPE: DNA
<213> ORGANISM: Artificial Sequence
<220> FEATURE:
<223> OTHER INFORMATION: Synthetic

<400> SEQUENCE: 17
gaaatagtga tgacgcagtc tccagccacc ctgtctgtgt ctccagggga aagagccacc    60
ctctcctgca gggccagtca gagtgttagc agcaacttag cctggtacca gcaaaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcac tatattaact ggcctctcac tttcggcgga   300
gggaccaagg tggagatcaa                                               320

<210> SEQ ID NO 18
<211> LENGTH: 108
<212> TYPE: PRT
<213> ORGANISM: Artificial Sequence
<220> FEATURE:
<223> OTHER INFORMATION: Synthetic

<400> SEQUENCE: 18

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg
            100                 105

<210> SEQ ID NO 19
<211> LENGTH: 18
<212> TYPE: DNA
<213> ORGANISM: Artificial Sequence
<220> FEATURE:
<223> OTHER INFORMATION: Synthetic

<400> SEQUENCE: 19
cagagtgtta gcagcaac                                                 18

<210> SEQ ID NO 20
<211> LENGTH: 6
<212> TYPE: PRT
<213> ORGANISM: Artificial Sequence
<220> FEATURE:
<223> OTHER INFORMATION: Synthetic

<400> SEQUENCE: 20

Gln Ser Val Ser Ser Asn
1               5

<210> SEQ ID NO 21
<211> LENGTH: 9
<212> TYPE: DNA
<213> ORGANISM: Artificial Sequence
<220> FEATURE:
<223> OTHER INFORMATION: Synthetic

<400> SEQUENCE: 21 ggtgcatcc                                                            9

<210> SEQ ID NO 22
<211> LENGTH: 3
<212> TYPE: PRT
<213> ORGANISM: Artificial Sequence
<220> FEATURE:
<223> OTHER INFORMATION: Synthetic

<400> SEQUENCE: 22

Gly Ala Ser
1

<210> SEQ ID NO 23
<211> LENGTH: 27
<212> TYPE: DNA
<213> ORGANISM: Artificial Sequence
<220> FEATURE:
<223> OTHER INFORMATION: Synthetic

<400> SEQUENCE: 23
cagcactata ttaactggcc tctcact                                       27

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Gln His Tyr Ile Asn Trp Pro Leu Thr
1               5

<210> SEQ ID NO 25
<211> LENGTH: 981
<212> TYPE: DNA
<213> ORGANISM: Artificial Sequence
<220> FEATURE:
<223> OTHER INFORMATION: Synthetic

<400> SEQUENCE: 25

```
gccagcacaa aaggtcctag cgttttttcca cttgccccat gttcaaggtc aacctccgaa    60
agtaccgccg ctcttggctg tctcgtaaaa gattattttc ccgaacctgt aactgtctcc   120
tggaactccg gcgcactcac ttccggcgta cataccttcc ccgctgtcct ccaatcttcc   180
ggtctctact ccctgtcttc tgttgtcact gttccatcat cctcactcgg cacaaaaaca   240
tatacctgca acgttgatca caagccaagt aataccaaag ttgataagcg cgtcgaatcc   300
aaatacggtc cccctgccc accgtgccca gcaccacctg tggcaggacc atcagtcttc   360
ctgttccccc caaacccaa ggacactctc atgatctccc ggaccccctga ggtcacgtgc   420
gtggtggtgg acgtgagcca ggaagacccc gaggtccagt tcaactggta cgtggatggc   480
gtggaggtgc ataatgccaa gacaaagccg cgggaggagc agttcaacag cacgtaccgt   540
gtggtcagcg tcctcaccgt cctgcaccag gactggctga acggcaagga gtacaagtgc   600
aaggtctcca acaaaggcct cccgtcctcc atcgagaaaa ccatctccaa agccaaaggg   660
cagccccgag agccacaggt gtacaccctg cccccatccc aggaggagat gaccaagaac   720
caggtcagcc tgacctgcct ggtcaaaggc ttctacccca gcgacatcgc cgtggagtgg   780
gagagcaatg ggcagccgga gaacaactac aagaccacgc ctcccgtgct ggactccgac   840
ggctccttct tcctctacag caggctcacc gtggacaaga gcaggtggca ggaggggaat   900
gtcttctcat gctccgtgat gcatgaggct ctgcacaacc actacacaca gaagtccctc   960
tccctgtctc tgggtaaatg a                                              981
```

<210> SEQ ID NO 26
<211> LENGTH: 326
<212> TYPE: PRT
<213> ORGANISM: Artificial Sequence
<220> FEATURE:
<223> OTHER INFORMATION: Synthetic

<400> SEQUENCE: 26

```
Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
```

```
                130             135                 140
Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Leu Gly Lys
                325

<210> SEQ ID NO 27
<211> LENGTH: 981
<212> TYPE: DNA
<213> ORGANISM: Artificial Sequence
<220> FEATURE:
<223> OTHER INFORMATION: Synthetic

<400> SEQUENCE: 27
gccagcacaa aaggtcctag cgttttttcca cttgccccat gttcaaggtc aacctccgaa      60
agtaccgccg ctcttggctg tctcgtaaaa gattattttc ccgaacctgt aactgtctcc     120
tggaactccg gcgcactcac ttccggcgta catacctccc ccgctgtcct ccaatcttcc     180
ggtctctact ccctgtcttc tgttgtcact gttccatcat cctcactcgg cacaaaaaca     240
tatacctgca acgttgatca caagccaagt aataccaaag ttgataagcg cgtcgaatcc     300
aaatacggtc cccctgccc accgtgccca gcaccacctg tggcaggacc atcagtcttc     360
ctgttccccc caaaacccaa ggacactctc atgatctccc ggaccctga ggtcacgtgc     420 gtggtggtgg acgtgagcca ggaagacccc gaggtccagt tcaactggta cgtggatggc     480
gtggaggtgc ataatgccaa gacaaagccg cgggaggagc agttcaacag cacgtaccgt     540
gtggtcagcg tcctcaccgt cctgcaccag gactggctga acggcaagga gtacaagtgc     600
aaggtctcca acaaggcct cccgtcctcc atcgagaaaa ccatctccaa agccaaaggg     660
cagccccgag agccacaggt gtacaccctg cccccatccc aggaggagat gaccaagaac     720
caggtcagcc tgacctgcct ggtcaaaggc ttctacccca gcgacatcgc cgtggagtgg     780
gagagcaatg ggcagccgga gaacaactac aagaccacgc ctcccgtgct ggactccgac     840
ggctccttct tcctctacag caggctcacc gtggacaaga gcaggtggca ggaggggaat     900
gtcttctcat gctccgtgat gcatgaggct ctgcacaaca gattcacaca gaagtccctc     960
```
tccctgtctc tgggtaaatg a								981

<210> SEQ ID NO 28
<211> LENGTH: 326
<212> TYPE: PRT
<213> ORGANISM: Artificial Sequence
<220> FEATURE:
<223> OTHER INFORMATION: Synthetic

<400> SEQUENCE: 28

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Gln Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Arg
        275                 280                 285

Leu Thr Val Asp Lys Ser Arg Trp Gln Glu Gly Asn Val Phe Ser Cys
    290                 295                 300

Ser Val Met His Glu Ala Leu His Asn Arg Phe Thr Gln Lys Ser Leu
305                 310                 315                 320

Ser Leu Ser Leu Gly Lys
                325
```

<210> SEQ ID NO 29
<211> LENGTH: 990

<212> TYPE: DNA
<213> ORGANISM: Artificial Sequence
<220> FEATURE:
<223> OTHER INFORMATION: Synthetic

<400> SEQUENCE: 29

```
gcctccacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
aaatcttgtg acaaaactca cacatgccca ccgtgcccag caccacctgt ggcaggacca   360
tcagtcttcc tgttcccccc aaaacccaag gacactctca tgatctcccg gacccctgag   420
gtcacgtgcg tggtggtgga cgtgagccag gaagaccccg aggtccagtt caactggtac   480
gtggatggcg tggaggtgca taatgccaag acaaagccgc gggaggagca gttcaacagc   540
acgtaccgtg tggtcagcgt cctcaccgtc ctgcaccagg actggctgaa cggcaaggag   600
tacaagtgca aggtctccaa caaaggcctc ccgtcctcca tcgagaaaac catctccaaa   660
gccaaagggc agccccgaga accacaggtg tacaccctgc ccccatcccg ggatgagctg   720
accaagaacc aggtcagcct gacctgcctg gtcaaaggct tctatcccag cgacatcgcc   780
gtggagtggg agagcaatgg gcagccggag aacaactaca agaccacgcc tcccgtgctg   840
gactccgacg gctccttctt cctctacagc aagctcaccg tggacaagag caggtggcag   900
caggggaacg tcttctcatg ctccgtgatg catgaggctc tgcacaacca ctacacgcag   960
aagtccctct ccctgtctcc gggtaaatga                                    990
```

<210> SEQ ID NO 30
<211> LENGTH: 329
<212> TYPE: PRT
<213> ORGANISM: Artificial Sequence
<220> FEATURE:
<223> OTHER INFORMATION: Synthetic

<400> SEQUENCE: 30

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Pro Val Ala Gly Pro Ser Val Phe Leu Phe Pro Pro Lys
        115                 120                 125
Pro Lys Asp Thr Leu Met Ile Ser Arg Thr Pro Glu Val Thr Cys Val
    130                 135                 140
Val Val Asp Val Ser Gln Glu Asp Pro Glu Val Gln Phe Asn Trp Tyr
```

```
           145                 150                 155                 160
Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325
```

<210> SEQ ID NO 31
<211> LENGTH: 990
<212> TYPE: DNA
<213> ORGANISM: Artificial Sequence
<220> FEATURE:
<223> OTHER INFORMATION: Synthetic

<400> SEQUENCE: 31

| | | | | | |
|---|---|---|---|---|---|
| gcctccacca | agggcccatc | ggtcttcccc | ctggcaccct | cctccaagag | cacctctggg | 60 |
| ggcacagcgg | ccctgggctg | cctggtcaag | gactacttcc | ccgaaccggt | gacggtgtcg | 120 |
| tggaactcag | gcgccctgac | cagcggcgtg | cacaccttcc | cggctgtcct | acagtcctca | 180 |
| ggactctact | ccctcagcag | cgtggtgacc | gtgccctcca | gcagcttggg | cacccagacc | 240 |
| tacatctgca | acgtgaatca | caagcccagc | aacaccaagg | tggacaagaa | agttgagccc | 300 |
| aaatcttgtg | acaaaactca | cacatgccca | ccgtgcccag | caccacctgt | ggcaggacca | 360 |
| tcagtcttcc | tgttcccccc | aaaacccaag | gacactctca | tgatctcccg | gacccctgag | 420 |
| gtcacgtgcg | tggtggtgga | cgtgagccag | gaagaccccg | aggtccagtt | caactggtac | 480 |
| gtggatggcg | tggaggtgca | taatgccaag | acaaagccgc | gggaggagca | gttcaacagc | 540 |
| acgtaccgtg | tggtcagcgt | cctcaccgtc | ctgcaccagg | actggctgaa | cggcaaggag | 600 |
| tacaagtgca | aggtctccaa | caaaggcctc | ccgtcctcca | tcgagaaaac | catctccaaa | 660 |
| gccaaagggc | agccccgaga | accacaggtg | tacaccctgc | ccccatcccg | ggatgagctg | 720 |
| accaagaacc | aggtcagcct | gacctgcctg | gtcaaaggct | tctatcccag | cgacatcgcc | 780 |
| gtggagtggg | agagcaatgg | gcagccggag | aacaactaca | agaccacgcc | tcccgtgctg | 840 |
| gactccgacg | gctccttctt | cctctacagc | aagctcaccg | tggacaagag | caggtggcag | 900 |
| caggggaacg | tcttctcatg | ctccgtgatg | catgaggctc | tgcacaacag | attcacgcag | 960 |
| aagtccctct | ccctgtctcc | gggtaaatga | | | | 990 |

<210> SEQ ID NO 32
<211> LENGTH: 329
<212> TYPE: PRT
<213> ORGANISM: Artificial Sequence
<220> FEATURE:
<223> OTHER INFORMATION: Synthetic

<400> SEQUENCE: 32

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser Gln Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Gly Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Asp Glu Leu
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn Arg Phe Thr Gln
305                 310                 315                 320

Lys Ser Leu Ser Leu Ser Pro Gly Lys
                325
```

<210> SEQ ID NO 33
<211> LENGTH: 981
<212> TYPE: DNA
<213> ORGANISM: Artificial Sequence
<220> FEATURE:

<223> OTHER INFORMATION: Synthetic

<400> SEQUENCE: 33

| gccagcacaa aaggtcctag cgttttccca cttgccccat gttcaaggtc aacctccgaa | 60 |
|---|---|
| agtaccgccg ctcttggctg tctcgtaaaa gattattttc ccgaacctgt aactgtctcc | 120 |
| tggaactccg gcgcactcac ttccggcgta catacctttcc ccgctgtcct ccaatcttcc | 180 |
| ggtctctact ccctgtcttc tgttgtcact gttccatcat cctcactcgg cacaaaaaca | 240 |
| tatacctgca acgttgatca caagccaagt aataccaaag ttgataagcg cgtcgaatcc | 300 |
| aaatacggtc cccctgccc ccatgtccc gctccacctg tggctggtcc ctctgttttc | 360 |
| ctttttcccc ctaaacccaa agataccctc atgatttcca gaaccccga ggtcacctgc | 420 |
| gtcgtcgttg atgtaagcca agaagatccc gaagtccagt tcaattggta tgtagacggt | 480 |
| gttgaagtcc ataatgcaaa acaaaaccc agagaggaac agtttaattc aacctatcgt | 540 |
| gtcgttagcg tactcaccgt tcttcatcaa gactggctca atggaaaaga atataaatgt | 600 |
| aaagttagca acaaaggtct gcccagttca atcgaaaaaa caattagcaa agccaaaggc | 660 |
| caacctcgcg aaccccaagt ctataccttg ccccttctc aggaagaaat gaccaaaaac | 720 |
| caagtttcac tcacatgcct cgtaaaagga ttctatccat cagacattgc agtagaatgg | 780 |
| gaatctaacg gccaacctga aaataattac aaaaccactc ctcctgtcct cgattctgac | 840 |
| ggctctttt tcctttactc cagattgact gttgataaat cccgctggca ggaaggtaac | 900 |
| gttttttctt gttctgtgat gcacgaagcc ctccataaca gattcactca aaaatctctt | 960 |
| tctctctccc tgggcaaata a | 981 |

<210> SEQ ID NO 34
<211> LENGTH: 645
<212> TYPE: DNA
<213> ORGANISM: Artificial Sequence
<220> FEATURE:
<223> OTHER INFORMATION: Synthetic

<400> SEQUENCE: 34

| gaaatagtga tgacgcagtc tccagccacc ctgtctgtgt ctccagggga aagagccacc | 60 |
|---|---|
| ctctcctgca gggccagtca gagtgttagc agcaacttag cctggtacca gcagaaacct | 120 |
| ggccaggctc ccaggctcct catctatggt gcatccacca gggccactgg tatcccagcc | 180 |
| aggttcagtg gcagtgggtc tgggacagag ttcactctca ccatcagcag cctgcagtct | 240 |
| gaagattttg cagtttatta ctgtcagcac tatattaact ggcctctcac tttcggcgga | 300 |
| gggaccaagg tggagatcaa acgaactgtg gctgcaccat ctgtcttcat cttcccgcca | 360 |
| tctgatgagc agttgaaatc tggaactgcc tctgttgtgt gcctgctgaa taacttctat | 420 |
| cccagagagg ccaaagtaca gtggaaggtg gataacgccc tccaatcggg taactcccag | 480 |
| gagagtgtca cagagcagga cagcaaggac agcacctaca gcctcagcag cacccctgacg | 540 |
| ctgagcaaag cagactacga gaaacacaaa gtctacgcct gcgaagtcac ccatcagggc | 600 |
| ctgagctcgc ccgtcacaaa gagcttcaac aggggagagt gttag | 645 |

<210> SEQ ID NO 35
<211> LENGTH: 214
<212> TYPE: PRT
<213> ORGANISM: Artificial Sequence
<220> FEATURE:
<223> OTHER INFORMATION: Synthetic

<400> SEQUENCE: 35

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Ile Asn Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 36
<211> LENGTH: 1362
<212> TYPE: DNA
<213> ORGANISM: Artificial Sequence
<220> FEATURE:
<223> OTHER INFORMATION: Synthetic

<400> SEQUENCE: 36

```
gaagtgcagc tggtggagtc tgggggaggc ttggtacagc ctggcaggtc cctgagactc     60
tcctgtgtag cctctggatt cacctttaat gattatgcca tgcactgggt ccggcaagct    120
ccagggaagg gcctggaatg ggtctcagtt attagttgga atagtgatag cataggctat    180
gcggactctg tgaagggccg attcaccatc tccagagaca acgccaagaa ctccctgtat    240
ctgcaaatgc acagtctgag agctgaggac acggccttgt attactgtgc aaaagataat    300
cactatggtt cggggagtta ttactactac caatacggta tggacgtctg ggggccaaggg    360
accacggtca ccgtctcctc agccagcaca aaaggtccta gcgttttttcc acttgccccca    420
tgttcaaggt caacctccga agtaccgcc gctcttggct gtctcgtaaa agattatttt    480
cccgaacctg taactgtctc ctggaactcc ggcgcactca cttccggcgt acataccttc    540
cccgctgtcc tccaatcttc cggtctctac tccctgtctt ctgttgtcac tgttccatca    600
tcctcactcg gcacaaaaac atatacctgc aacgttgatc acaagccaag taataccaaa    660
gttgataagc gcgtcgaatc caaatacggt cccccctgcc caccgtgccc agcaccacct    720
gtggcaggac catcagtctt cctgttcccc ccaaaaccca aggacactct catgatctcc    780
```

```
cggacccctg aggtcacgtg cgtggtggtg gacgtgagcc aggaagaccc cgaggtccag    840
ttcaactggt acgtggatgg cgtggaggtg cataatgcca agacaaagcc gcgggaggag    900
cagttcaaca gcacgtaccg tgtggtcagc gtcctcaccg tcctgcacca ggactggctg    960
aacggcaagg agtacaagtg caaggtctcc aacaaaggcc tcccgtcctc catcgagaaa   1020
accatctcca aagccaaagg gcagccccga gagccacagg tgtacaccct gcccccatcc   1080
caggaggaga tgaccaagaa ccaggtcagc ctgacctgcc tggtcaaagg cttctacccc   1140
agcgacatcg ccgtggagtg ggagagcaat gggcagccgg agaacaacta caagaccacg   1200
cctcccgtgc tggactccga cggctccttc ttcctctaca gcaggctcac cgtggacaag   1260
agcaggtggc aggaggggaa tgtcttctca tgctccgtga tgcatgaggc tctgcacaac   1320
cactacacac agaagtccct ctccctgtct ctgggtaaat ga                      1362
```

<210> SEQ ID NO 37
<211> LENGTH: 453
<212> TYPE: PRT
<213> ORGANISM: Artificial Sequence
<220> FEATURE:
<223> OTHER INFORMATION: Synthetic

<400> SEQUENCE: 37

```
Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr
            20                  25                  30

Ala Met His Trp Val Arg Gln Ala Pro Gly Lys Gly Leu Glu Trp Val
        35                  40                  45

Ser Val Ile Ser Trp Asn Ser Asp Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met His Ser Leu Arg Ala Glu Asp Thr Ala Leu Tyr Tyr Cys
                85                  90                  95

Ala Lys Asp Asn His Tyr Gly Ser Gly Ser Tyr Tyr Tyr Tyr Gln Tyr
            100                 105                 110

Gly Met Asp Val Trp Gly Gln Gly Thr Thr Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
        195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Pro
225                 230                 235                 240

Val Ala Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
```

|     |     |     |     | 260 |     |     |     | 265 |     |     |     | 270 |     |
| --- | --- | --- | --- | --- | --- | --- | --- | --- | --- | --- | --- | --- | --- |
| Ser | Gln | Glu | Asp | Pro | Glu | Val | Gln | Phe | Asn | Trp | Tyr | Val | Asp | Gly | Val |
|     |     |     | 275 |     |     |     |     | 280 |     |     |     |     | 285 |     |     |

Glu Val His Asn Ala Lys Thr Lys Pro Arg Glu Glu Gln Phe Asn Ser
    290                295              300

Thr Tyr Arg Val Val Ser Val Leu Thr Val Leu His Gln Asp Trp Leu
305              310              315              320

Asn Gly Lys Glu Tyr Lys Cys Lys Val Ser Asn Lys Gly Leu Pro Ser
            325              330              335

Ser Ile Glu Lys Thr Ile Ser Lys Ala Lys Gly Gln Pro Arg Glu Pro
        340              345              350

Gln Val Tyr Thr Leu Pro Pro Ser Gln Glu Glu Met Thr Lys Asn Gln
        355              360              365

Val Ser Leu Thr Cys Leu Val Lys Gly Phe Tyr Pro Ser Asp Ile Ala
    370              375              380

Val Glu Trp Glu Ser Asn Gly Gln Pro Glu Asn Asn Tyr Lys Thr Thr
385              390              395              400

Pro Pro Val Leu Asp Ser Asp Gly Ser Phe Phe Leu Tyr Ser Arg Leu
            405              410              415

Thr Val Asp Lys Ser Arg Trp Gln Glu Gly Asn Val Phe Ser Cys Ser
        420              425              430

Val Met His Glu Ala Leu His Asn His Tyr Thr Gln Lys Ser Leu Ser
    435              440              445

Leu Ser Leu Gly Lys
    450

<210> SEQ ID NO 38
<211> LENGTH: 1350
<212> TYPE: DNA
<213> ORGANISM: Artificial Sequence
<220> FEATURE:
<223> OTHER INFORMATION: Synthetic

<400> SEQUENCE: 38

| | | | | | |
|---|---|---|---|---|---|
| gaagtgcagc | tggtggagtc | tgggggaggc | ttggtacagc | ctggcaggtc | cctgagactc | 60 |
| tcctgtgcag | cctctggatt | cacctttgat | gattatacca | tgcactgggt | ccggcaagct | 120 |
| ccagggaagg | gcctggagtg | ggtctcaggt | attagttgga | atagtggtag | tataggctat | 180 |
| gcggactctg | tgaagggccg | attcaccatc | tccagagaca | acgccaagaa | gtccctgtat | 240 |
| ctgcaaatga | acagtctgag | agctgaggac | acggccttgt | attactgtgc | aaaagataat | 300 |
| agtggctacg | gtcactacta | ctacggaatg | gacgtctggg | gccaagggac | cacggtcacc | 360 |
| gtcgcctcag | ccagcacaaa | aggtcctagc | gttttccac | ttgccccatg | ttcaaggtca | 420 |
| acctccgaaa | gtaccgccgc | tcttggctgt | ctcgtaaaag | attatttcc | cgaacctgta | 480 |
| actgtctcct | ggaactccgg | cgcactcact | tccggcgtac | ataccttccc | cgctgtcctc | 540 |
| caatcttccg | gtctctactc | cctgtcttct | gttgtcactg | ttccatcatc | ctcactcggc | 600 |
| acaaaaacat | atacctgcaa | cgttgatcac | aagccaagta | ataccaaagt | tgataagcgc | 660 |
| gtcgaatcca | aatacggtcc | ccctgccca | ccgtgcccag | caccacctgt | ggcaggacca | 720 |
| tcagtcttcc | tgttccccc | aaaacccaag | gacactctca | tgatctcccg | gacccctgag | 780 |
| gtcacgtgcg | tggtggtgga | cgtgagccag | gaagacccg | aggtccagtt | caactggtac | 840 |
| gtggatggcg | tggaggtgca | taatgccaag | acaaagccgc | gggaggagca | gttcaacagc | 900 |
| acgtaccgtg | tggtcagcgt | cctcaccgtc | ctgcaccagg | actggctgaa | cggcaaggag | 960 |

| | | | |
|---|---|---|---|
| tacaagtgca | aggtctccaa | caaaggcctc | ccgtcctcca tcgagaaaac catctccaaa | 1020 |
| gccaaagggc | agccccgaga | gccacaggtg | tacaccctgc ccccatccca ggaggagatg | 1080 |
| accaagaacc | aggtcagcct | gacctgcctg | gtcaaaggct tctacccag cgacatcgcc | 1140 |
| gtggagtggg | agagcaatgg | gcagccggag | aacaactaca agaccacgcc tcccgtgctg | 1200 |
| gactccgacg | gctccttctt | cctctacagc | aggctcaccg tggacaagag caggtggcag | 1260 |
| gagggggaatg | tcttctcatg | ctccgtgatg | catgaggctc tgcacaacag attcacacag | 1320 |
| aagtccctct | ccctgtctct | gggtaaatga | | 1350 |

<210> SEQ ID NO 39
<211> LENGTH: 1350
<212> TYPE: DNA
<213> ORGANISM: Artificial Sequence
<220> FEATURE:
<223> OTHER INFORMATION: Synthetic

<400> SEQUENCE: 39

| | | | |
|---|---|---|---|
| gaagtgcagc | tggtggagtc | tgggggaggc | ttggtacagc ctggcaggtc cctgagactc | 60 |
| tcctgtgcag | cctctggatt | cacctttgat | gattatacca tgcactgggt ccggcaagct | 120 |
| ccagggaagg | gcctggagtg | ggtctcaggt | attagttgga atagtggtag tataggctat | 180 |
| gcggactctg | tgaagggccg | attcaccatc | tccagagaca acgccaagaa gtccctgtat | 240 |
| ctgcaaatga | acagtctgag | agctgaggac | acggccttgt attactgtgc aaaagataat | 300 |
| agtggctacg | tcactactta | ctacggaatg | gacgtctggg gccaagggac cacggtcacc | 360 |
| gtcgcctcag | ccagcacaaa | aggtcctagc | gttttccac ttgccccatg ttcaaggtca | 420 |
| acctccgaaa | gtaccgccgc | tcttggctgt | ctcgtaaaag attattttcc cgaacctgta | 480 |
| actgtctcct | ggaactccgg | cgcactcact | tccggcgtac atacccttcc cgctgtcctc | 540 |
| caatcttccg | gtctctactc | cctgtcttct | gttgtcactg ttccatcatc ctcactcggc | 600 |
| acaaaaacat | atacctgcaa | cgttgatcac | aagccaagta ataccaaagt tgataagcgc | 660 |
| gtcgaatcca | aatacggtcc | ccctgcccc | ccatgtcccg ctccacctgt ggctggtccc | 720 |
| tctgttttcc | ttttcccccc | taaacccaaa | gatacctctca tgatttccag aaccccgag | 780 |
| gtcacctgcg | tcgtcgttga | tgtaagccaa | gaagatcccg aagtccagtt caattggtat | 840 |
| gtagacggtg | ttgaagtcca | taatgcaaaa | acaaaaccca gagaggaaca gttaattca | 900 |
| acctatcgtg | tcgttagcgt | actcaccgtt | cttcatcaag actggctcaa tggaaaagaa | 960 |
| tataaatgta | aagttagcaa | caaaggtctg | cccagttcaa tcgaaaaaac aattagcaaa | 1020 |
| gccaaaggcc | aacctcgcga | accccaagtc | tataccttgc cccttctca ggaagaaatg | 1080 |
| accaaaaacc | aagtttcact | cacatgcctc | gtaaaaggat tctatccatc agacattgca | 1140 |
| gtagaatggg | aatctaacgg | ccaacctgaa | aataattaca aaaccactcc tcctgtcctc | 1200 |
| gattctgacg | gctcttttt | cctttactcc | agattgactg ttgataaatc ccgctggcag | 1260 |
| gaaggtaacg | ttttttcttg | ttctgtgatg | cacgaagccc tccataacag attcactcaa | 1320 |
| aaatctcttt | ctctctccct | gggcaaataa | | 1350 |

<210> SEQ ID NO 40
<211> LENGTH: 449
<212> TYPE: PRT
<213> ORGANISM: Artificial Sequence
<220> FEATURE:
<223> OTHER INFORMATION: Synthetic

```
<400> SEQUENCE: 40

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Asn Ser Gly Tyr Gly His Tyr Tyr Tyr Gly Met Asp Val
            100                 105                 110

Trp Gly Gln Gly Thr Thr Val Thr Val Ala Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415
```

Ser Arg Trp Gln Glu Gly Asn Val Phe Ser Cys Ser Val Met His Glu
                420                 425                 430

Ala Leu His Asn Arg Phe Thr Gln Lys Ser Leu Ser Leu Ser Leu Gly
            435                 440                 445

Lys

<210> SEQ ID NO 41
<211> LENGTH: 1371
<212> TYPE: DNA
<213> ORGANISM: Artificial Sequence
<220> FEATURE:
<223> OTHER INFORMATION: Synthetic

<400> SEQUENCE: 41

| | | | | |
|---|---|---|---|---|
| gaagtacagc | tggtggagtc | tgggggaggc | ttggtacagc | ctggcaggtc cctgagactc | 60 |
| tcctgtgtag | cctctggatt | cacctttaat | gattatgcca | tgcactgggt ccggcaagct | 120 |
| ccagggaagg | gcctggaatg | ggtctcagtt | attagttgga | atagtgatag cataggctat | 180 |
| gcggactctg | tgaagggccg | attcaccatc | tccagagaca | acgccaagaa ctccctgtat | 240 |
| ctgcaaatgc | acagtctgag | agctgaggac | acggccttgt | attactgtgc aaaagataat | 300 |
| cactatggtt | cggggagtta | ttactactac | caatacggta | tggacgtctg gggccaaggg | 360 |
| accacggtca | ccgtctcctc | agcctccacc | aagggcccat | cggtcttccc cctggcaccc | 420 |
| tcctccaaga | gcacctctgg | gggcacagcg | gccctgggct | gcctggtcaa ggactacttc | 480 |
| cccgaaccgg | tgacggtgtc | gtggaactca | ggcgccctga | ccagcggcgt gcacaccttc | 540 |
| ccggctgtcc | tacagtcctc | aggactctac | tccctcagca | gcgtggtgac cgtgccctcc | 600 |
| agcagcttgg | gcacccagac | ctacatctgc | aacgtgaatc | acaagcccag caacaccaag | 660 |
| gtggacaaga | aagttgagcc | caaatcttgt | gacaaaactc | acacatgccc accgtgccca | 720 |
| gcacccctg | tggcaggacc | atcagtcttc | ctgttccccc | caaaacccaa ggacactctc | 780 |
| atgatctccc | ggacccctga | ggtcacgtgc | gtggtggtgg | acgtgagcca ggaagacccc | 840 |
| gaggtccagt | tcaactggta | cgtggatggc | gtggaggtgc | ataatgccaa gacaaagccg | 900 |
| cgggaggagc | agttcaacag | cacgtaccgt | gtggtcagcg | tcctcaccgt cctgcaccag | 960 |
| gactggctga | acggcaagga | gtacaagtgc | aaggtctcca | acaaaggcct cccgtcctcc | 1020 |
| atcgagaaaa | ccatctccaa | agccaaaggg | cagccccgag | aaccacaggt gtacaccctg | 1080 |
| cccccatccc | gggatgagct | gaccaagaac | caggtcagcc | tgacctgcct ggtcaaaggc | 1140 |
| ttctatccca | gcgacatcgc | cgtggagtgg | gagagcaatg | gcagccgga gaacaactac | 1200 |
| aagaccacgc | ctcccgtgct | ggactccgac | ggctccttct | tcctctacag caagctcacc | 1260 |
| gtggacaaga | gcaggtggca | gcaggggaac | gtcttctcat | gctccgtgat gcatgaggct | 1320 |
| ctgcacaacc | actacacgca | gaagtccctc | tccctgtctc | cgggtaaatg a | 1371 |

<210> SEQ ID NO 42
<211> LENGTH: 456
<212> TYPE: PRT
<213> ORGANISM: Artificial Sequence
<220> FEATURE:
<223> OTHER INFORMATION: Synthetic

<400> SEQUENCE: 42

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asn Asp Tyr

```
                      20                  25                  30
        Ala Met His Trp Val Arg Gln Ala Pro Gly Lys Gly Leu Glu Trp Val
                          35                  40                  45
        Ser Val Ile Ser Trp Asn Ser Asp Ser Ile Gly Tyr Ala Asp Ser Val
                          50                  55                  60
        Lys Gly Arg Phe Thr Ile Ser Arg Asp Asn Ala Lys Asn Ser Leu Tyr
         65                  70                  75                  80
        Leu Gln Met His Ser Leu Arg Ala Glu Asp Thr Ala Leu Tyr Tyr Cys
                          85                  90                  95
        Ala Lys Asp Asn His Tyr Gly Ser Gly Ser Tyr Tyr Tyr Gln Tyr
                         100                 105                 110
        Gly Met Asp Val Trp Gly Gln Gly Thr Thr Val Thr Val Ser Ser Ala
                         115                 120                 125
        Ser Thr Lys Gly Pro Ser Val Phe Pro Leu Ala Pro Ser Ser Lys Ser
                         130                 135                 140
        Thr Ser Gly Gly Thr Ala Ala Leu Gly Cys Leu Val Lys Asp Tyr Phe
        145                 150                 155                 160
        Pro Glu Pro Val Thr Val Ser Trp Asn Ser Gly Ala Leu Thr Ser Gly
                         165                 170                 175
        Val His Thr Phe Pro Ala Val Leu Gln Ser Ser Gly Leu Tyr Ser Leu
                         180                 185                 190
        Ser Ser Val Val Thr Val Pro Ser Ser Ser Leu Gly Thr Gln Thr Tyr
                         195                 200                 205
        Ile Cys Asn Val Asn His Lys Pro Ser Asn Thr Lys Val Asp Lys Lys
                         210                 215                 220
        Val Glu Pro Lys Ser Cys Asp Lys Thr His Thr Cys Pro Pro Cys Pro
        225                 230                 235                 240
        Ala Pro Pro Val Ala Gly Pro Ser Val Phe Leu Phe Pro Pro Lys Pro
                         245                 250                 255
        Lys Asp Thr Leu Met Ile Ser Arg Thr Pro Glu Val Thr Cys Val Val
                         260                 265                 270
        Val Asp Val Ser Gln Glu Asp Pro Glu Val Gln Phe Asn Trp Tyr Val
                         275                 280                 285
        Asp Gly Val Glu Val His Asn Ala Lys Thr Lys Pro Arg Glu Glu Gln
                         290                 295                 300
        Phe Asn Ser Thr Tyr Arg Val Val Ser Val Leu Thr Val Leu His Gln
        305                 310                 315                 320
        Asp Trp Leu Asn Gly Lys Glu Tyr Lys Cys Lys Val Ser Asn Lys Gly
                         325                 330                 335
        Leu Pro Ser Ser Ile Glu Lys Thr Ile Ser Lys Ala Lys Gly Gln Pro
                         340                 345                 350
        Arg Glu Pro Gln Val Tyr Thr Leu Pro Pro Ser Arg Asp Glu Leu Thr
                         355                 360                 365
        Lys Asn Gln Val Ser Leu Thr Cys Leu Val Lys Gly Phe Tyr Pro Ser
                         370                 375                 380
        Asp Ile Ala Val Glu Trp Glu Ser Asn Gly Gln Pro Glu Asn Asn Tyr
        385                 390                 395                 400
        Lys Thr Thr Pro Pro Val Leu Asp Ser Asp Gly Ser Phe Phe Leu Tyr
                         405                 410                 415
        Ser Lys Leu Thr Val Asp Lys Ser Arg Trp Gln Gln Gly Asn Val Phe
                         420                 425                 430
        Ser Cys Ser Val Met His Glu Ala Leu His Asn His Tyr Thr Gln Lys
                         435                 440                 445
```

Ser Leu Ser Leu Ser Pro Gly Lys
    450                 455

<210> SEQ ID NO 43
<211> LENGTH: 1359
<212> TYPE: DNA
<213> ORGANISM: Artificial Sequence
<220> FEATURE:
<223> OTHER INFORMATION: Synthetic

<400> SEQUENCE: 43

```
gaagtgcagc tggtggagtc tgggggaggc ttggtacagc ctggcaggtc cctgagactc      60
tcctgtgcag cctctggatt cacctttgat gattatacca tgcactgggt ccggcaagct     120
ccagggaagg gcctggagtg ggtctcaggt attagttgga atagtggtag tataggctat     180
gcggactctg tgaagggccg attcaccatc tccagagaca acgccaagaa gtccctgtat     240
ctgcaaatga acagtctgag agctgaggac acggccttgt attactgtgc aaaagataat     300
agtggctacg gtcactacta ctacggaatg gacgtctggg gccaagggac cacggtcacc     360
gtcgcctcag cctccaccaa gggcccatcg gtcttccccc tggcaccctc ctccaagagc     420
acctctgggg gcacagcggc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acccagacct acatctgcaa cgtgaatcac aagcccagca acaccaaggt ggacaagaaa     660
gttgagccca aatcttgtga caaaactcac acatgcccac cgtgcccagc accacctgtg     720
gcaggaccat cagtcttcct gttccccccca aaacccaagg acactctcat gatctcccgg     780
accccctgagg tcacgtgcgt ggtggtggac gtgagccagg aagaccccga ggtccagttc     840
aactggtacg tggatggcgt ggaggtgcat aatgccaaga caaagccgcg ggaggagcag     900
ttcaacagca cgtaccgtgt ggtcagcgtc ctcaccgtcc tgcaccagga ctggctgaac     960
ggcaaggagt acaagtgcaa ggtctccaac aaaggcctcc cgtcctccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaacaga    1320
ttcacgcaga agtccctctc cctgtctccg ggtaaatga                           1359
```

<210> SEQ ID NO 44
<211> LENGTH: 452
<212> TYPE: PRT
<213> ORGANISM: Artificial Sequence
<220> FEATURE:
<223> OTHER INFORMATION: Synthetic

<400> SEQUENCE: 44

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Thr Met His Trp Val Arg Gln Ala Pro Gly Lys Gly Leu Glu Trp Val
        35                  40                  45

```
Ser Gly Ile Ser Trp Asn Ser Gly Ser Ile Gly Tyr Ala Asp Ser Val
 50                  55                  60

Lys Gly Arg Phe Thr Ile Ser Arg Asp Asn Ala Lys Lys Ser Leu Tyr
 65                  70                  75                  80

Leu Gln Met Asn Ser Leu Arg Ala Glu Asp Thr Ala Leu Tyr Tyr Cys
                 85                  90                  95

Ala Lys Asp Asn Ser Gly Tyr Gly His Tyr Tyr Gly Met Asp Val
                100                 105                 110

Trp Gly Gln Gly Thr Thr Val Thr Val Ala Ser Ala Ser Thr Lys Gly
                115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Pro Val
225                 230                 235                 240

Ala Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

Gln Glu Asp Pro Glu Val Gln Phe Asn Trp Tyr Val Asp Gly Val Glu
                275                 280                 285

Val His Asn Ala Lys Thr Lys Pro Arg Glu Glu Gln Phe Asn Ser Thr
                290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
                355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn Arg Phe Thr Gln Lys Ser Leu Ser Leu
                435                 440                 445

Ser Pro Gly Lys
450
```

```
<210> SEQ ID NO 45
<211> LENGTH: 330
<212> TYPE: PRT
<213> ORGANISM: Artificial Sequence
<220> FEATURE:
<223> OTHER INFORMATION: Synthetic

<400> SEQUENCE: 45

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 46
<211> LENGTH: 326
<212> TYPE: PRT
<213> ORGANISM: Artificial Sequence
<220> FEATURE:
<223> OTHER INFORMATION: Synthetic
```

<400> SEQUENCE: 46

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 47
<211> LENGTH: 327
<212> TYPE: PRT
<213> ORGANISM: Artificial Sequence
<220> FEATURE:
<223> OTHER INFORMATION: Synthetic

<400> SEQUENCE: 47

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 48
<211> LENGTH: 330
<212> TYPE: PRT
<213> ORGANISM: Artificial Sequence
<220> FEATURE:
<223> OTHER INFORMATION: Synthetic

<400> SEQUENCE: 48

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

```
Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
                325                 330

<210> SEQ ID NO 49
<211> LENGTH: 327
<212> TYPE: PRT
<213> ORGANISM: Artificial Sequence
<220> FEATURE:
<223> OTHER INFORMATION: Synthetic

<400> SEQUENCE: 49

Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80
```

```
Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn Arg Phe Thr Gln Lys Ser
305                 310                 315                 320

Leu Ser Leu Ser Leu Gly Lys
                325

<210> SEQ ID NO 50
<211> LENGTH: 12
<212> TYPE: PRT
<213> ORGANISM: Artificial Sequence
<220> FEATURE:
<223> OTHER INFORMATION: Synthetic

<400> SEQUENCE: 50

Glu Pro Lys Ser Cys Asp Lys Thr His Thr Cys Pro
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Glu Ser Lys Tyr Gly Pro Pro Cys Pro
1               5

<210> SEQ ID NO 52
<211> LENGTH: 8
<212> TYPE: PRT
<213> ORGANISM: Artificial Sequence
```

```
<220> FEATURE:
<223> OTHER INFORMATION: Synthetic

<400> SEQUENCE: 52

Pro Cys Pro Ala Pro Pro Val Ala
1               5

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Glu Pro Lys Ser Cys Asp Lys Thr His Thr Cys Pro Pro Cys Pro Ala
1               5                   10                  15

Pro Pro Val Ala
            20

<210> SEQ ID NO 54
<211> LENGTH: 17
<212> TYPE: PRT
<213> ORGANISM: Artificial Sequence
<220> FEATURE:
<223> OTHER INFORMATION: Synthetic

<400> SEQUENCE: 54

Glu Ser Lys Tyr Gly Pro Pro Cys Pro Pro Cys Pro Ala Pro Pro Val
1               5                   10                  15

Ala

<210> SEQ ID NO 55
<211> LENGTH: 104
<212> TYPE: PRT
<213> ORGANISM: Artificial Sequence
<220> FEATURE:
<223> OTHER INFORMATION: Synthetic

<400> SEQUENCE: 55

Gly Pro Ser Val Phe Leu Phe Pro Pro Lys Pro Lys Asp Thr Leu Met
1               5                   10                  15

Ile Ser Arg Thr Pro Glu Val Thr Cys Val Val Val Asp Val Ser Gln
            20                  25                  30

Glu Asp Pro Glu Val Gln Phe Asn Trp Tyr Val Asp Gly Val Glu Val
        35                  40                  45

His Asn Ala Lys Thr Lys Pro Arg Glu Glu Gln Phe Asn Ser Thr Tyr
    50                  55                  60

Arg Val Val Ser Val Leu Thr Val Leu His Gln Asp Trp Leu Asn Gly
65                  70                  75                  80

Lys Glu Tyr Lys Cys Lys Val Ser Asn Lys Gly Leu Pro Ser Ser Ile
                85                  90                  95

Glu Lys Thr Ile Ser Lys Ala Lys
            100

<210> SEQ ID NO 56
<211> LENGTH: 107
<212> TYPE: PRT
<213> ORGANISM: Artificial Sequence
<220> FEATURE:
<223> OTHER INFORMATION: Synthetic

<400> SEQUENCE: 56
```

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 57
<211> LENGTH: 107
<212> TYPE: PRT
<213> ORGANISM: Artificial Sequence
<220> FEATURE:
<223> OTHER INFORMATION: Synthetic

<400> SEQUENCE: 57

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Pro Gly Lys
            100                 105

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
            35                  40                  45

Asn Asn Tyr Lys Thr Thr Pro Pro Val Leu Asp Ser Asp Gly Ser Phe
        50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr

```
                    85                  90                  95

Thr Gln Lys Ser Leu Ser Leu Ser Leu Gly Lys
            100                 105

<210> SEQ ID NO 59
<211> LENGTH: 107
<212> TYPE: PRT
<213> ORGANISM: Artificial Sequence
<220> FEATURE:
<223> OTHER INFORMATION: Synthetic

<400> SEQUENCE: 59

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn Arg Phe
                85                  90                  95

Thr Gln Lys Ser Leu Ser Leu Ser Leu Gly Lys
            100                 105

<210> SEQ ID NO 60
<211> LENGTH: 98
<212> TYPE: PRT
<213> ORGANISM: Artificial Sequence
<220> FEATURE:
<223> OTHER INFORMATION: Synthetic

<400> SEQUENCE: 60

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 61
<211> LENGTH: 98
<212> TYPE: PRT
<213> ORGANISM: Artificial Sequence
<220> FEATURE:
<223> OTHER INFORMATION: Synthetic

<400> SEQUENCE: 61

Ala Ser Thr Lys Gly Pro Ser Val Phe Pro Leu Ala Pro Cys Ser Arg
1               5                   10                  15
```

```
Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val

<210> SEQ ID NO 62
<211> LENGTH: 106
<212> TYPE: PRT
<213> ORGANISM: Artificial Sequence
<220> FEATURE:
<223> OTHER INFORMATION: Synthetic

<400> SEQUENCE: 62

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 63
<211> LENGTH: 60
<212> TYPE: DNA
<213> ORGANISM: Artificial Sequence
<220> FEATURE:
<223> OTHER INFORMATION: Synthetic

<400> SEQUENCE: 63
ttcgcgcagc ttaggtttat gccaggggggg acgggtggca cgggtcgtgg tggacaccgt    60

<210> SEQ ID NO 64
<211> LENGTH: 40
<212> TYPE: DNA
<213> ORGANISM: Artificial Sequence
<220> FEATURE:
<223> OTHER INFORMATION: Synthetic

<400> SEQUENCE: 64
aagcttatac tcgagctcta gattgggaac ccgggtctct                            40

<210> SEQ ID NO 65
<211> LENGTH: 58
<212> TYPE: DNA
<213> ORGANISM: Artificial Sequence
<220> FEATURE:
<223> OTHER INFORMATION: Synthetic
```

<400> SEQUENCE: 65
cccaccgtgc ccagcaccac ctgtggcagg accatcagtc ttcctgttcc ccccaaaa    58

<210> SEQ ID NO 66
<211> LENGTH: 44
<212> TYPE: DNA
<213> ORGANISM: Artificial Sequence
<220> FEATURE:
<223> OTHER INFORMATION: Synthetic

<400> SEQUENCE: 66
tgtgtcttca gggagaggga cagagaccca tttactcgcc ggcg    44

<210> SEQ ID NO 67
<211> LENGTH: 60
<212> TYPE: DNA
<213> ORGANISM: Artificial Sequence
<220> FEATURE:
<223> OTHER INFORMATION: Synthetic

<400> SEQUENCE: 67
ctcgggttta gaacactgtt ttgagtgtgt acgggtggca cgggtcgtgg tggacaccgt    60

<210> SEQ ID NO 68
<211> LENGTH: 51
<212> TYPE: DNA
<213> ORGANISM: Artificial Sequence
<220> FEATURE:
<223> OTHER INFORMATION: Synthetic

<400> SEQUENCE: 68
aaatcttgtg acaaaactca cacatgccca ccgtgcccag caccacctgt g    51

<210> SEQ ID NO 69
<211> LENGTH: 54
<212> TYPE: DNA
<213> ORGANISM: Artificial Sequence
<220> FEATURE:
<223> OTHER INFORMATION: Synthetic

<400> SEQUENCE: 69
gagaaaacca tctccaaagc caaagggcag ccccgagaac cacaggtgta cacc    54

<210> SEQ ID NO 70
<211> LENGTH: 54
<212> TYPE: DNA
<213> ORGANISM: Artificial Sequence
<220> FEATURE:
<223> OTHER INFORMATION: Synthetic

<400> SEQUENCE: 70
ctcttttggt agaggtttcg gtttcccgtc ggggctcttg gtgtccacat gtgg    54

<210> SEQ ID NO 71
<211> LENGTH: 39
<212> TYPE: DNA
<213> ORGANISM: Artificial Sequence
<220> FEATURE:
<223> OTHER INFORMATION: Synthetic

<400> SEQUENCE: 71
cttcagggag agggacagag gcccatttac tcgccggcg    39

<210> SEQ ID NO 72

-continued

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
gctgacagac taacagactg                                          20

<210> SEQ ID NO 73
<211> LENGTH: 26
<212> TYPE: DNA
<213> ORGANISM: Artificial Sequence
<220> FEATURE:
<223> OTHER INFORMATION: Synthetic

<400> SEQUENCE: 73
atacattata cgaagttata ccggta                                    26

<210> SEQ ID NO 74
<211> LENGTH: 105
<212> TYPE: PRT
<213> ORGANISM: Artificial Sequence
<220> FEATURE:
<223> OTHER INFORMATION: Synthetic

<400> SEQUENCE: 74

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
            100                 105

<210> SEQ ID NO 75
<211> LENGTH: 108
<212> TYPE: PRT
<213> ORGANISM: Artificial Sequence
<220> FEATURE:
<223> OTHER INFORMATION: Synthetic

<400> SEQUENCE: 75

Ala Glu Ile Val Met Thr Gln Ser Pro Ala Thr Leu Ser Val Ser Pro
1               5                   10                  15

Gly Glu Arg Ala Thr Leu Ser Cys Arg Ala Ser Gln Ser Val Ser Ser
            20                  25                  30

Asn Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Glu Phe Thr Leu Thr Ile Ser Ser Leu Gln
65                  70                  75                  80

Ser Glu Asp Phe Ala Val Tyr Tyr Cys Gln His Tyr Ile Asn Trp Pro

```
                    85                  90                  95
Leu Thr Phe Gly Gly Gly Thr Lys Val Glu Ile Lys
                    100                 105
```